(12) United States Patent
Hyde et al.

(10) Patent No.: US 9,730,725 B2
(45) Date of Patent: Aug. 15, 2017

(54) SYSTEMS AND DEVICES FOR CUTTING TISSUE

(71) Applicant: Elwha LLC, Bellevue, WA (US)

(72) Inventors: Roderick A. Hyde, Redmond, WA (US); Gary L. McKnight, Bothell, WA (US); Nathan P. Myhrvold, Medina, WA (US); Lowell L. Wood, Jr., Bellevue, WA (US)

(73) Assignee: Elwha LLC, Bellevue, WA (US)

( * ) Notice: Subject to any disclaimer, the term of this patent is extended or adjusted under 35 U.S.C. 154(b) by 336 days.

(21) Appl. No.: 14/510,378

(22) Filed: Oct. 9, 2014

(65) Prior Publication Data

US 2016/0100854 A1    Apr. 14, 2016

(51) Int. Cl.
*A61B 17/3205* (2006.01)
*A61B 10/02* (2006.01)
(Continued)

(52) U.S. Cl.
CPC .... *A61B 17/32056* (2013.01); *A61B 10/0283* (2013.01); *A61B 90/361* (2016.02); *A61B 5/14546* (2013.01); *A61B 5/4836* (2013.01); *A61B 17/32002* (2013.01); *A61B 18/06* (2013.01); *A61B 18/082* (2013.01); *A61B 34/30* (2016.02); *A61B 90/30* (2016.02); *A61B 90/98* (2016.02); *A61B 2017/00022* (2013.01); *A61B 2017/00199* (2013.01);
(Continued)

(58) Field of Classification Search
CPC .. A61B 17/32002; A61B 2017/320733; A61B 17/320758; A61B 2017/320791; A61B 17/320725; A61B 17/32056
See application file for complete search history.

(56) References Cited

U.S. PATENT DOCUMENTS

| 4,384,288 A | 5/1983 | Walton |
| 5,030,201 A | 7/1991 | Palestrant |

(Continued)

OTHER PUBLICATIONS

Barlen et al.; "Detection of *Salmonella* by Surface Plasmon Resonance"; Sensors; bearing a date of Jun. 26, 2007; pp. 1427-1446; vol. 7; MDPI.

(Continued)

*Primary Examiner* — Thomas McEvoy

(57) ABSTRACT

Systems and devices are described which include a tissue cutting device including a central rotatable shaft having a first end and a second end; a motor operably coupled to the first end of the central rotatable shaft, the motor including circuitry configured to rotate the central rotatable shaft; a tethering component; and an elongated flexible cutting component having a first end and a second end, the first end of the elongated flexible cutting component secured to the central rotatable shaft at a position between the first end and the second end central rotatable shaft, the second end of the elongated flexible cutting component operably coupled to the tethering component, the tethering component configured to at least one of extend and retract the elongated flexible cutting component; wherein extension and retraction of the elongated flexible cutting component by the tethering component changes a shape formed by the elongated flexible cutting component.

41 Claims, 23 Drawing Sheets

(51) Int. Cl.

| | | |
|---|---|---|
| *A61B 90/00* | (2016.01) | |
| *A61B 17/32* | (2006.01) | |
| *A61B 5/00* | (2006.01) | |
| *A61B 18/00* | (2006.01) | |
| *A61B 17/00* | (2006.01) | |
| *A61B 90/30* | (2016.01) | |
| *A61B 90/98* | (2016.01) | |
| *A61B 5/145* | (2006.01) | |
| *A61B 18/06* | (2006.01) | |
| *A61B 18/08* | (2006.01) | |
| *A61B 18/14* | (2006.01) | |
| *A61B 34/30* | (2016.01) | |

(52) U.S. Cl.
CPC ............... *A61B 2017/00398* (2013.01); *A61B 2017/00526* (2013.01); *A61B 2017/00734* (2013.01); *A61B 2017/320032* (2013.01); *A61B 2018/00595* (2013.01); *A61B 2018/144* (2013.01); *A61B 2090/378* (2016.02); *A61B 2217/005* (2013.01); *A61B 2217/007* (2013.01); *A61B 2218/002* (2013.01); *A61B 2218/007* (2013.01)

(56) References Cited

U.S. PATENT DOCUMENTS

| | | | |
|---|---|---|---|
| 5,318,576 A * | 6/1994 | Plassche, Jr. | .. A61B 17/320725 604/22 |
| 5,882,329 A | 3/1999 | Patterson et al. | |
| 7,215,976 B2 | 5/2007 | Brideglall | |
| 7,507,675 B2 | 3/2009 | Zuilhof et al. | |
| 7,612,424 B1 | 11/2009 | Espinosa et al. | |
| 7,806,871 B2 | 10/2010 | Li et al. | |
| 8,012,153 B2 | 9/2011 | Woloszko et al. | |
| 8,062,298 B2 | 11/2011 | Schmitz et al. | |
| 8,062,300 B2 | 11/2011 | Schmitz et al. | |
| 8,128,568 B2 | 3/2012 | Wang et al. | |
| 8,808,295 B2 | 8/2014 | Vercellotti et al. | |
| 8,814,921 B2 | 8/2014 | Aljuri et al. | |
| 2008/0058758 A1 | 3/2008 | Ranchod et al. | |
| 2008/0147084 A1 | 6/2008 | Bleich et al. | |
| 2009/0018565 A1 | 1/2009 | To et al. | |
| 2012/0046679 A1 | 2/2012 | Patel et al. | |
| 2012/0209273 A1 * | 8/2012 | Zaretzka | .......... A61B 17/32002 606/80 |
| 2014/0277009 A1 * | 9/2014 | Thatipelli | ...... A61B 17/320758 606/159 |

OTHER PUBLICATIONS

Berggren et al.; "Capacitive Biosensors"; Electroanalysis; bearing a date of Jul. 7, 2000; pp. 173-180; vol. 13, No. 3; WILEY-VCH Verlag GmbH.

Cetin et al.; "Handheld high-throughput plasmonic biosensor using computational on-chip imaging"; Light: Science & Applications; bearing a date of Apr. 8, 2013; pp. 1-10; vol. 3; CIOMP.

Chawla et al.; "An Overview of Passive RFID"; IEEE Applications & Practice; Sep. 2007; pp. 11-17; IEEE.

Chen et al.; "Rare cell isolation and analysis in microfluidics"; Lab Chip; bearing a date of Jan. 9, 2014; pp. 626-645; vol. 14; The Royal Society of Chemistry.

Cui et al.; "Nanowire Nanosensors for Highly Sensitive and Selective Detection of Biological Chemical Species"; Science; Aug. 17, 2001; pp. 1289-1292; vol. 293; American Association for the Advancement of Science.

Finkenzeller, Klaus; "Fundamental Operating Principles"; RFID Handbook: Fundamentals and Applications in Contactless Smart Cards and Identification; printed on Oct. 8, 2014; pp. 29-59; John Wiley & Sons, Ltd.

Harz et al.; "Vibrational Spectroscopy—A Powerful Tool for the Rapid Identification of Microbial Cells at the Single-Cell Level"; Cytometry Part A; bearing a date of Dec. 23, 2008; pp. 104-113; International Society for Advancement of Cytometry.

Kashyap et al.; "Surface Plasmon Resonance-Based Fiber and Planar Waveguide Sensors"; Journal of Sensors; bearing a date of Mar. 29, 2009; pp. 1-9; vol. 2009; Hindawi Publishing Corporation.

Kim et al.; "A class of micromachined magnetic resonator for high-frequency magnetic sensor applications"; Journal of Applied Physics; bearing a date of Nov. 1, 2005; pp. 1-3; American Institute of Physics.

Kim et al.; "Lens-Free Imaging for Biological Applications"; Journal of Laboratory of Automation; bearing a date of Jun. 18, 2013; pp. 43-49; vol. 17, No. 1; SAGE.

Lim et al.; "A Micromechanical Biosensor with Interdigitated Capacitor Readout"; Proceedings of the 2011 IEEE/ICME International Conference on Complex Medical Engineering; printed on Oct. 8, 2014; pp. 42-46; IEEE.

Massarweh et al.; "Electrosurgery: History, Principles, and Current and Future Uses"; J Am Coll Surg; Mar. 2006; pp. 520-530; vol. 202, No. 3; Elsevier Inc.

Murakami et al.; "A Miniature Confocal Optical Microscope with MEMS Gimbal Scanner"; The 12th International Conference on Solid State Sensors, Actuators and Microsystems; Jun. 8-12, 2003; pp. 587-590; IEEE.

Ohno et al.; "Graphene Field-Effect Transistors for Label-Free Biological Sensors"; IEEE Sensors 2010 Conference; printed on Oct. 8, 2014; pp. 903-906; IEEE.

Seidl et al.; "Opto-Mechanical Combination of a Line Scanning Camera and a Micro Laser Scanner System"; printed on Oct. 8, 2014; 6 pages.

Son et al.; "An Implantable Wireless Microdosimeter for Radiation Oncology"; MEMS 2008; Jan. 13-17, 2008; pp. 256-259; IEEE.

Tehrani et al.; "Detection of Monoclonal Antibodies using Chemically Modified Graphite Substrates"; IEEE Sensors 2010 Conference; printed on Oct. 8, 2014; pp. 428-431; IEEE.

* cited by examiner

FIG. 3A
FIG. 3B
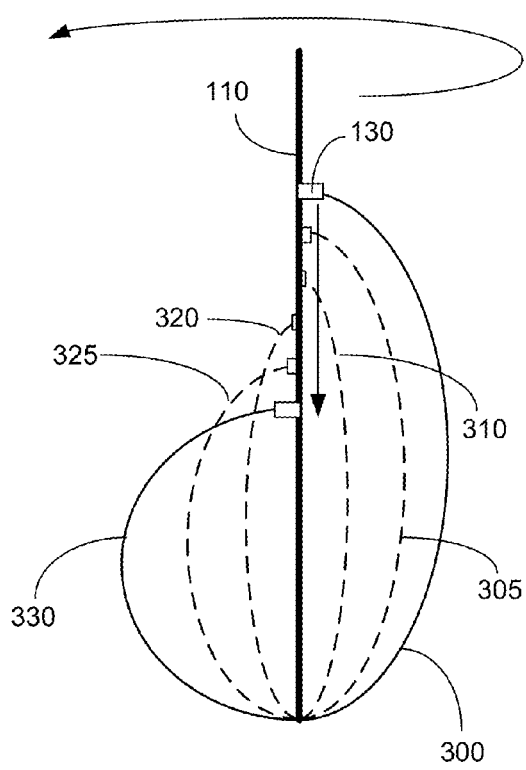
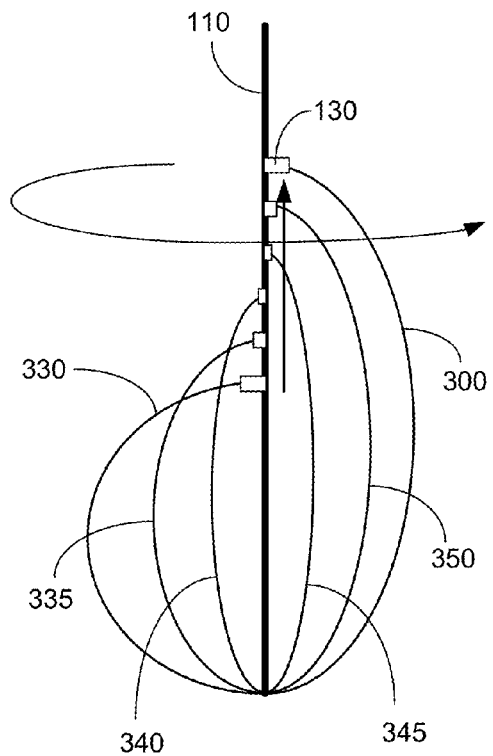

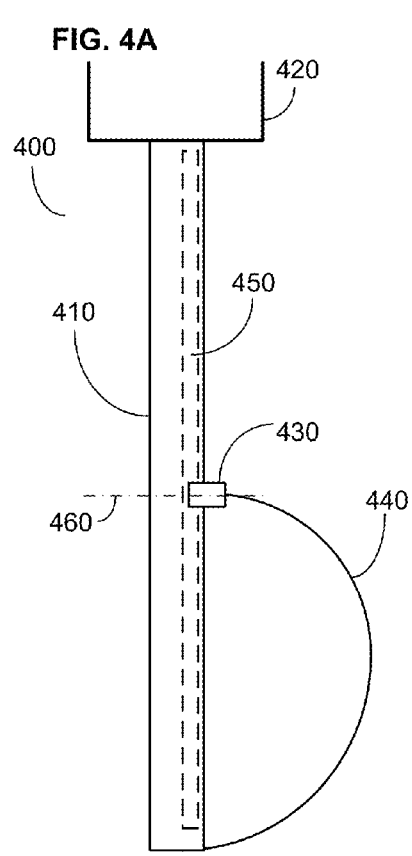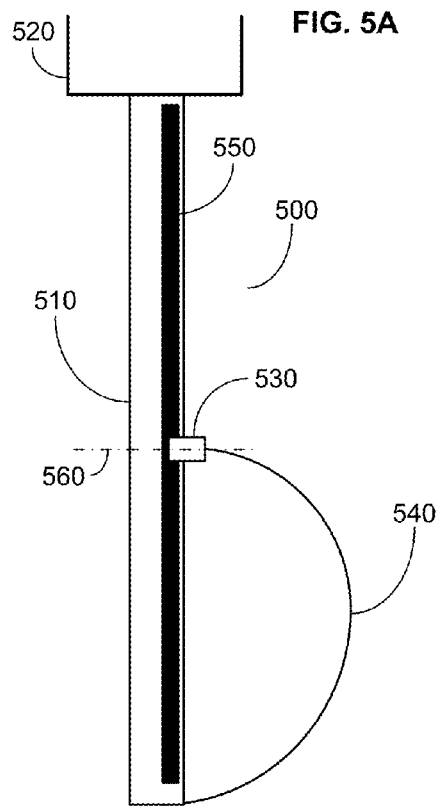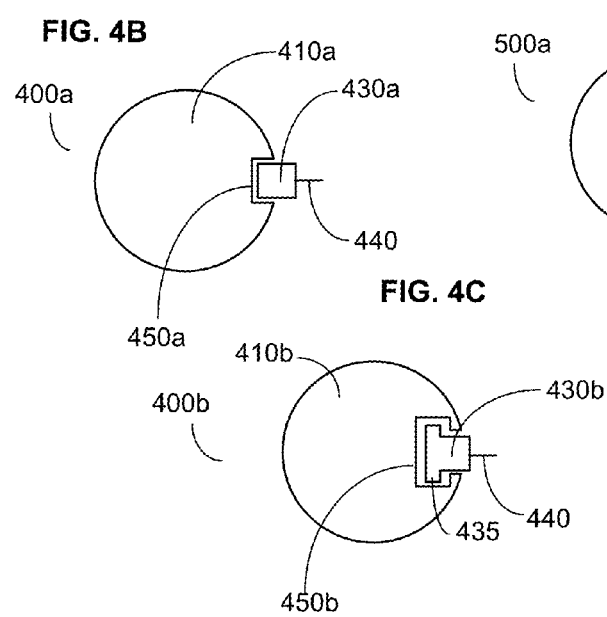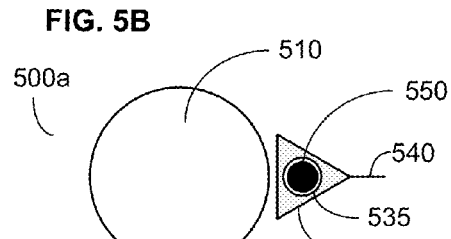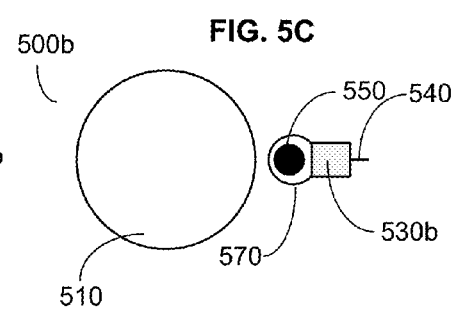

FIG. 17A
FIG. 17B
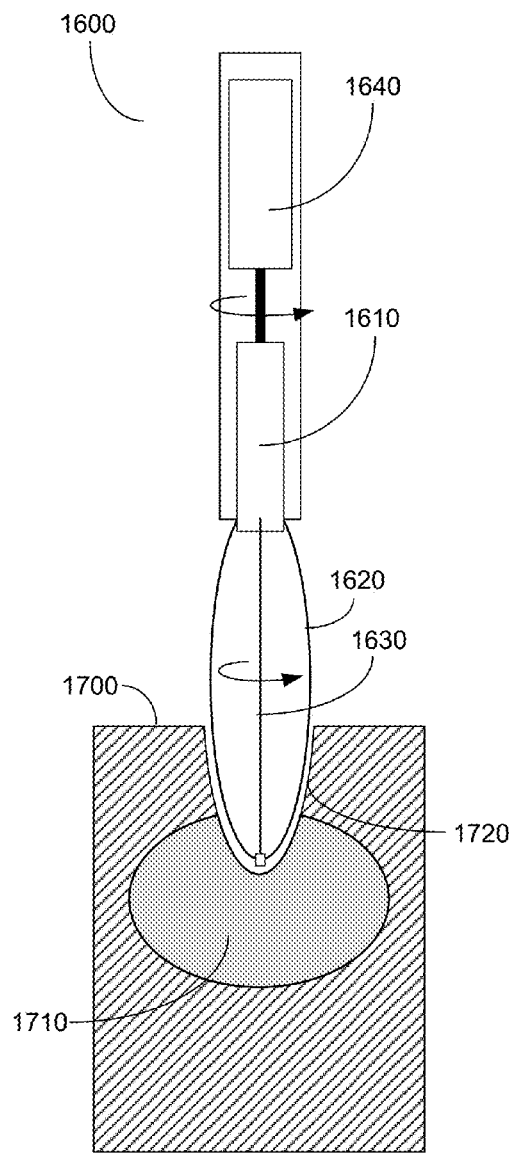
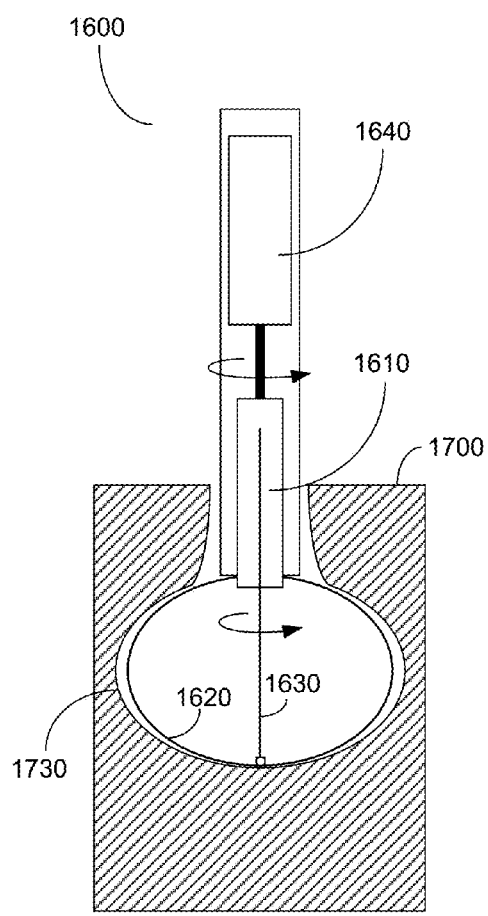

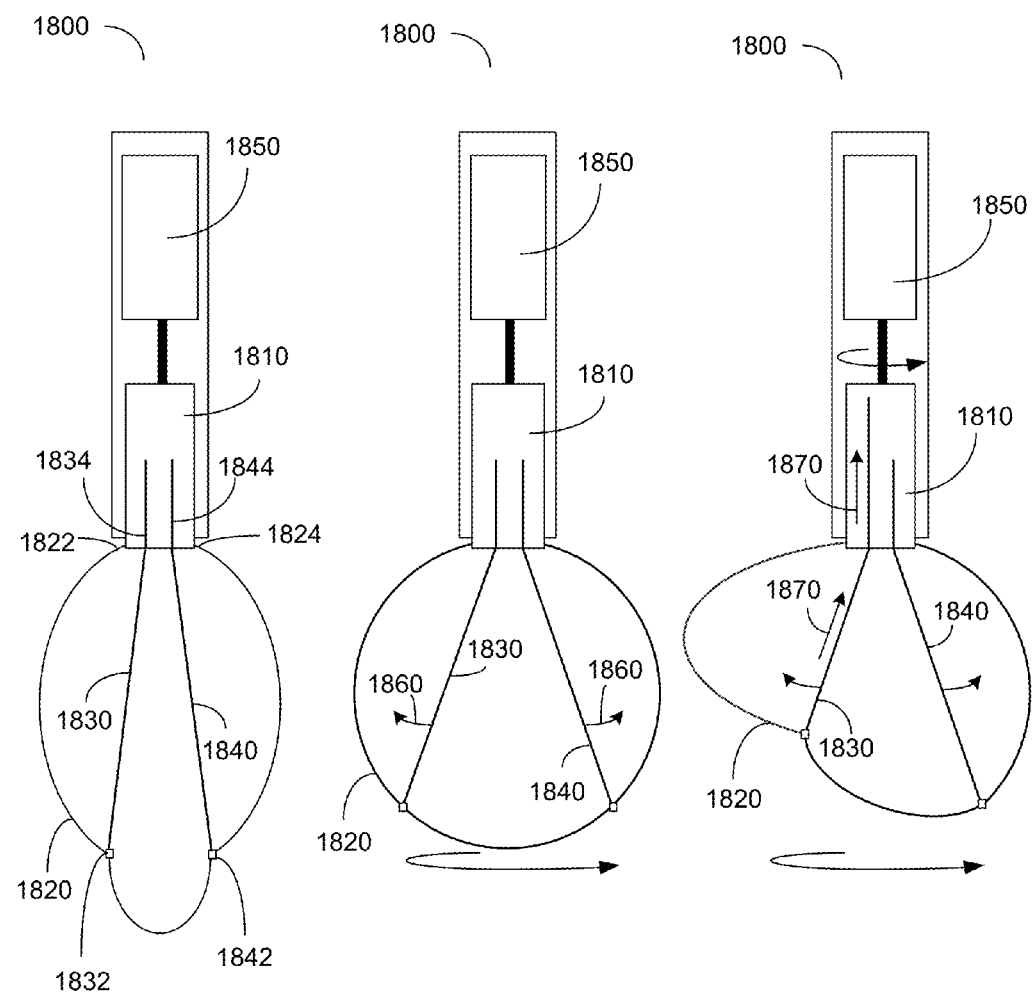

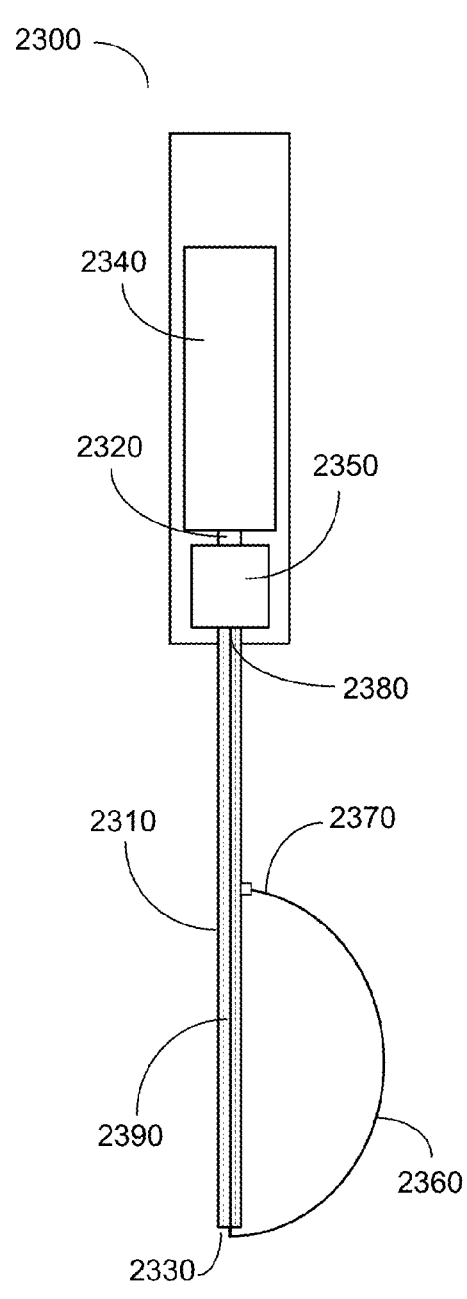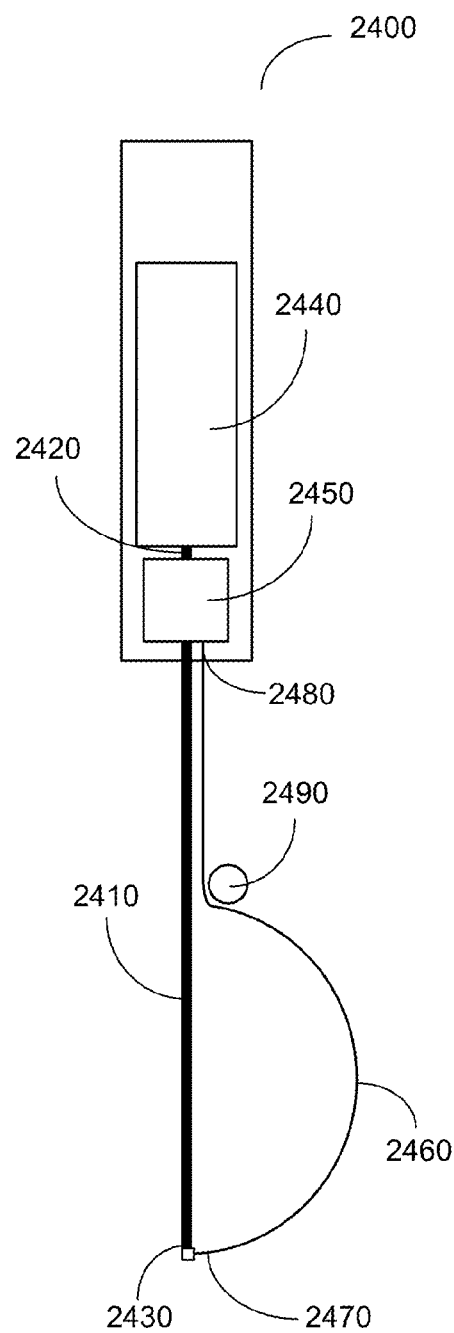

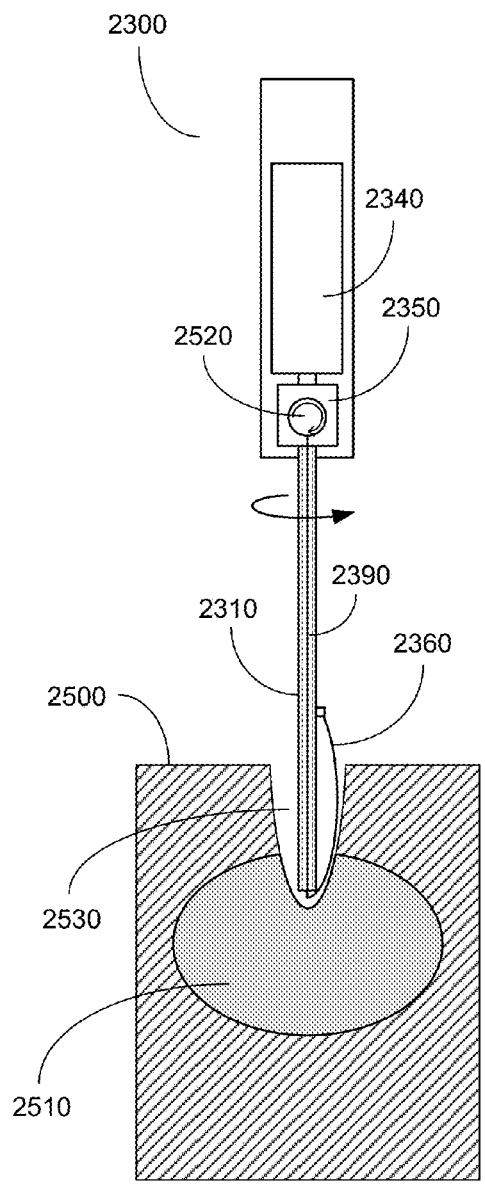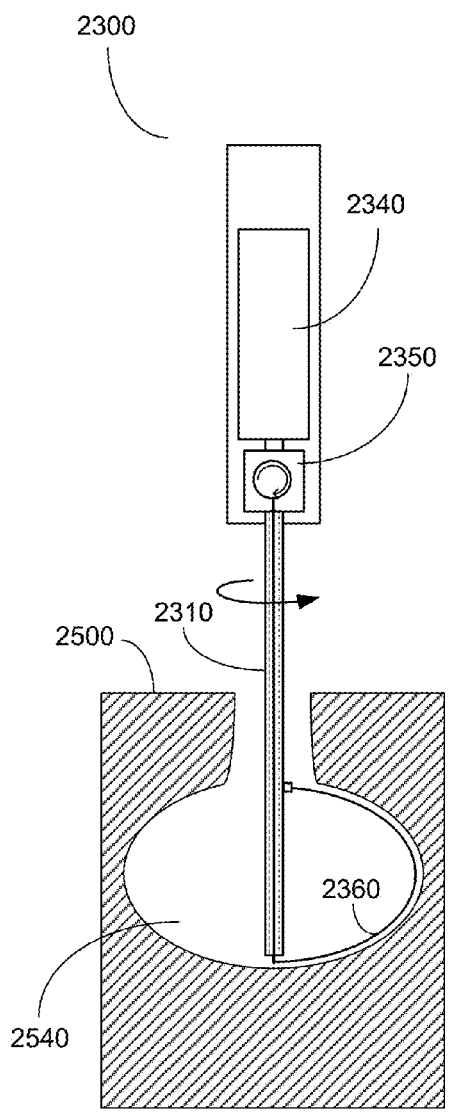
FIG. 25A
FIG. 25B

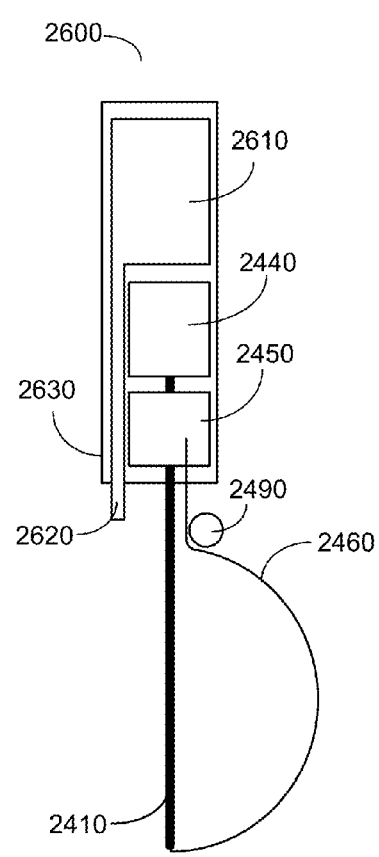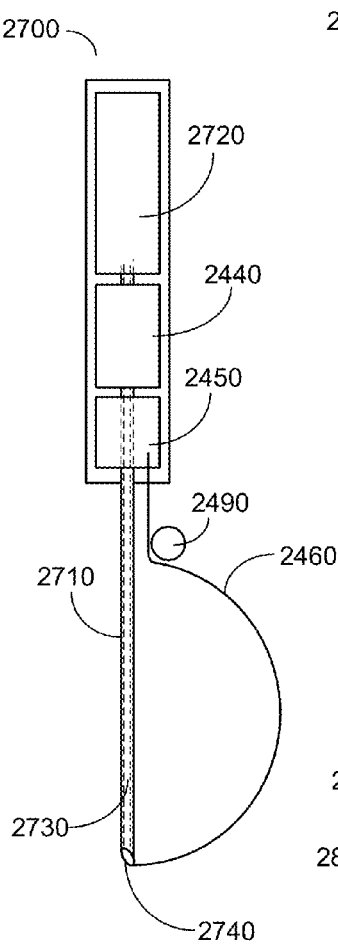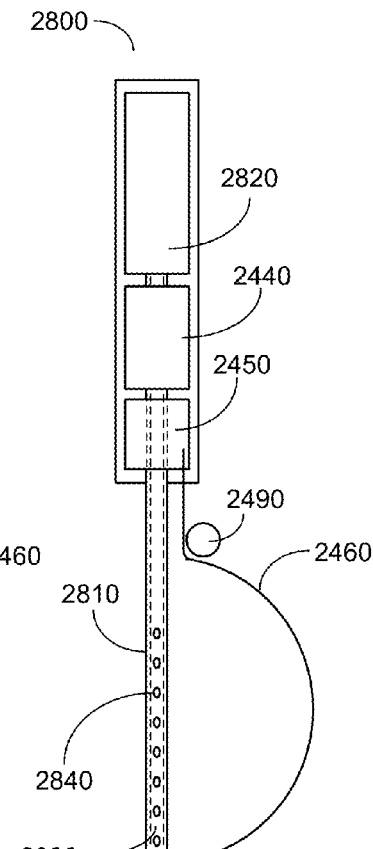

SYSTEMS AND DEVICES FOR CUTTING TISSUE

If an Application Data Sheet (ADS) has been filed on the filing date of this application, it is incorporated by reference herein. Any applications claimed on the ADS for priority under 35 U.S.C. §§119, 120, 121, or 365(c), and any and all parent, grandparent, great-grandparent, etc. applications of such applications, are also incorporated by reference, including any priority claims made in those applications and any material incorporated by reference, to the extent such subject matter is not inconsistent herewith.

CROSS-REFERENCE TO RELATED APPLICATIONS

The present application claims the benefit of the earliest available effective filing date(s) from the following listed application(s) (the "Priority Applications"), if any, listed below (e.g., claims earliest available priority dates for other than provisional patent applications or claims benefits under 35 USC §119(e) for provisional patent applications, for any and all parent, grandparent, great-grandparent, etc. applications of the Priority Application(s)).

PRIORITY APPLICATIONS

None

If the listings of applications provided above are inconsistent with the listings provided via an ADS, it is the intent of the Applicant to claim priority to each application that appears in the Domestic Benefit/National Stage Information section of the ADS and to each application that appears in the Priority Applications section of this application.

All subject matter of the Priority Applications and of any and all applications related to the Priority Applications by priority claims (directly or indirectly), including any priority claims made and subject matter incorporated by reference therein as of the filing date of the instant application, is incorporated herein by reference to the extent such subject matter is not inconsistent herewith.

SUMMARY

In an aspect, a tissue cutting device includes, but is not limited to, a central rotatable shaft having a first end and a second end; a motor operably coupled to the first end of the central rotatable shaft, the motor including circuitry configured to rotate the central rotatable shaft; a moveable component configured to move along at least a portion of the length of the central rotatable shaft; and an elongated flexible cutting component having a first end and a second end, the first end of the elongated flexible cutting component secured to the moveable component and the second end of the elongated flexible cutting component secured to the central rotatable shaft in proximity to the second end of the central rotatable shaft; wherein movement of the moveable component along the at least a portion of the length of the central rotatable shaft changes a shape formed by the elongated flexible cutting component. In addition to the foregoing, other device aspects are described in the claims, drawings, and text forming a part of the present disclosure.

In an aspect, a tissue cutting system includes, but is not limited to, a tissue cutting device including a central rotatable shaft having a first end and a second end; a motor operably coupled to the first end of the central rotatable shaft, the motor including circuitry configured to rotate the central rotatable shaft; a moveable component configured to move along at least a portion of the length of the central rotatable shaft; and an elongated flexible cutting component having a first end and a second end, the first end of the elongated flexible cutting component secured to the moveable component and the second end of the elongated flexible cutting component secured to the central rotatable shaft in proximity to the second end of the central rotatable shaft; wherein movement of the moveable component along the at least a portion of the length of the central rotatable shaft changes a shape formed by the elongated flexible cutting component; and a computing component operably connected to the tissue cutting device, the computing component including a processor and circuitry. In addition to the foregoing, other system aspects are described in the claims, drawings, and text forming a part of the present disclosure.

In an aspect, a tissue cutting device includes, but is not limited to, a tethering component; an elongated flexible cutting component having a first end and a second end, the first and the second end of the elongated flexible cutting component secured to the tethering component; at least one tether having a first end and a second end, the first end of the at least one tether attached to the elongated flexible cutting component at a position between the first and the second end of the elongated flexible cutting component, the second end of the at least one tether operably coupled to the tethering component, the tethering component configured to at least one of extend and retract the at least one tether; and a motor operably coupled to the tethering component, the motor including circuitry configured to rotate the tethering component and the secured elongated flexible cutting component; wherein extension and refraction of the at least one tether by the tethering component changes a shape formed by the elongated flexible cutting component. In addition to the foregoing, other device aspect are described in the claims, drawings, and text forming a part of the present disclosure.

In an aspect, a tissue cutting system includes, but is not limited to, a tissue cutting device including a tethering component, an elongated flexible cutting component having a first end and a second end, the first end and the second end of the elongated flexible cutting component secured to the tethering component, at least one tether having a first end and a second end, the first end of the at least one tether attached to the elongated flexible cutting component at a position between the first end and the second end of the elongated flexible cutting component, the second end of the at least one tether operably coupled to the tethering component, the tethering component configured to at least one of extend and retract the at least one tether, and a motor operably coupled to the tethering component, the motor including circuitry configured to rotate the tethering component and the secured elongated flexible cutting component; and a computing component operably coupled to the tissue cutting device, the computing component including a processor and circuitry. In addition to the foregoing, other system aspects are described in the claims, drawings, and text forming a part of the present disclosure.

In an aspect, a tissue cutting device includes, but is not limited to, a central rotatable shaft having a first end and a second end; a motor operably coupled to the first end of the central rotatable shaft, the motor including circuitry configured to rotate the central rotatable shaft; a tethering component; and an elongated flexible cutting component having a first end and a second end, the first end of the elongated flexible cutting component secured to the central rotatable shaft at a position between the first end and the second end of the central rotatable shaft, the second end of the elongated flexible cutting component operably coupled to the tethering component, the tethering component configured to at least one of extend and retract the elongated flexible cutting component; wherein extension and retraction of the elongated flexible cutting component by the tethering component changes a shape formed by the elongated flexible cutting component. In addition to the foregoing, other device aspects are described in the claims, drawings, and text forming a part of the present disclosure.

In an aspect, a tissue cutting system includes, but is not limited to a tissue cutting device including a central rotatable shaft having a first end and a second end, a motor operably coupled to the first end of the central rotatable shaft, the motor including circuitry configured to rotate the central rotatable shaft, a tethering component, and an elongated flexible cutting component having a first end and a second end, the first end of the elongated flexible cutting component secured to the central rotatable shaft at a position between the first and the second end of the central rotatable shaft, the second end of the elongated flexible cutting component operably coupled to the tethering component, the tethering component configured to at least one of extend and retract the elongated flexible cutting component; and a computing component operably connected to the tissue cutting device, the computing component including a processor and circuitry. In addition to the foregoing, other system aspects are described in the claims, drawings, and text forming a part of the present disclosure.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 3A is a schematic of a shape formed by a rotating elongated flexible cutting component.
FIG. 3B is a schematic of a shape formed by a rotating elongated flexible cutting component.
FIG. 4A is a schematic of a tissue cutting device including a moveable component associated with a central rotatable shaft.
FIG. 4B is a schematic of a cross-section through a moveable component associated with a central rotatable shaft.
FIG. 4C is a schematic of a cross-section through a moveable component associated with a central rotatable shaft.
FIG. 5A is a schematic of a tissue cutting device including a moveable component associated with a central rotatable shaft.
FIG. 5B is a schematic of a cross-section through a moveable component associated with a central rotatable shaft.
FIG. 5C is a schematic of a cross-section through a moveable component associated with a central rotatable shaft.
FIG. 17A is a schematic of a tissue cutting device including at least one tether at a first position in a tissue.
FIG. 17B is a schematic of a tissue cutting device including at least one tether at a second position in a tissue.
FIG. 18A is a schematic of a tissue cutting device including two tethers.
FIG. 18B is a schematic of a tissue cutting device including two tethers with an elongated flexible cutting component forming a first shape.
FIG. 18C is a schematic of a tissue cutting device including two tethers with an elongated flexible cutting component forming a second shape.
FIG. 23 is a schematic of a tissue cutting device.
FIG. 24 is a schematic of a tissue cutting device.
FIG. 25A is a schematic of a tissue cutting device at a first position in a tissue.
FIG. 25B is a schematic of a tissue cutting device at a second position in a tissue.
FIG. 26 is a schematic of a tissue cutting device including an aspiration component.
FIG. 27 is a schematic of a tissue cutting device including an aspiration component.
FIG. 28 is a schematic of a tissue cutting device including an aspiration component.

DETAILED DESCRIPTION

Figure 1:
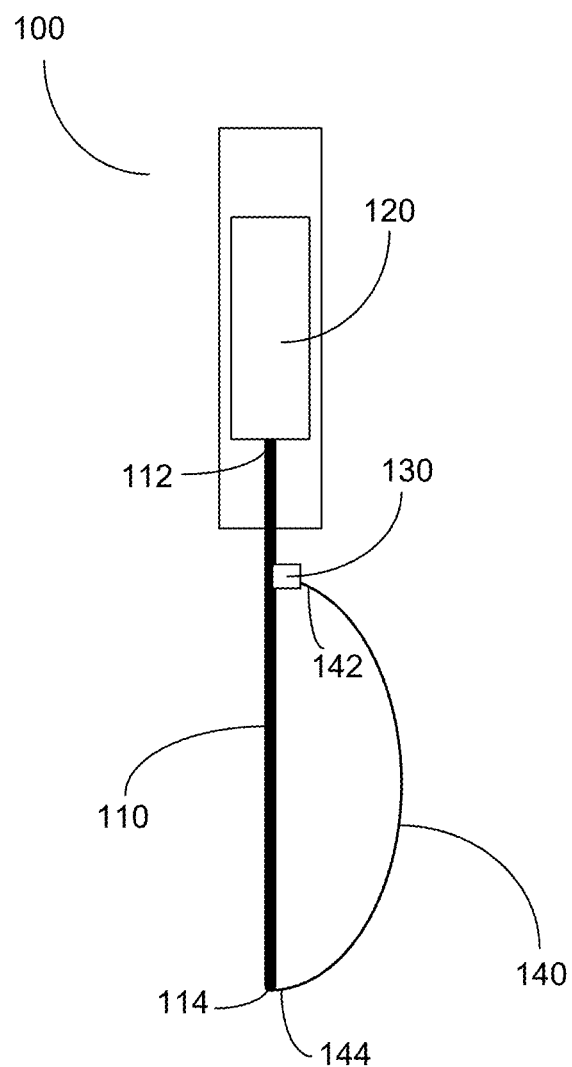
FIG. 1 is a schematic of tissue cutting device.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

FIG. 1 illustrates aspects of a tissue cutting device. Tissue cutting device 100 includes central rotatable shaft 110 having a first end 112 and a second end 114.

Tissue cutting device 100 further includes motor 120 operably coupled to the first end 112 of central rotatable shaft 110, the motor 120 including circuitry configured to rotate the central rotatable shaft 110. Tissue cutting device 100 further includes moveable component 130 configured to move along at least a portion of the length of the central rotatable shaft 110. Tissue cutting device 100 further includes an elongated flexible cutting component 140 having a first end 142 and a second end 144, the first end 142 of the elongated flexible cutting component 140 secured to the moveable component 130 and the second end of the elongated flexible cutting component secured to the central rotatable shaft 110 in proximity to the second end 114 of the central rotatable shaft 110. The movement of the moveable component 130 along the at least a portion of the length of the central rotatable shaft 110 changes a shape formed by the elongated flexible cutting component 110.

In an aspect, the elongated flexible cutting component 110 forms a D-shape when attached at the first end to the moveable component and at the second end to the central rotatable shaft in proximity to the second end of the central rotatable shaft. In an aspect, movement of the moveable component along the at least a portion of the length of the central rotatable shaft changes aspects of the D-shape formed by the elongated flexible cutting component. For example, the D-shape can be lengthened and flattened as the first end of the elongated flexible cutting component attached to the moveable component moves away from the second end of the elongated flexible cutting component attached to the central rotatable shaft. For example, the D-shape can be shortened and widened as the first end of the elongated flexible cutting component attached to the moveable component moves towards the second end of the elongated flexible cutting component attached to the central rotatable shaft. In an aspect, the shape formed by the elongated flexible cutting component is fixed. For example, the moveable component can be positioned and locked into place prior to a cutting procedure, the radius of the shape formed by the elongated flexible cutting component, e.g., a D-shape, remaining constant and creating a symmetrical cutting pattern upon rotation of the central rotatable shaft and the attached elongated flexible cutting component.

In an aspect, the shape formed by the elongated flexible cutting component varies through the course of a cutting procedure. For example, the radius of the rotating elongated flexible cutting component can vary as the tissue cutting device is moved into the tissue, with a small cutting radius at the point of entering the tissue and a larger cutting radius once the target tissue for resection has been reached.

Figure 2A:
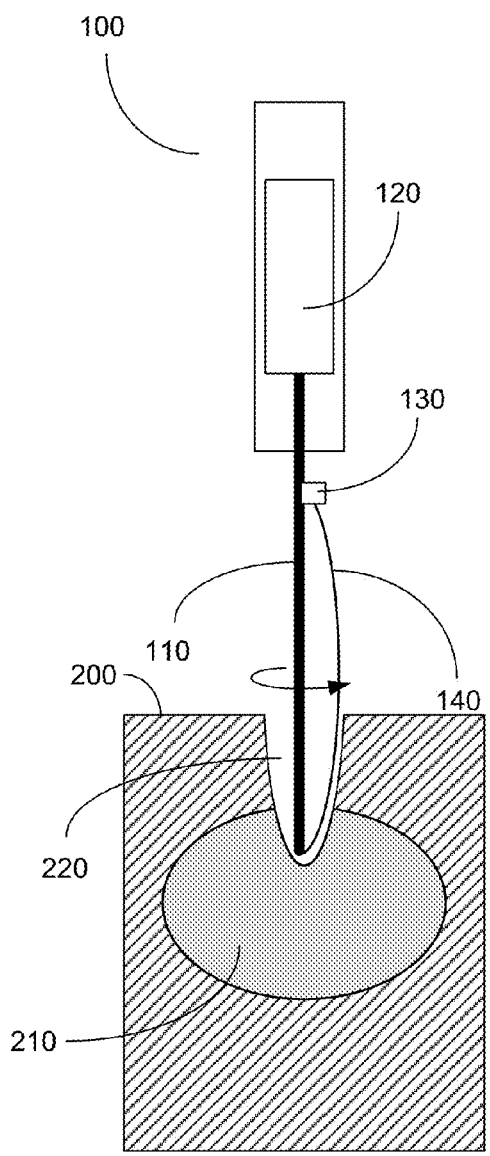
FIG. 2A is a schematic of a tissue cutting device at a first position in a tissue.
Figure 2B:
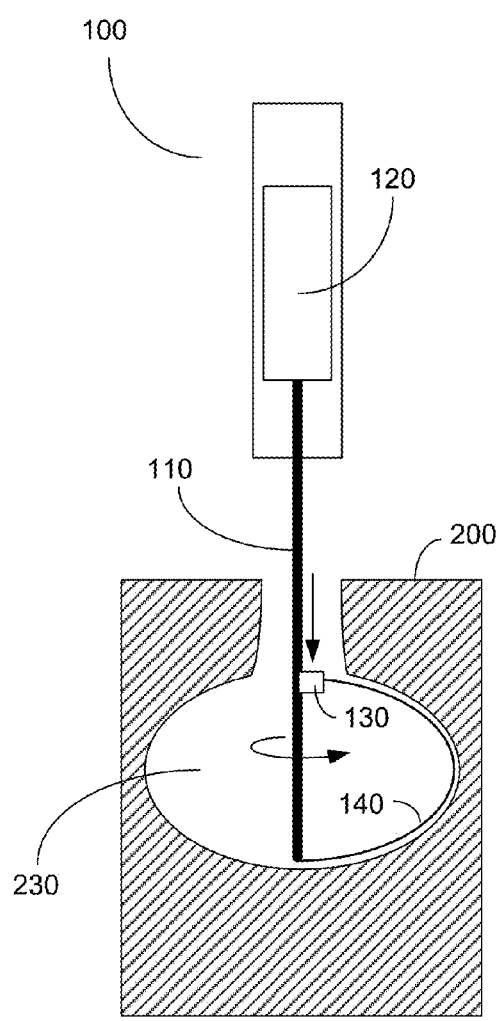
FIG. 2B is a schematic of a tissue cutting device at a second position in a tissue.

FIGS. 2A and 2B illustrate changes in the shape formed by the elongated flexible cutting component as well as the tissue cutting pattern in response to moving the moveable component along the at least a portion of the length of the central rotatable shaft to change the shape formed by the elongated flexible cutting component. FIG. 2A shows tissue cutting device 100 at a first time point relative to tissue 200. Tissue cutting device 100 includes central rotatable shaft 110, motor 120, moveable component 130, and elongated flexible cutting component 140. Tissue cutting device 100 is shown cutting into tissue 200 and target tissue mass 210. Moveable component 130 and elongated flexible cutting component 140 are in a first position that creates resected space 220 as central rotatable shaft 130 and attached elongated flexible cutting component 140 are rotated by motor 120. As the elongated flexible cutting component 140 rotates, it cuts away at tissue 200 in a pattern dependent upon the shape formed by the elongated flexible cutting component 140. FIG. 2B shows tissue cutting device 100 at a second time point relative to tissue 200. At this point, central rotatable shaft 110 is shown further into tissue 200. Moveable component 130 and elongated flexible cutting component 140 are in a second position that creates resected space 230 as central rotatable shaft 110 and attached elongated flexible cutting component 140 are rotated by motor 120. In this example, tissue mass 210 has been removed, leaving resected space 230.

In an aspect, a tissue cutting device such as described herein is used for minimally invasive surgery to cut and resect tissue. In an aspect, the tissue cutting device is inserted into a tissue of a patient. In some embodiments, the distal portion of the tissue cutting device (e.g., the second end of the central rotatable shaft) is adapted to pierce tissue. In other embodiments, the tissue cutting device is inserted into a previously established surgical incision (e.g., a 0.5 cm to 2 cm incision). In an aspect, the tissue cutting device is inserted into a body lumen (e.g., a blood vessel, gastrointestinal tract, vagina, rectum, airway, ureter, or urethra).

A tissue cutting device such as described herein can enter tissue by any of a number of routes including, but not limited to, transabdominal, transperineal, transcutaneous, transvascular, transurethral, transureteral, transoral, transvaginal, and transrectal routes of insertion. A wide range of tissue can be cut and resected including but not limited to prostatic tissue, kidney tissue, liver tissue, uterine tissue, bladder tissue, and brain tissue. In an aspect, the tissue to be cut and resected is benign tissue (e.g., fibrotic tissue in uterus or prostate). In an aspect, the tissue to be cut and resected is malignant tissue (e.g., a solid tumor).

In an aspect, the tissue cutting device is sized for placement into cannula or trocar. For example, the central rotatable shaft, moveable component, and elongated flexible cutting component of the tissue cutting device may be extended from or retracted into a cannula or trocar configured for performing minimally invasive surgery.

In an aspect, the tissue cutting device includes a hand-held device configured for use by a surgeon or other medical practitioner. In an aspect, the tissue cutting device is included in a robotic surgery apparatus. For example, the tissue cutting device can be included in a computer-assisted surgery apparatus, a robotically-assisted surgery apparatus, an unmanned surgery apparatus, and the like. For example, the tissue cutting device can be included in a steerable catheter system. For example, the tissue cutting device can be included in a daVinci® type of robotic system (from, Intuitive Surgical, Inc., Sunnyvale, Calif.).

In an aspect, the shape formed by the elongated flexible cutting component is varied during the course of a single rotation. For example, the characteristics of the D-shape formed by the elongated flexible cutting component can be varied during the course of a single rotation by coordinating the movement of the moveable component with the rotational movement of the central rotatable shaft. In an aspect, varying the shape formed by the elongated flexible cutting component during the course of a single rotation results in an asymmetrical cutting pattern.

FIGS. 3A and 3B illustrate aspects of a single rotation of a central rotatable shaft as the moveable component and attached elongated flexible cutting component are moved along the length of the central rotatable shaft. FIG. 3A illustrates a 180 degree rotation of central rotatable shaft 110. Elongated flexible cutting component at 0 degrees (300) is shown rotating in a counter-clockwise manner into the plane of the page. Shown is the elongated flexible cutting component at 30 degrees (305), the elongated flexible cutting component at 60 degrees (310), the elongated flexible cutting component at 120 degrees (320), the elongated flexible cutting component at 150 degrees (325), and the elongated flexible cutting component at 180 degrees (330). As the elongated flexible cutting component rotates through the various degrees of the rotation, the shape formed by the elongated flexible cutting component changes, i.e., becomes shorter and wider, in response to movement of the moveable component 130 along the central rotatable shaft 110 towards the second end of the elongated flexible cutting component. FIG. 3B illustrates another 180 degrees of rotation of central rotatable shaft 110 to complete a full rotation. The elongated flexible cutting component at 180 degrees (330) is shown rotating out of the plane of the page. Shown is the elongated flexible cutting component at 210 degrees (335), the elongated flexible cutting component 240 degrees (340), the elongated flexible cutting component 300 degrees (345), the elongated flexible cutting component at 330 degrees (350), and the elongated flexible cutting component at 360 degrees (300). As the elongated flexible cutting component rotates through the various degrees of the rotation, the shape formed by the elongated flexible cutting component changes, i.e., becomes longer and narrower, in response to movement of the moveable component 130 along the central rotatable shaft 110 away from the second end of the elongated flexible cutting component. During the course of a 360 rotation, the shape formed by the elongated flexible cutting component changes, creating an asymmetrical cutting pattern.

Motor

A tissue cutting device such as described herein includes a motor. In an aspect, the motor is operably coupled to the first end of the central rotatable shaft and includes circuitry configured to rotate the central rotatable shaft. In an aspect, the motor is an electric motor. In an aspect, the motor has a single rotational frequency. In an aspect, the motor includes a simple on/off switch and a single rotational frequency. For example, the motor can include an on/off switch which when turned on rotates the central rotatable shaft at a fixed rotational frequency. In an aspect, the motor includes variable rotational frequency. In an aspect, the motor includes circuitry configured to control the rotational frequency of the motor. For example, the motor can include a user interface (e.g., a dial or buttons) to allow a user to increase or decrease the rotational frequency. In an aspect, the motor is operably coupled to a computing component, the computing component including circuitry to control the rotational frequency of the motor.

In an aspect, the motor is a rotary shaft motor, such as a conventional DC, pulse, or AC motor. In an aspect, the motor can include a brush DC motor. In an aspect, the motor can include a DC servo. In an aspect, the motor can include a rotary piezoelectric motor. Other non-limiting examples of motors for use in rotating the central rotatable shaft include a stepper control motor, a brushless DC commutated control motor, or a universal motor. In general, motors for use in small electronics or hand-held devices are known in the art and available from commercial sources.

Moveable Component

In some embodiments, a tissue cutting device includes a moveable component configured to move along at least a portion of the length of the central rotatable shaft. In an aspect, the moveable component is associated with a groove running along at least a portion of the length of the central rotatable shaft. For example, the central rotatable shaft (e.g., a stainless steel rod) can include a groove into which at least a portion of the moveable component is positioned, the moveable component able to move freely along the length of the groove. In an aspect, the moveable component is locked into the groove. For example, the moveable component can include a shape or an additional fitting that locks the moveable component into the groove.

FIGS. 4A-4C illustrate aspects of a central rotating shaft including a groove. FIG. 4A shows a lower portion of tissue cutting device 400 with a groove. Tissue cutting device 400 includes central rotatable shaft 410 operably connected to motor 420. Tissue cutting device 400 further includes moveable component 430 configured to move along at least a portion of the length of central rotatable shaft 410. In this example, moveable component 430 is associated with groove 450 that runs along at least a portion of the length of central rotatable shaft 410. Tissue cutting device 400 further includes elongated flexible cutting component 440 secured at a first end to moveable component 430 and at a second end to central rotatable shaft 410. FIG. 4B illustrates a cross-section (dashed line 460 of FIG. 4A) through an embodiment of tissue cutting device 400. In this example, a cross-section of tissue cutting device 400a includes central rotatable shaft 410a including groove 450a into which an appropriately shaped moveable component 430a is inserted. Also shown is at least a portion of elongated flexible cutting component 440 attached to moveable component 430a. In some embodiments, the moveable component can include a shape, e.g., an extension or flare, that allows it to stay attached to but move freely along a groove associated with the central rotatable shaft. FIG. 4C illustrates a cross-section (dashed line 460 of FIG. 4A) through another embodiment of tissue cutting device 400. In this example, a cross-section of tissue cutting device 400b includes central rotatable shaft 410b including groove 450b into which an appropriate shaped moveable component 430b is inserted. Moveable component 430b includes an extension or flare 435 that fits into an appropriately shaped portion of groove 450b. Also shown is at least a portion of elongated flexible cutting component 440 attached to moveable component 430b.

In an aspect, the moveable component is associated with a track running along at least a portion of the length of the central rotatable shaft. For example, the moveable component can be associated with a rod that runs parallel to at least a portion of the length of the central rotatable shaft. FIGS. 5A-5C illustrate aspects of a tissue cutting device including a track. FIG. 5A shows a tissue cutting device 500 with a track. Tissue cutting device 500 includes central rotatable shaft 510 operably connected to motor 520. Tissue cutting device 500 further includes moveable component 530 configured to move along at least a portion of the length of central rotatable shaft 510. In this example, moveable component 530 is associated with track 550 that runs along at least a portion of the length of central rotatable shaft 510. Tissue cutting device 500 further includes elongated flexible cutting component 540 secured at a first end to moveable component 530 and at a second end to central rotatable shaft 510. FIG. 5B illustrates a cross-section (dashed line 560 of FIG. 5A) through an embodiment of tissue cutting device 500. In this example, a cross-section of tissue cutting device 500a includes central rotatable shaft 510 including track 550. Moveable component 530a is appropriately shaped to associate with track 550. In this non-limiting example, moveable component 530a defines an opening 535 disposed over tract 550. Also shown is at least a portion of elongated flexible cutting component 540 attached to moveable component 530a.

In an aspect, the moveable component includes a fitting that allows it to stay attached to but move freely along a track associated with the central rotatable shaft. A non-limiting example of a moveable component including a fitting is shown in FIG. 5C. FIG. 5C illustrates a cross-section (560 of FIG. 5A) through an embodiment of tissue cutting device 500. In this example, a cross-section of tissue cutting device 500b includes central rotatable shaft 510 including track 550. In this non-limiting example, moveable component 530b includes fitting 570 that fits around track 550, keeping moveable component 530b attached but freely moveable. For example, fitting 570 can include a ring that is attached to the moveable component and configured to encircle the track, e.g., a rod. Also shown is at least a portion of elongated flexible cutting component 540 attached to moveable component 530a.

In an aspect, the moveable component is associated with or includes a rotatable belt, the length of which extends along at least a portion of the length of the central rotatable shaft. In an aspect, the moveable component is moved along the track by a chain, belt, or screw that turns when an operably coupled second motor is operated.

In an aspect, the moveable component is attached to a tethering component, the tethering component configured to move the moveable component along the length of the central rotatable shaft. In an aspect, the tethering component is configured to pull the moveable component along at least a portion of the length of the central rotatable shaft to change the shape formed by the elongated flexible cutting component. For example, the tethering component can include a flexible member (e.g., a wire or string) that pulls the moveable component. In an aspect, the tethering component is configured to push the moveable component along at least a portion of the length of the central rotatable shaft to change the shape formed by the elongated flexible cutting component. For example, the tethering component can include a rigid member (e.g., a rod) that pushes the moveable component.

In an aspect, the tethering component includes a tether attached to the moveable component, the tethering component configured to extend and retract the tether. In an aspect, retracting the tether uses a rotating element to wind up the tether. In an aspect, the tethering component uses a braking system to control extension and retraction of the tether. For example, the tether can be extended by releasing a brake, allowing the tether to feed out under the centrifugal force generated as the central rotatable shaft spins. The amount of tether fed out can be controlled by stopping/starting the braking system.

In an aspect, the moveable component is attached to a rod that moves up and down, pushing and/or pulling the moveable component along the length of the central rotatable shaft. For example, a small rotary motor can be used to move the rod up and down, pushing and/or pulling the moveable component and thereby changing the shape formed by the elongated flexible cutting component.

Elongated Flexible Cutting Component

A tissue cutting device includes an elongated flexible cutting component. In an aspect, the elongated flexible cutting component is attached at a first end to a moveable component. In an aspect, movement of the moveable component along at least a portion of the central rotatable shaft changes a shape formed by the elongated flexible cutting component. For example, the elongated flexible cutting component forms a D-shape that transforms in length and width as the moveable component moves along the length of the central rotatable shaft. In an aspect, the elongated flexible cutting component is at least one of a flexible wire, strand, string, fiber, thread, or ribbon.

In an aspect, the elongated flexible cutting component includes a flexible wire. In an aspect, the flexible wire includes a solid wire. In an aspect, the flexible wire includes a stranded wire. In an aspect, the flexible wire includes a braided wire. In an aspect, the flexible wire has a specific gauge or cross-sectional area. For example, the gauge of the flexible wire can be from about 2 millimeters to about 0.05 millimeters. For example, the gauge of the flexible wire can be about 2 millimeters, 1.8 millimeters, 1.6 millimeters, 1.4 millimeters, 1.2 millimeters, 1.1 millimeters, 1.0 millimeters, 0.9 millimeters, 0.8 millimeters, 0.7 millimeters, 0.6 millimeters, 0.5 millimeters, 0.45 millimeters, 0.4 millimeters, 0.36 millimeters, 0.32 millimeters, 0.3 millimeters, 0.25 millimeters, 0.23 millimeters, 0.2 millimeters, 0.18 millimeters, 0.16 millimeters, 0.14 millimeters, 0.12 millimeters, 0.11 millimeters, 0.1 millimeters, 0.09 millimeters, 0.08 millimeters, 0.07 millimeters, 0.06 millimeters, or 0.05 millimeters.

In an aspect, the elongated flexible cutting component is formed from metal. Non-limiting examples of metals suitable for forming an elongated flexible cutting component include platinum, silver, iron, copper, aluminum, and gold. In an aspect, the elongated flexible cutting component is formed from a metal alloy, e.g., stainless steel, other steel, titanium-nickel alloy, titanium-aluminum alloy, or other alloy of high resiliency. In an aspect, the elongated flexible cutting component is formed by drawing a metal, e.g., a metal alloy, through a hole in a die or draw-plate. In an aspect, the elongated flexible cutting component is formed by drawing a material, e.g., metal or polymer, through a draw-plate with a cylindrical hole. In an aspect, the elongated flexible cutting component is formed by drawing a material, e.g., metal or polymer, through a draw-plate with a non-cylindrical form, e.g., a triangle, square, pentagon, hexagon, or other multisided polygon. In an aspect, the elongated flexible cutting component is formed from at least one of natural fiber and man-made fiber. In an aspect, the elongated flexible cutting component is formed from natural fiber. For example, the elongated flexible cutting component can be formed from vegetable fiber, e.g., cotton, hemp, jute, flax, ramie, sisal, or bagasse. For example, the elongated flexible cutting component can be formed from wood fiber. For example, the elongated flexible cutting component can be formed from animal fibers, e.g., silkworm silk, spider silk, sinew, catgut, wool, sea silk, or hair. For example, the elongated flexible cutting component can be formed from mineral fibers, e.g., asbestos. In an aspect, the elongated flexible cutting component is formed from man-made fiber. For example, the elongated flexible cutting component can be formed from regenerated fibers, e.g., cellulose from wood pulp. For example, the elongated flexible cutting component can be formed from semi-synthetic fibers, e.g., nylon (polyamide), Dacron (polyester), and rayon. For example, the elongated flexible cutting component can be formed from synthetic fibers, e.g., metallic fibers, carbon fiber, boron fiber, silicon carbide fiber, fiberglass, mineral fibers, polymer fibers, and microfibers. In an aspect, the elongated flexible cutting component is formed from polymer fibers, non-limiting examples of which include polyamide nylon, PET or PBT polyester, phenol-formaldehyde, polyvinyl chloride fiber, polyolefin fibers, acrylic polyesters, aromatic polyamids, polyethylene, elastomers, polyurethane fiber, elastolefin.

In an aspect, the elongated flexible cutting component includes a monofilament line. In an aspect, the elongated flexible cutting component is formed by extruding one or more types of polymer fibers through a hole defined by a die or draw-plate. In an aspect, the elongated flexible cutting component includes a multifilament line, e.g., a braided line. In an aspect, the elongated flexible cutting component is formed from a synthetic polymer, e.g., polyethylene, by extrusion that uses a multi-pored spinneret. For example, the elongated flexible cutting component can be formed from a polymer using wet, dry, dry jet-wet, melt, gel, or electro-spinning In an aspect, the elongated flexible cutting component is formed using a gel spinning or polymer spinning process.

In an aspect, the elongated flexible cutting component includes a circular cross-section. For example, the elongated flexible cutting component can be formed by extruding a metal or polymer through a draw-plate with an appropriately sized circular hole. In an aspect, the elongated flexible cutting component includes a non-circular cross-section. In an aspect, the elongated flexible cutting component includes a polygon cross-section including three or more sides. For example, the elongated flexible cutting component can be formed by extruding a metal or polymer through a draw-plate with an appropriately sized polygon cross-section.

In an aspect, the elongated flexible cutting component includes at least one cutting edge. For example, the elongated flexible cutting component can include a ribbon with a cutting edge. For example, the elongated flexible cutting component can include a cross-sectional area, e.g., a triangular wedge, which includes a sharp edge.

In an aspect, the elongated flexible cutting component includes at least one serrated edge. For example, at least one edge of the elongated flexible cutting component can include a saw tooth design. For example, the elongated flexible cutting component can include a gigli saw wire. For example, the elongated flexible cutting component can be formed from two or more metal wires braided together to generate a serrated edge. For example, the elongated flexible cutting component can include hooks, barbs, graters, or raised bumps.

In an aspect, the elongated flexible cutting component includes at least one abrasive surface. For example, the elongated flexible cutting component can include diamond dust. For example, the elongated flexible cutting component can include at least one of silica, sand, or glass. In an aspect, the elongated flexible cutting component is treated in such a way as to have an abrasive surface, such as by sand blasting. See, e.g., U.S. Pat. No. 8,062,300 to Schmitz et al. titled "Tissue removal with at least partially flexible device," which is incorporated herein by reference.

In an aspect, the tissue cutting device includes two or more elongated flexible cutting components. In an aspect, the first ends of the two or more elongated flexible cutting components are secured to the moveable component and the second ends of the two or more elongated flexible cutting components are secure to the central rotatable shaft. In an aspect, the tissue cutting device may include a moveable component for each of the two or more elongated flexible cutting components.

In an aspect, the elongated flexible cutting component is replaceable. For example, the elongated flexible cutting component may be secured to the moveable component and/or the central rotatable shaft with a reversible attachment component, e.g., a screw, a clamp, a crimp, or the like. In an aspect, the elongated flexible cutting component is supplied as a single unit. For example, the elongated flexible cutting component may be supplied as single strands or ribbons, the first end of which is configured to attach to a moveable component and the second end of which is configured to attach to the central rotatable shaft. In an aspect, the elongated flexible cutting component is supplied as a multiunit supply. For example, the multiunit supply may include a length of elongated flexible cutting component that can be cut/reattached to replace used, contaminated, and/or broken elongated flexible cutting component.

In an aspect, the elongated flexible cutting component is included in a replaceable cartridge. In an aspect, a single unit of elongated flexible cutting component is included in a replaceable cartridge. In an aspect, a multiunit supply of elongated flexible cutting component is included in a replaceable cartridge. For example, the elongated flexible cutting component may be included in a replaceable cartridge that attaches to the tissue cutting device. For example, the elongated flexible cutting component may be fed out from one end of a cartridge to attach to either the moveable component or the second end of the central rotatable shaft. For example, a replaceable cartridge, e.g., a spool, including a reserve of the elongated flexible cutting component may be associated with central rotatable shaft or the moveable component. In an aspect, the replaceable cartridge including a source of the elongated flexible cutting component is incorporated into the moveable component. In an aspect, the replaceable cartridge including a source of the elongated flexible cutting component is incorporated into the central rotatable shaft. In an aspect, the replaceable cartridge including the elongated flexible cutting component is disposed in a lumen defined by the central rotatable shaft, the replaceable cartridge configured to allow the elongated flexible cutting component to be fed out the central rotatable shaft and secured to the moveable component.

Aspiration Component

In an aspect, the tissue cutting device includes an aspiration component configured to aspirate tissue debris in proximity to the central rotatable shaft. In an aspect, the aspiration component includes a vacuum source and an aspirator connected to the vacuum source. For example, the tissue cutting device can include and aspiration component to aspirate tissue debris created during tissue cutting with the rotating elongated flexible cutting component of the tissue cutting device.

Figure 6:
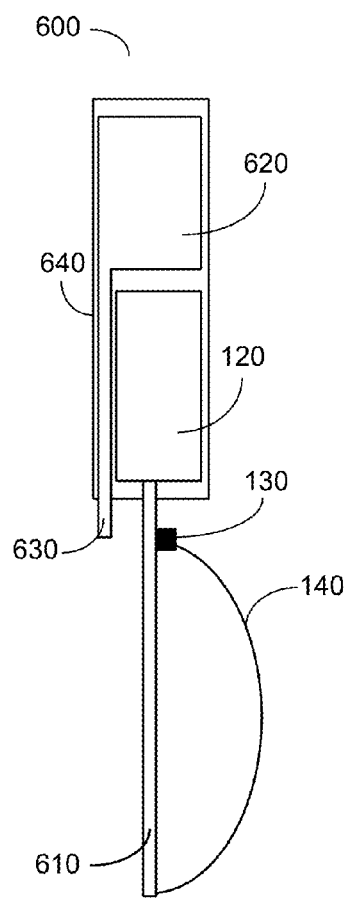
FIG. 6 is a schematic of a tissue cutting device including an aspiration component.

In an aspect, the aspirator includes a suction tube positioned proximal to the central rotatable shaft, the suction tube connected to the vacuum source. FIG. 6 illustrates a non-limiting embodiment of a tissue cutting device including a suction tube. FIG. 6 shows tissue cutting device 600 including central rotatable shaft 610 operably coupled to motor 120. Elongated flexible cutting component 140 is shown attached at a first end to moveable component 130 and at a second end to central rotatable shaft 610. Tissue cutting device 600 further includes vacuum source 620. Vacuum source 620 is in fluid communication with suction tube 630. Suction tube 630 extends from handle casing 640 into a region in proximity to central rotatable shaft 610 and is configured to aspirate tissue debris resected by the rotating elongated flexible cutting component 140.

Figure 7:
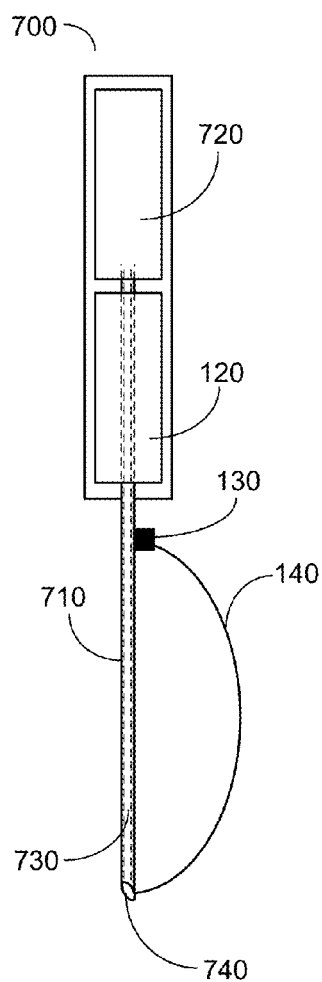
FIG. 7 is a schematic of a tissue cutting device including an aspiration component.

In an aspect, the aspirator includes a suction lumen disposed in and defined by the central rotatable shaft, the suction lumen connected to the vacuum source and in fluid communication with one or more openings defined by the central rotatable shaft. In an aspect, the one or more openings defined by the central rotatable shaft include a single opening. For example, the one opening can be positioned at or near the end of the central rotatable shaft. FIG. 7 illustrates a non-limiting embodiment of a tissue cutting device including a suction lumen and one opening defined by the central rotatable shaft. FIG. 7 shows tissue cutting device 700 including central rotatable shaft 710 operably coupled to motor 120. Elongated flexible cutting component 140 is shown attached at a first end to moveable component 130 and at a second end to central rotatable shaft 710. Tissue cutting device 700 further includes vacuum source 720. Central rotatable shaft 710 further includes a suction lumen 730 disposed in and defined by central rotatable shaft 710. Suction lumen 730 is connected to vacuum source 720 and is in fluid communication with an opening 740 defined by central rotatable shaft 710. In this non-limiting embodiment, tissue cutting device 700 is configured to aspirate tissue debris generated by the rotation of elongated flexible cutting component 140 into opening 740, aspirate the debris through suction lumen 730, and into vacuum source 720.

Figure 8:
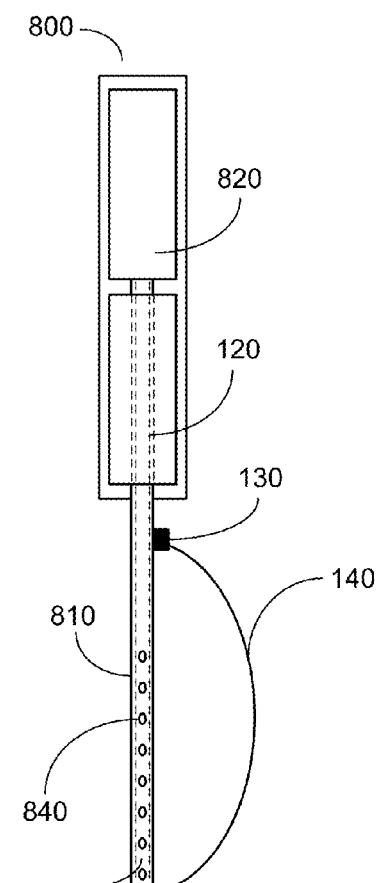
FIG. 8 is a schematic of a tissue cutting device including an aspiration component.

In an aspect, the one or more openings defined by the central rotatable shaft are positioned along the length of the central rotatable shaft. For example, the tissue cutting device can include a single opening somewhere along the length of the central rotatable shaft. For example, the tissue cutting device can include a plurality of openings positioned along the length of the central rotatable shaft. FIG. 8 illustrates a non-limiting embodiment of a tissue cutting device including a suction lumen and a plurality of openings defined by the central rotatable shaft. FIG. 8 shows tissue cutting device 800 including central rotatable shaft 810 operably connected to motor 120. Elongated flexible cutting component 140 is attached at a first end to moveable component 130 and at a second end to central rotatable shaft 810. Tissue cutting device 800 further includes vacuum source 820. Central rotatable shaft 810 further includes a suction lumen 830 disposed in and defined by central rotatable shaft 810. Suction lumen 830 is connected to vacuum source 820 and is in fluid communication with openings 840 defined by and positioned along the length of central rotatable shaft 810. In this non-limiting embodiment, tissue cutting device 800 is configured to aspirate tissue debris generated by the rotation of elongated flexible cutting component 140 into openings 840, aspirate the debris through suction lumen 830, and into vacuum source 820.

In an aspect, the vacuum source is at least partially contained within a hand-held housing of the tissue cutting device. For example, vacuum source can include any of a number of small, commercially available mini vacuum pumps sized for use in small appliances (from, e.g., Vaccon Co, Inc., Medway, Mass.; Hargraves Technology Corp, Mooresville, N.C.). In an aspect, the vacuum source is external to the tissue cutting device, e.g., a large vacuum pump, but connected, e.g., by a fitting, luer, or connection, to the aspirator through a vacuum conduit, e.g., a hose or tubing. In an aspect, the external vacuum source includes an aspirator pump, e.g., a water aspirator.

In an aspect, the tissue cutting device further includes a tissue debris reservoir. In an aspect, the tissue debris reservoir includes a space (e.g., a receptacle) defined by the tissue cutting device and is configured to hold tissue debris aspirated by the aspiration component. In an aspect, the tissue debris reservoir is positioned along the flow path of the aspiration component. For example, a tissue debris reservoir can be positioned along the path of the aspirator. In an aspect, the tissue debris reservoir is accessible to a user. For example, resected tissue can be collected in the tissue debris reservoir and removed for analysis following a cutting procedure to assess disease presence and/or progression (e.g., benign versus malignant pathology).

Figure 9:
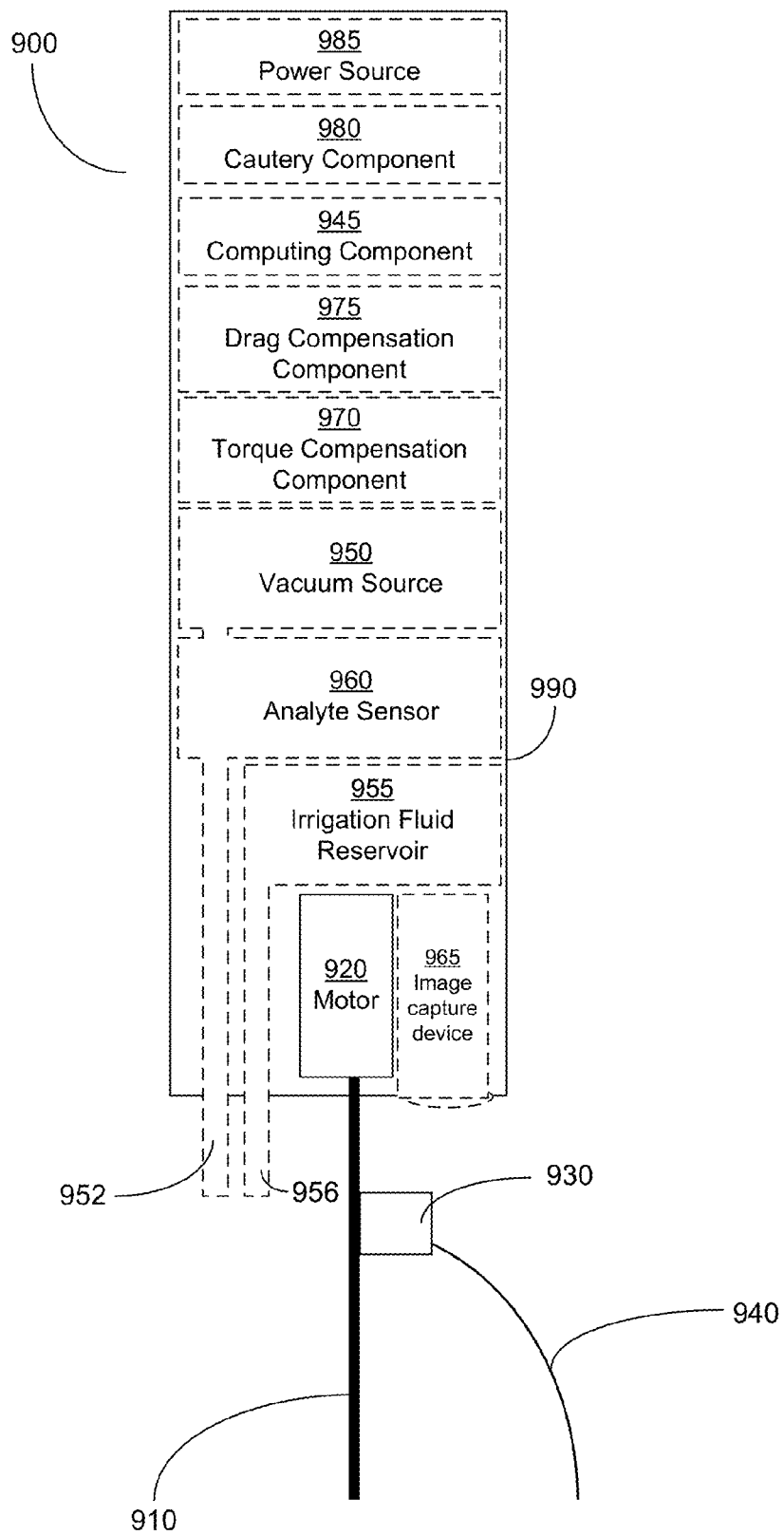
FIG. 9 illustrates further aspects of a tissue cutting device.

FIG. 9 illustrates further non-limiting aspects of a tissue cutting device. FIG. 9 shows tissue cutting device 900 including central rotatable shaft 910 operably connected at a first end to motor 920. Motor 920 includes circuitry configured to rotate central rotatable shaft 910. Elongated flexible cutting component 940 is secured at a first end to moveable component 930 and at a second end to the central rotatable shaft 910. Moveable component 930 is configured to move along at least a portion of the length of central rotatable shaft 910. Movement of moveable component 930 along the at least a portion of the length of central rotatable shaft 910 changes a shape formed by elongated flexible cutting component 940.

In an aspect, tissue cutting device 900 includes a computing component 945 operably coupled to at least one of the motor 920 and the moveable component 930. In an aspect, computing component 945 includes circuitry configured to control motor 920. In an aspect, computing component 945 includes circuitry configured to control moveable component 930.

In some embodiments, tissue cutting device 900 includes an aspiration component configured to aspirate tissue debris in proximity to central rotatable shaft 910. The aspiration component includes vacuum source 950 and an aspirator 952 connected to vacuum source 950. In some embodiments, tissue cutting device includes at least one analyte sensor 960 configured to sense a property of one or more analytes in an aspirate. In some embodiments, tissue cutting device 900 includes an irrigation component configured to irrigate tissue in proximity to the central rotatable shaft. In an aspect, the irrigation component includes a flow conduit 956 attached to an irrigation fluid reservoir 955. In an aspect, irrigation fluid reservoir 955 is configured to hold and controllably release at least one irrigation fluid. In some embodiments, a tissue cutting device includes an aspiration component and an irrigation component.

In some embodiments, tissue cutting device 900 includes an image-capture device 965. In an aspect, image-capture device 965 is operably coupled to computing component 945. In an aspect, computing component 945 includes circuitry configured to receive one or more images from image-capture device 965. In some embodiments, tissue cutting device 900 includes a torque compensation component 970, the torque compensation component including circuitry configured to prevent axial oscillation when performing asymmetric cutting patterns. In some embodiments, tissue cutting device 900 includes a drag compensation component 975, the drag compensation component including circuitry configured to measure resistance from the elongated flexible cutting component during rotation and to adjust a rotational speed. In some embodiments, tissue cutting device 900 includes a cautery component 980, the cautery component configured to cauterize tissue during a cutting process. In an aspect, the tissue cutting device 900 includes a power source 985. In an aspect, tissue cutting device 900 further includes a handle casing 990.

Computing Component

In an aspect, a tissue cutting device includes a computing component. In an aspect, the computing component includes a processor. In an aspect, the computing component is operably connected to one or more components of the tissue cutting device. In an aspect, the computing component includes circuitry configured to control the function of one or more components of the tissue cutting device. In an aspect, the computing component includes circuitry to execute one or more instructions for controlling one or more functions of one or more components of the tissue cutting device. In an aspect, the computing component is operably coupled to at least one of the motor and the moveable component. In an aspect, the computing component includes circuitry configured to control the motor. For example, the computing component can include circuitry configured to control an on/off function of the motor and/or the rotational frequency of the motor. In an aspect, the computing component is operably coupled to a second motor (e.g., a motor associated with a tethering component). In an aspect, the computing component includes circuitry configured to control the moveable component. For example, the computing component can control an on/off function of the moveable component. For example, the computing component can control at least one of speed of the moveable component, directionality of the moveable component, and distance traveled by the moveable component. In an aspect, the computing component includes circuitry configured to control movement of the moveable component in coordination with rotational speed of the central rotatable shaft and associated elongated flexible cutting component to generate an asymmetric cutting pattern.

In an aspect, the computing component is operably coupled to other components of the tissue cutting device, non-limiting examples of which include an aspiration component, an irrigation component, an image-capture device, at least one analyte sensor, a torque compensation component, a drag compensation component, and/or a cautery component. In an aspect, the computing component includes circuitry configured to control one or more functions of an aspiration component, an irrigation component, an image-capture device, at least one analyte sensor, a torque compensation component, a drag compensation component, and/or a cautery component associated with the tissue cutting device.

In an aspect, the computing component includes a microprocessor, e.g., a central processing unit, for controlling one or more functions of one or more components of the tissue cutting device. The computing component further includes a system memory and a system bus that couples various system components including the system memory to the microprocessor. The microprocessor can include a processing unit, a central processing unit (CPU), a digital signal processor (DSP), an application-specific integrated circuit (ASIC), a field programmable gate entry (FPGA), or the like, or any combinations thereof, and can include discrete digital or analog circuit elements or electronics, or combinations thereof. In an aspect, the computing component includes one or more ASICs having a plurality of predefined logic components. In an aspect, the component includes one or more FPGA having a plurality of programmable logic commands.

In some embodiments, the computing component is connected to a user interface, e.g., one or more input components and/or output components for use by a user to interface with the tissue cutting device. The one or more input components can be used to enter information into the tissue cutting device, e.g., rotational frequency of the motor and/or rate and distance movement of the moveable component, and may be integrated into the tissue cutting device or may be one or more peripheral devices operably connected through a wired or wireless connection to the tissue cutting device. Non-limiting examples of input components include a graphical user interface, a display, a keyboard, a keypad, a touch-screen, a microphone, a stylus pen, a switch, a dial, or the like. In some embodiments, the user interface is user driven. For example, the user inputs data or operating conditions into the tissue cutting device using the user interface, e.g., a touch-screen. In some embodiments, the user interface, e.g., a switch, is circuitry driven. For example, an on/off switch may be toggled based on proximity of a portion of the tissue cutting device, e.g., the central rotatable shaft, to the skin surface of an individual.

In an aspect, the user interface can include one or more output components over which processed information is viewed as output results and may be integrated into the tissue cutting device or may be one or more peripheral devices operably connected through a wired or wireless connection to the tissue cutting device. For example, the user interface may be used to report to a user one or more of a speed of rotation, a rate/distance, a shape formed by the elongated flexible cutting component, an identity of sensed analyte, one or more images captured by an image-captured device, drag compensation, torque compensation, tissue resection pattern, and the like. Non-limiting examples of output components include but are not limited to television screens, computer monitors, liquid crystal displays, audio speakers, audio headphones, and printers.

In an aspect, the one or more input/output components are connected to the microprocessor of the computing component through one or more user input interfaces that are coupled to the system bus, but may be connected by other interfaces and bus structures, such as a parallel port, game port, or a universal serial bus (USB). For example, external input components or output components may be connected to the microprocessor through a USB port. The computing component may further include or be capable of connecting to a flash card memory. The computing component may further include or be capable of connecting with a network through a network port and network interface, and through wireless port and corresponding wireless interface may be provided to facilitate communication with other peripheral devices, for example, a smart phone, a computer, a display monitor, and/or a printer.

In an aspect, the computing component is operably coupled to a transmission unit. A "transmission unit," as used herein, can be one or more of a variety of units that are configured to send and/or receive signals, such as signals carried as electromagnetic waves. A transmission unit generally includes at least one antenna and associated circuitry. A transmission unit can include a transmitter and a receiver. A transmission unit can include volatile or non-volatile memory. A transmission unit can include a processor and/or be operably connected to a processor. A transmission unit can be operably connected to an energy source, such as a battery. A transmission unit can include an energy harvesting unit, such as a unit configured to obtain energy from electromagnetic waves. A transmission unit can include a transponder utilizing electromagnetic waves, for example as described in "Fundamental Operating Principles," in Chapter 3 of the *RFID Handbook: Fundamentals and Applications in Contactless Smart Cards and Identification*, Klaus Finkenzeller, John Wiley & Sons, (2003), which is incorporated herein by reference. A transmission unit can include an oscillator and encoder configured to generate a programmable pulse position-modulated signal in the radio frequency range (see, e.g., U.S. Pat. No. 4,384,288, which is incorporated herein by reference). A transmission unit can include a radio frequency identification device (RFID), which can be a passive RFID device, a semi-passive RFID device, or an active RFID device, depending on the embodiment (see, e.g., Chawla & Ha, "An Overview of Passive RFID," *IEEE Applications and Practice*, 11-17 (September 2007), which is incorporated herein by reference). A transmission unit including an RFID device can be configured to transmit signals in the UHF standard range. A transmission unit can include a battery-assisted passive RFID device, such as sold by Alien Technology®, Morgan Hill, Calif. A transmission unit can include an optical transmission unit. A transmission unit can include a hybrid backscatter system configured to function in an RFID, IEEE 802.11x standard and Bluetooth system (see, e.g., U.S. Pat. No. 7,215,976, which is incorporated herein by reference). A transmission unit can include a near field communication (NFC) device. A transmission unit can include a Wireless Identification and Sensing Platform (WISP) device.

In an aspect, image-based applications such as viewers and/or toolkits (e.g., Insight Segmentation and Registration Toolkit (ITK)), are incorporated for further intake of information. In an aspect, CAD implementations, image segmentation, or other image analysis algorithms may allow processing of images received from an image-capture device and/or from at least one analyte sensor.

The computing component can further include memory chips, e.g., ROM or flash memory chips, for providing storage of operating systems, look-up tables, and algorithms for comparing input data with reference data. The system memory of the computing component may include read-only memory (ROM) and random access memory (RAM). A number of program modules may be stored in the ROM or RAM, including an operating system, one or more application programs, other program modules and program data.

The computing component includes computer-readable media products and may include any media that can be accessed by the computing component including both volatile and nonvolatile media, removable and non-removable media. By way of example, and not of limitation, computer-readable media may include non-transitory signal-bearing media. Non-limiting examples of non-transitory signal-bearing media include a recordable type medium such as magnetic tape, a hard disk drive, digital tape, computer memory, or the like, as well as transmission type medium such as a digital and/or analog communication medium (e.g., fiber optic cable, waveguide, wired communications link, wireless communication link). Further non-limiting examples of signal-bearing media include, but are not limited to, flash memory, magnetic tape, MINIDISC, non-volatile memory card, EEPROM, optical disk, optical storage, RAM, ROM, system memory, web server, cloud, or the like. By way of example, and not of limitation, computer-readable media may include computer storage media, e.g., magnetic tape, magnetic disk storage, optical disk storage, memory cards, flash memory cards, electrically erasable programmable read-only memory (EEPROM), solid state RAM, and solid state ROM or any other medium which can be used to store the desired information and which can be accessed by the computing component. By way of further example, and not of limitation, computer-readable media may include a communication media, e.g., wired media, such as a wired network and a direct-wired connection, and wireless media such as acoustic, RF, optical, and infrared media.

Irrigation Component

In some embodiments, as shown in FIG. 9, a tissue cutting device includes an irrigation component configured to irrigate tissue in proximity to the central rotatable shaft, the irrigation component including a flow conduit attached to an irrigation fluid reservoir. In an aspect, the irrigation fluid reservoir is configured to hold and controllably release at least one irrigation fluid. In an aspect, the irrigation fluid reservoir is operably coupled to a computing component, the computing component including circuitry configured to control release of at least one irrigation fluid. In some embodiments, the flow conduit includes an irrigation tube positioned in proximity to the central rotatable shaft, the irrigation tube connected to the irrigation fluid reservoir. For example, the tissue cutting device can include an irrigation fluid reservoir holding at least one irrigation fluid and an irrigation tube extending from the irrigation fluid reservoir to a location in proximity to the central rotatable shaft. In some embodiments, the flow conduit includes an irrigation lumen disposed in and defined by the central rotatable shaft, the irrigation lumen connected to the irrigation fluid reservoir and in fluid communication with one or more openings defined by the central rotatable shaft. For example, the central rotatable shaft can include an irrigation lumen that runs along at least a portion of the inner length of the central rotatable shaft with an opening at the second end of the central rotatable shaft from which an irrigation fluid is expelled. In an aspect, the irrigation tube is in fluid communication with one or more openings defined by the central rotatable shaft. For example, the central rotatable shaft can include one or more openings, e.g., pores, through the irrigation fluid is expelled.

In an aspect, the irrigation fluid reservoir is configured to hold and controllably release at least one irrigation fluid. In an aspect, the at least one irrigation fluid helps to fluidize the resected tissue. In an aspect, the at least one irrigation fluid treats a condition of the remaining tissue. For example, the irrigation fluid can include one or more components to prevent infection (e.g., one or more antimicrobial agents). For example, the irrigation fluid can include one or more components to treat a malignancy (e.g., one or more chemotherapy agents). In an aspect, the at least one irrigation fluid includes at least one of saline, a buffer, a therapeutic agent, an antimicrobial agent, an anesthetic, or a coagulant agent. In an aspect, the at least one irrigation fluid includes saline, the saline used to irrigate the tissue before, during, and/or after resection of tissue with the rotating elongated flexible cutting component. For example, the irrigation fluid can include a physiological sodium chloride salt solution. In an aspect, the at least one irrigation fluid includes a buffer. For example, the at least one irrigation fluid can include a buffer to maintain a physiological pH before, during, and/or after a cutting procedure. For example, the at least one irrigation fluid can include a buffer to maintain a pH above or below a physiological pH before, during, and/or after a cutting procedure. In an aspect, the at least one irrigation fluid includes a buffer, the buffer used to irrigate the tissue before, during, and/or after resection of tissue with the rotating elongated flexible cutting component. For example, the buffer can include phosphate buffered saline.

In an aspect, the irrigation fluid includes at least one therapeutic agent, the at least one therapeutic agent added to the tissue before, during, and/or after cutting of tissue with the rotating elongated flexible cutting component. For example, the at least one irrigation fluid can include an anti-inflammatory agent, non-limiting examples of which include dexamethasone, prednisolone, corticoserone, budesonide, estrogen, sulfasalazine, and mesalamine. For example, the at least one irrigation fluid can include a chemotherapeutic agent, added before, during, and/or after resection of tissue with the rotating elongated flexible cutting component. Non-limiting examples of chemotherapy agents include alkylating agents (e.g., nitrosoureas, tetrazines, aziridines, cisplatin, procarbazine, and hexamethylmelamine), anti-metabolites (e.g., methotrexate, pemetrexed, fluorouracil, capecitabine, gemcitabine, decitabine, and pentostatin), anti-microtubule agents (e.g., vinca alkaloid and taxanes), topoisomerase inhibitors (e.g., irinotecan, topotecan, eoposide, doxorubicin, and teniposide), and cytotoxic antibiotics (e.g., anthracyclines, actinomycin, bleomycin, plicamycin, and mitomycin.

In an aspect, the irrigation fluid includes at least one antimicrobial agent, the at least one antimicrobial agent added to the tissue before, during, and/or after resection of tissue with the rotating elongated flexible cutting component. For example, the at least one irrigation fluid can include one or more antibiotics added to a region of tissue before, during, and/or after the elongated flexible cutting component is resecting tissue pieces to prevent bacterial infection at the cutting site. Non-limiting examples of antibiotics used prophylactically for surgical procedures include ampicillin, aztreonam, cefazolin, cefuroxime, cefotaxime, cefoxitin, cefotetan, ceftriaxone, ciprofloxacin, clindamycin, ertapenem, fluconazole, gentamicin, levofloxacin, metronidazole, moxifloxacin, piperacillin-tazobactam, and vancomycin.

In an aspect, the at least one irrigation fluid includes an anticoagulant agent. For example, at least one anticoagulant can be added before and/or during the cutting procedure to prevent blood clotting and aide in tissue removal. Non-limiting examples of anticoagulant agents include antithrombotic agent such as, for example, heparin, heparin derivatives, urokinase, platelet inhibitors, hirudin, and dextrophenylalanine praline arginine chloromethylketone (Ppack).

In an aspect, the at least one irrigation fluid includes a coagulant agent. For example, at least one coagulant agent can be added before, during, and/or after the cutting procedure to reduce or stop bleeding. For example, the at least one irrigation fluid can include adding one or more coagulant agents, e.g., zeolites, thrombin, or fibrin glue, before, during, and/or after the elongated flexible cutting component is resecting tissue pieces. Other non-limiting examples of coagulant agents include aminocaproic acid, confugated estrogen, desmopressin, plasma, factor 7A, phytonadione, protamine, prothrombin complex, or tranexamic acid.

In an aspect, the at least one irrigation fluid includes an anesthetic agent. Non-limiting examples of anesthetic agents include lidocaine, bupivacaine, and ropivacaine. In an aspect, the at least one irrigation fluid includes an analgesic agent. Non-limiting examples of analgesic agents include opioid analgesics (e.g., codeine, fentanyl, meperidine, methadone, morphine, pentazocine, and tramadol) and non-opioid analgesics (e.g., etodolac, fenoprofen, ketoprofen, ketorolac, paracetamol, aspirin, diclofenac, ibuprofen, indomethacin, and naproxen.

In an aspect, the irrigation component includes at least one controllable valve, the at least one controllable valve operably coupled to a computing component. For example, the controllable valve can include a controllable gate, door, port, diaphragm, erodible barrier, or any other type of controllable valve configured to hold and controllably release at least one irrigation fluid from the irrigation component. In an aspect, the at least one controllable valve is associated with the irrigation fluid reservoir. In an aspect, the at least one controllable valve is associated with the flow conduit.

In some embodiments, a tissue cutting device includes an aspiration component and an irrigation component. In an aspect, the aspiration component and the irrigation component function simultaneously. For example, the aspiration component may be aspirating tissue debris at the same time the irrigation component is providing an irrigation fluid. In an aspect, the aspiration component and the irrigation component are functioning sequentially. For example, the irrigation component may provide an irrigation fluid (e.g., saline or a buffer) followed by the aspiration component aspirating the irrigation fluid in combination with associated tissue debris. For example, the aspiration component may aspirate tissue debris from a tissue site followed by irrigation of the tissue site with an irrigation fluid (e.g., a coagulant to stop bleeding, a neoplastic agent to kill any remaining cancerous cells, or an antibiotic to prevent infection post tissue resection).

Image-Capture Device

In some embodiments, as shown in FIG. 9, a tissue cutting device includes an image-capture device. In an aspect, the image-capture device is used to guide a tissue cutting procedure. For example, imaging guidance can be used to determine the location of the tissue to be removed and to monitor removal of tissue during the tissue cutting procedure. In an aspect, the image-capture device is operably coupled to a computing component, the computing component including circuitry configured to receive one or more images from the image-capture device. In an aspect, the image-capture device is configured to capture one or more images of the tissue during the resection process. In an aspect, the image-capture device is configured to capture one or more images to document the progress of the resection process. For example, the images capture device can capture one or more images to document how much target tissue remains, the shape of the remaining target tissue, the pathology of the remaining target tissue, other targets or off-targets in the resection field. For example, the image-capture device can capture one or more images of blood vessels and/or nerves that might confound the resection process. In an aspect, the computing component includes circuitry configured to alter a function of one or more other components of the tissue cutting device in response to the received one or more images from the image-capture device. For example, the computing component can include circuitry configured to alter a function of at least one of the motor and the moveable component to change a shape formed by the elongated flexible cutting component in response to the received one or more images. For example, the computing component can include circuitry configured to alter a function of an aspiration component, an irrigation component, at least one analyte sensor, and/or the cautery component in response to the received one or more images.

In an aspect, the one or more images captured with the image-capture device are representative of one or more properties of the tissue or its constituents (e.g., cells, blood vessels, nerves, connective tissue, adipose tissue, and the like). The one or more properties can include one or more inherent properties or characteristics of the tissue or its constituents that are measureable by the image-capture device. In an aspect, the one or more properties of the tissue or its constituents can include at least one of an optical property, autofluorescence property, an infrared spectral property, a reflective property, a light scattering property, or an opacity property of the tissue. In an aspect, the one or more properties of the tissue or its constituents can include one or more of a size, a morphological property, or a physical feature of the tissue or its constituents.

In an aspect, the image-capture device includes an optical image-capture device. For example, the image-capture device can include a camera for capturing photographic images of the tissue. For example, the image-capture device can include components of a laparoscope, e.g., a telescopic rod lens system connected to a video camera. For example, the image-capture device can include a miniature digital video camera, e.g., a charge-coupled device, located at or near the end of the tissue cutting device. In an aspect, the image-capture device further includes a light source, e.g., a fiber optic cable connected to a light source (e.g., halogen or xenon) to illuminate the field for capturing images.

In an aspect, the optical image-capture device includes circuitry configured to capture one or more images in at least one of ultraviolet, visible, or infrared wavelengths. In an aspect, the optical image-capture device includes circuitry configured to capture one or more images of fluorescence emitted from the tissue during the resection process. In an aspect, the optical image-capture device includes circuitry configured to capture one or more images of autofluorescence emitted from the tissue during the resection process. In an aspect, an autofluroescence signal emitted from a tissue during the resection process includes an autofluorescence signal emitted by a normal tissue or an abnormal tissue, e.g., a cancerous or diseased tissue. In an aspect, the optical image-capture device includes circuitry configured to capture one or more images of fluorescence emitted from one or more fluorescing agents associated with the tissue. For example, a fluorescing agent that specifically binds cancerous cells or other diseased cells can be given to a subject prior to the cutting procedure to fluorescently mark the cancerous cells or other diseased cells. For example, a fluorescing agent that specifically binds cancerous cells or other diseased cells can be applied to the tissue during the cutting procedure.

In an aspect, the image-capture device is configured to capture one or more signals emitted from the tissue before, during, and/or after the resection process. In an aspect, the one or more signals include one or more optical signals, one or more fluorescence signals, one or more acoustic signals, one or more electrical signals, one or more magnetic signals, one or more radiofrequency signals, or one or more electromagnetic signals. In an aspect, the image-capture device uses any of a number of imaging or optical methods including but not limited to light scattering, electrical impedance, infrared spectroscopy, acoustic imaging, thermal imaging, photothermal imaging, dark field, visible light absorption and refraction, and autofluorescence. In an aspect, the image-capture device measures the absorption, emission, fluorescence, luminescence, chemiluminescence, and/or phosphorescence from the tissue.

In an aspect, the image-capture device includes at least one camera, e.g., a digital camera, configured to capture one or more images. In an aspect, the at least one camera may capture one or more images in the visible spectrum. In an aspect, the at least one camera may capture one or more images in other portions of the electromagnetic spectrum, e.g., infrared or ultraviolet. In an aspect, the at least one camera may capture emitted and/or reflected light. The image-capture device can include one or more electronic image sensors, e.g., photodiodes, photoresistors, charge-coupled devices (CCD), and/or complementary metal oxide semiconductor (CMOS) devices. In an aspect, the image-capture device includes a single-shot capture device with one CCD with a Bayer filter mosaic or three separate image sensors, which are exposed to the same image via a beam splitter. In an aspect, the image-capture device includes a multi-shot capture device. For example, a single CCD sensor may obtain additive color information by capturing an image three times, each with a different filter (e.g., red, green, and blue). For example, the CCD sensor may capture images as it is moved to various locations on the focal plane and a high resolution composite image "stitched" together. In an aspect, the image-capture device includes a scanning device in which the sensor moves across the focal plane. For example, the camera can include a rotating line camera with a linear CCD array to assemble a high resolution digital image as the camera rotates. Camera can include an area array of CCD or CMOS sensors. Camera can include a linear array of CCD (monochrome) or 3-strip CCD with color filters.

In an aspect, the image-capture device includes an ultrasound image-capture device. In an aspect, the ultrasound image-capture device produces sounds waves, receives echoes from said sound waves, and/or interprets the echoes. In an aspect, the ultrasound image-capture device uses continuous waves. In an aspect, the ultrasound image-capture device uses pulsed waves. In an aspect, the ultrasound image-capture device uses frequencies of about 1 megahertz to about 18 megahertz. In some embodiments, lower or higher frequencies are used. In some embodiments, the ultrasound image-capture device includes a piezoelectric transducer or a capacitive micromachined transducer. In an aspect, the ultrasound image-capture device uses one or more modes. For example, the ultrasound image-capture device can use one or more of A-mode, B-mode/2D mode, C-mode, M-mode, Doppler mode, pulse inversion mode, and/or harmonic mode. In an aspect, the ultrasound image-capture device includes a transducer and a low frequency transmitter for ultrasound elasticity imaging. For example, the ultrasound image-capture device may include a transducer for imaging a tissue region over time while the low frequency transmitter is used to perturb and oscillate the tissue region. Under these conditions, healthy tissue will oscillate differently than unhealthy tissue. In an aspect, the ultrasound image-capture device includes one or more features of a hand-held ultrasound image-capture device. See, e.g., U.S. Pat. No. 8,128,568 to Wang et al. titled "Handheld volumetric ultrasound scanning device;" and U.S. Pat. No. 8,808,295 to Vercellotti et al. titled "Insert for a handheld ultrasound surgical device;" which are incorporated herein by reference.

In an aspect, the image-capture device includes one or more imaging sensors including, but not limited to, one or more piezo transducers, one or more MEMS device, one or more cavity resonators, one or more magneto resistive sensors, one or more magnetic field sensors, and/or one or more thermal sensors. In an aspect, the image-capture device includes one or more electromagnetic energy sensors, one or more acoustic sensors, one or more photodetectors, one or more radiofrequency antennae, one or more magnetic energy sensors, one or more thermal sensors, and/or one or more electrical energy sensors. The one or more electromagnetic energy sensors can include one or more optical sensors including, but not limit to, sensors configured to detect near infrared, ultraviolet, fluorescence, and/or visual light emitted from the tissue.

Analyte Sensor

In some embodiments, as shown in FIG. 9, a tissue cutting device includes at least one analyte sensor. In an aspect, the at least one analyte sensor includes at least one of an optical sensor, a magnetic sensor, an electrical sensor, an acoustic sensor, or a chemical sensor. In an aspect, the at least one analyte sensor is configured to sense a property of one or more analytes in an aspirate. For example, the at least one analyte sensor can be used to determine whether the aspirate, e.g., tissue debris, contains disease-associated analytes, e.g., disease-associated molecules or cells. For example, the at least one analyte sensor can be used to determine whether the aspirate contains tumor markers or cancerous cells. In an aspect, the at least one analyte sensor is configured to sense an optical property, fluorescence property, magnetic property, electrical property, electromagnetic property, acoustic property, or chemical property of the one or more analytes in the aspirate. In an aspect, the at least one analyte sensor is operably coupled to a computing component, the computing component including circuitry configured to receive an input from the at least one analyte sensor and to adjust the function of at least one component of the tissue cutting device in response to the received input. For example, the computing component trigger movement of the moveable component to change the shape formed by the elongated flexible cutting component in response to detecting the presence of neoplastic cells at the margins of the resected tissue.

In an aspect, the at least one analyte sensor includes at least one piezo transducer, MEMS device, cavity resonator, magneto resistive sensor, magnetic field sensors, and/or thermal sensor. In an aspect, the at least one analyte sensor includes one or more electromagnetic energy sensors, one or more acoustic sensors, one or more photodetectors, one or more radiofrequency antennae, one or more magnetic energy sensors, one or more thermal sensors, and/or one or more electrical energy sensors. The one or more electromagnetic energy sensors can include one or more optical sensors including, but not limit to, sensors configured to detect near infrared, ultraviolet, fluorescence, and/or visual light.

In an aspect, the at least one analyte sensor is configured to sense an inherent property of one or more analytes in an aspirate. In an aspect, the one or more analytes can include one or more cell types (e.g., blood cells, organ cells, connective tissue cells, nerve cells, neoplastic cells, diseased cells, and the like) in the aspirate.

In an aspect, the one or more analytes can include one or more biomolecules (e.g., proteins, lipids, nucleotides, and polysaccharides) in the aspirate. For example, the one or more analytes can include one or more types of biomolecules found in the tissue milieu. For example, the one or more analytes can include one or more types of biomolecules released from the tissue cells during the cutting procedure. For example, the at least one analyte sensor can be configured to sense an inherent property of a biomolecule or a cell. For example, the at least one analyte sensor can be configured to sense an inherent autofluorescence property of a biomolecule or a cell. For example, the at least one analyte sensor can be configured to sense an inherent chemical property of a biomolecule.

In an aspect, the at least one analyte sensor is configured to sense a property of one or more signaling agents interacting with one or more analytes in an aspirate. For example, one or more signaling agents designed to recognize and/or interact with diseased cells and/or biomolecules can be added before and/or during a cutting and aspiration procedure. The one or more signaling agents can include one or more antibodies, aptamers, ligands, receptors, oligonucleotides or other binding agents labeled with a marker (e.g., an optical, fluorescent, acoustic, magnetic, radioactive, RFID tag, or chemical marker) that can be detected by the at least one analyte sensor. For example, a fluorescently labeled antibody designed to recognize and bind a tumor cell marker can be added before and/or during a tumor resection procedure and detected in an aspirate with the at least one analyte sensor.

In an aspect, the at least one analyte sensor is configured to sense one or more cell types. In an aspect, the at least one analyte sensor is configured to sense a physical property of a cell, e.g., cell size, deformability, compressibility, shape, density, surface properties, electrical polarizability, magnetic susceptibility, and/or refractive index. For example, circulating tumor cells can be distinguished from red blood cells and/or white blood cells based on the relatively larger size of circulating tumor cells. In an aspect, the at least one analyte sensor is configured to sense one or more cell types by recognizing one or more cell-associated biomolecules with a binding agent, e.g., an antibody, aptamer, or oligonucleotide. For example, a target cell, e.g., a cancer cell, can be captured using an antibody that recognizes and binds to a cancer-specific cell marker. In an aspect, the at least one analyte sensor is configured to sense cancerous cell types. For example, the at least one analyte sensor can be configured to sense a cancerous cell type. For example, the at least one analyte sensor can be configured to sense a normal cell type.

In an aspect, the at least one analyte sensor is configured to sense a disease marker. For example, the at least one analyte sensor can be configured to sense a disease marker of diabetes, a metabolic disorder, a cardiovascular disease, a neurological disease, an inflammatory disease, a gastrointestinal disease, urogenital disease, or a pulmonary disease. In an aspect, the at least one analyte sensor is configured to sense a tumor marker. For example, the tumor marker can include protein tumor markers. Non-limiting examples of protein tumor markers include alpha-fetoprotein, beta-2-microglobulin, beta-human chorionic gonadotropin, CA15-3/CA27.29, CA19-9, CA-125, calcitonin, calretinin, carcinoembryonic antigen, CD20, CD34, CD45, CD99, CD117, chromogranin, cytokeratin fragment 21-1, desmin, epithelial membrane antigen, estrogen receptor/progesterone receptor, fibrin/fibrinogen, glial fibrillary acidic protein, HE4, HER2/neu, HMB-45, immunoglobulins, inhibin, keratin, KIT, lactate dehydrogenase, Myo-D1, neuron-specific enolase, nuclear matrix protein 22, prostate-specific antigen, placental alkaline phosphates, S100 protein, synaptophysin, thyroglobulin, tumor M2-PK, urokinase plasminogen activator, vimentin, 5-protein signature, For example, the tumor marker can include genetic tumor markers. Non-limiting examples of genetic tumor markers includes ALK gene rearrangements, BCR-ABL fusion gene, BRAF mutation V600E, chromosomes 3, 7, 17, and 9p21, EGFR mutation, KRAS mutation, 21-gene signature, 70-gene signature. In an aspect, the at least one analyte sensor is configured to detect a tumor marker associated with a tumor cell in the aspirate. In an aspect, the at least one analyte sensor is configured to detect a tumor marker free in the aspirate.

In an aspect, the at least one analyte sensor is associated with a microfluidics component. In an aspect, all or part of an aspirate is processed using a microfluidics component associated with the tissue cutting device. Non-limiting examples of microfluidics devices for analyzing tumor cells is described in Chen et al. (2014) "Rare cell isolation and analysis in microfluidics," Lab Chip 14:626-645, which is incorporated herein by reference.

A variety of analytes sensors can be utilized in different embodiments of a tissue cutting device, depending on factors such as the intended use of the tissue cutting device, target tissue, disease condition, sensed analyte, size, weight, cost, bio-compatibility, safety and ease of disposal. "Sensors," as used herein, can be of a variety of types depending on the embodiment. One or more sensors can include at least one sensor responsive to changes in capacitance, or a measure of the ability of a configuration of materials to store electric charge. A general review of biosensors that detect changes in the dielectric properties of an electrode surface can be found in Berggren et al., "Capacitive Biosensors," *Electroanalysis* vol. 13, no. 3, 173-180, (2001), which is incorporated herein by reference. For example, the at least one analytes sensors can include a micromechanical biosensor with a fixed-fixed beam attached to an interdigitated capacitor (see, for example, Lim et al., "A Micromechanical Biosensor with Interdigitated Capacitor Readout," *Proceedings of the* 2011 *IEEE/ICME International Conference on Complex Medical Engineering*, May 22-25, Harbin, China, which is incorporated herein by reference). In an aspect, the at least one analytes sensor can include nanowire nanosensors, for example as described in Cui et al., "Nanowire Nanosensors for Highly Sensitive and Selective Detection of Biological and Chemical Species," *Science*, vol. 293, 1289-1292 (2001), which is incorporated herein by reference. In an aspect, the at least one analyte sensor can include those utilizing antibodies secured to a graphene substrate. See Tehrani et al., "Detection of Monoclonal Antibodies using Chemically Modified Graphite Substances," *IEEE Sensors* 2010 Conference Proceedings, 428-431, (2010), which is incorporated herein by reference. In some embodiments, the at least one analytes sensor includes aptamer-modified graphene field-effect transistors, see Ohno et al., "Graphene Field-Effect Transistors for Label-Free Biological Sensors," *IEEE Sensors* 2010 *Conference Proceedings,* 903-906, (2010), which is incorporated herein by reference. The at least one analyte sensor can include a field effect transistor (FET), such as described in U.S. Pat. No. 7,507,675 to Zuilhof et al., titled "Device Manufacturing Method and Device," which is incorporated herein by reference. The at least one analyte sensor can include a nano-cantilever device, such as described in U.S. Pat. No. 7,612,424 to Espinosa and Ke, titled "Nanoelectromechanical Bistable Cantilever Device," which is incorporated herein by reference.

In an aspect, the at least one analyte sensor includes a plasmonic biosensor. For example, the tissue cutting device can include an analyte sensor that includes components of a hand-held plasmonic microarray and computational on-chip imaging system such as described in Cetin et al., (2014) "Handheld high-throughput plasmonic biosensor using computational on-chip imaging," *Light: Science & Applications,* 3, e122, which is incorporated herein by reference.

In an aspect, the at least one analyte sensor includes a radioactivity sensor. For example, the at least one analyte sensor can sense a radioactive property of an aspirate. For example, the at least one analyte sensor can sense a radioactive property of a radiotracer added before and/or during the cutting process. Examples of detectors for detecting radioactivity include, but are not limited to, gas-filled tube detectors, e.g., Geiger counters; scintillation crystal detectors; and solid-state semiconductor detectors. In some embodiments, the one or more radioactivity sensors are one or more of a scintillation crystal detector made from a material that fluoresces or emits light when hit by radiation particles. The fluorescence or light can be measured using one or more optical sensors, e.g., a photomultiplier or photodiode. In an aspect, the one or more radioactivity sensors are one or more of a microdosimeter. A microdosimeter for wireless measurement of radioactivity in vivo has been described and is configured to detect ionizing radiation using a parallel plate capacitor to form a passive LC resonator. See, e.g., Son & Ziaie. *IEEE Trans. Biomed. Eng.* 55:1772-1775, 2008, which is incorporated herein by reference.

In an aspect, the at least one analyte sensor includes a magnetic sensor. For example, the at least one analyte sensor can sense a magnetic property of an aspirate using one or more MEMS magnetic sensors such as described in Kim et al. (2006) "A class of micromachined magnetic resonator for high-frequency magnetic sensor applications," *J. Applied Phys.* 99:08B309, which is incorporated herein by reference.

Torque Compensation

Figure 10A:
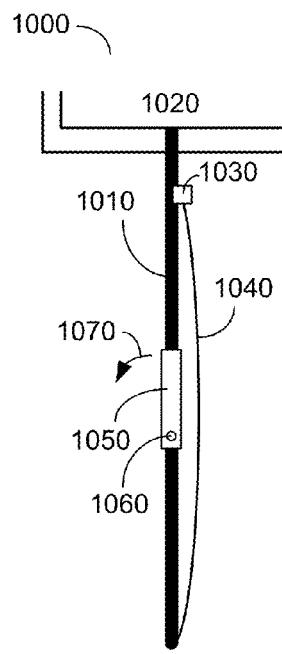
FIG. 10A illustrates aspects of a torque compensation component.
Figure 10B:
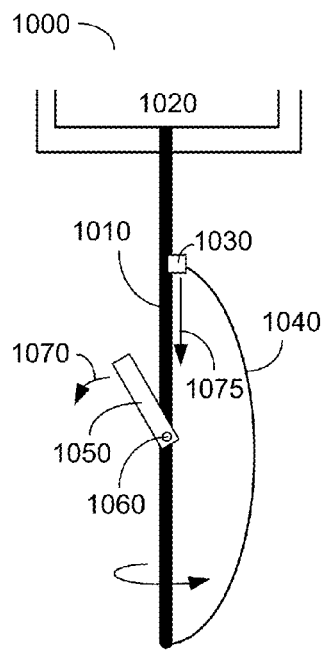
FIG. 10B illustrates aspects of a torque compensation component.
Figure 10C:
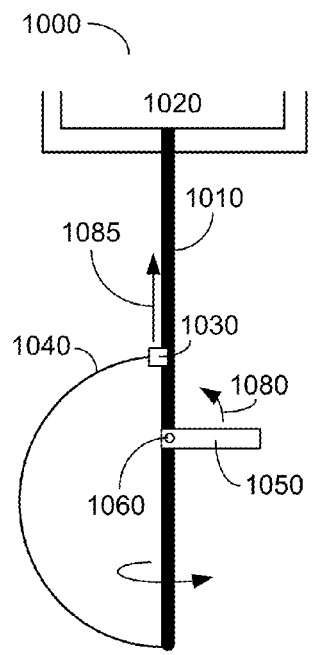
FIG. 10C illustrates aspects of a torque compensation component.

In some embodiments, the tissue cutting device includes a torque compensation component. In an aspect, the torque compensation component includes circuitry configured to prevent oscillation when performing asymmetric cutting patterns. For example, the torque compensation component can be configured to prevent oscillation of the tissue cutting device when the cutting radius of the elongated flexible cutting component changes during the course of a single rotation to generate an asymmetric cutting pattern. In an aspect, the torque compensation component includes at least one counterweight. FIGS. 10A-10C illustrate non-limiting aspects of a tissue cutting device including a counterweight. FIG. 10A shows tissue cutting device 1000. Tissue cutting device 1000 includes central rotatable shaft 1010, motor 1020, moveable component 1030, and elongated flexible cutting component 1040. Tissue cutting device 1000 further includes counterweight 1050 associated with the central rotatable shaft 1010. Counterweight 1050 includes a pivot point 1060 around which counterweight 1050 can pivot as shown with arrow 1070. Moveable component 1030 is positioned so that elongated flexible cutting component 1040 is flattened against central rotatable shaft 1010 and counterweight 1050 is aligned with central rotatable shaft 1010 to facilitate insertion into a body or lumen through a small incision or lumen diameter. FIGS. 10B and 10C illustrate counterweight 1050 pivoting around pivot point 1060 as motor 1020 rotates central rotatable shaft 1010 through a single rotation and moveable component 1030 moves up and down to change the shape of elongated flexible cutting component 1040 to form an asymmetric cutting pattern. FIG. 10B shows tissue cutting device 1000 in a first state, e.g., at 0 degrees of a single rotation. In this example, motor 1020 is rotating central rotatable shaft 1010. Moveable component 1030 is at a first position along the central rotatable shaft 1010, causing the elongated flexible cutting component 1040 to form a long and narrow D-shape. At this point, counterweight 1050 is shown pivoted around pivot 1060 to a first position. As motor 1020 continues to rotate the central rotatable shaft 1010 through the rotation, moveable component 1030 moves along a path shown by arrow 1075 and counterweight 1050 pivots along a path shown by arrow 1070. FIG. 10C shows tissue cutting device 1000 in a second state, e.g., at 180 degrees of the single rotation. Moveable component 1030 is at a second position along the central rotatable shaft 1010, causing the elongated flexible cutting component 1040 to form a short and wide D-shape. At this point in the single rotation, counterweight 1050 is shown pivoted around pivot 1060 to a second position. As motor 1020 continues to rotate central rotatable shaft 1010 around towards the completion of a single rotation, moveable component 1030 moves along a path shown by arrow 1085 and counterweight 1050 pivots along a path shown by arrow 1080. As the central rotatable shaft 1010 rotates, moveable component 1030 travels up and down changing the shape formed by elongated flexible cutting component 1040. Counterweight 1050 pivots back and forth around pivot point 1060 to counterbalance the changing shape formed by the elongated flexible cutting component 1040.

Figure 11A:
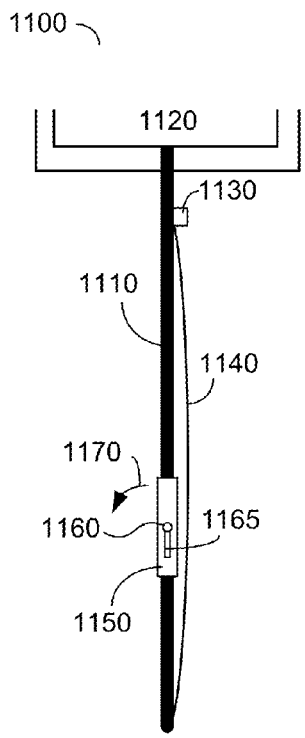
FIG. 11A illustrates aspects of a torque compensation component.
Figure 11B:
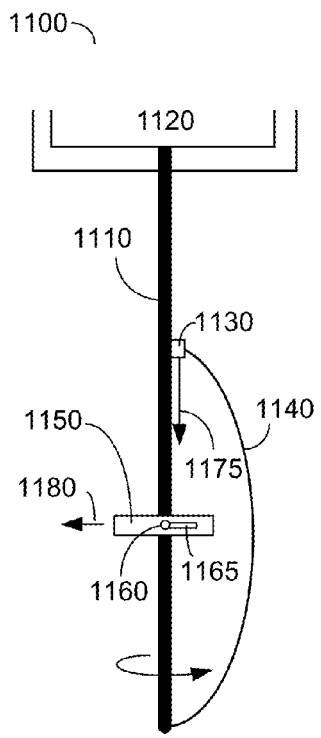
FIG. 11B illustrates aspects of a torque compensation component.
Figure 11C:
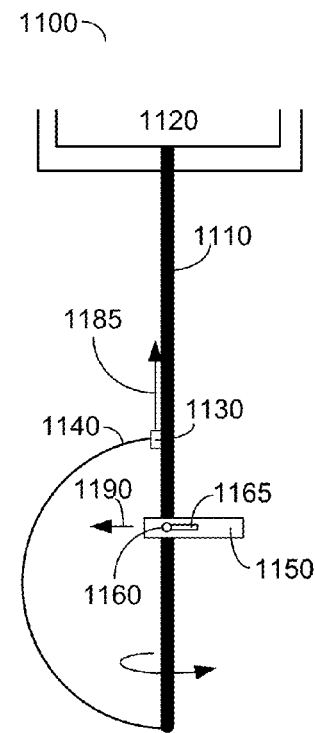
FIG. 11C illustrates aspects of a torque compensation component.

In an aspect, the torque compensation component includes at least one counterweight that is extendible. FIGS. 11A-11C illustrate non-limiting aspects of a tissue cutting device including an extendible counterweight. FIG. 11A shows tissue cutting device 1100. Tissue cutting device 1100 includes central rotatable shaft 1110, motor 1120, moveable component 1130, and elongated flexible cutting component 1140. Tissue cutting device 1100 further includes counterweight 1150 associated with the central rotatable shaft 1110. Counterweight 1150 includes a pivot point 1160 around which counterweight 1150 can pivot as shown with arrow 1170. Counterweight 1150 further includes a slide groove 1165 along which counterweight 1150 can extend by sliding. Moveable component 1130 is positioned so that elongated flexible cutting component 1140 is flattened against central rotatable shaft 1110 and counterweight 1150 is aligned with central rotatable shaft 1110 to facilitate insertion into a body or lumen through a small incision or lumen diameter. FIGS. 11B and 11C illustrate counterweight 1150 pivoting around pivot point 1160 and extending along slide groove 1165 as motor 1120 rotates central rotatable shaft 1110 through a single rotation and moveable component 1130 moves up and down to change the shape of elongated flexible cutting component 1140 to form an asymmetric cutting pattern. FIG. 11B shows tissue cutting device 1100 in a first state, e.g., at 0 degrees of a single rotation. In this example, motor 1120 is rotating central rotatable shaft 1110. Moveable component 1130 is at a first position along the central rotatable shaft 1110, causing the elongated flexible cutting component 1140 to form a long and narrow D-shape. At this point, counterweight 1150 is shown pivoted around pivot 1160 to a first position. As motor 1120 continues to rotate the central rotatable shaft 1110 through the rotation, moveable component 1130 moves along a path shown by arrow 1175 and counterweight 1150 extends along slide groove 1165 along a path shown by arrow 1190. FIG. 11C shows tissue cutting device 1100 in a second state, e.g., at 180 degrees of the single rotation. Moveable component 1130 is at a second position along the central rotatable shaft 1110, causing the elongated flexible cutting component 1140 to form a short and wide D-shape. At this point in the single rotation, counterweight 1150 is shown extended along slide groove 1165 to a second position. As motor 1120 continues to rotate central rotatable shaft 1110 around towards the completion of a single rotation, moveable component 1130 moves along a path shown by arrow 1185 and counterweight 1150 retracts along slide groove 1165 along a path shown by arrow 1180. As the central rotatable shaft 1110 rotates, moveable component 1130 travels up and down changing the shape formed by elongated flexible cutting component 1140. Counterweight 1150 extends and retracts along slide groove 1165 and around pivot point 1160 to counterbalance the changing shape formed by the elongated flexible cutting component 1140.

In an aspect, the torque compensation component includes circuitry and motors configured to control the position of the at least one counterweight. In an aspect, the torque compensation component is operably coupled to a computing component, the computing component including circuitry configured to control the torque compensation component.

Drag Compensation

Figure 12A:
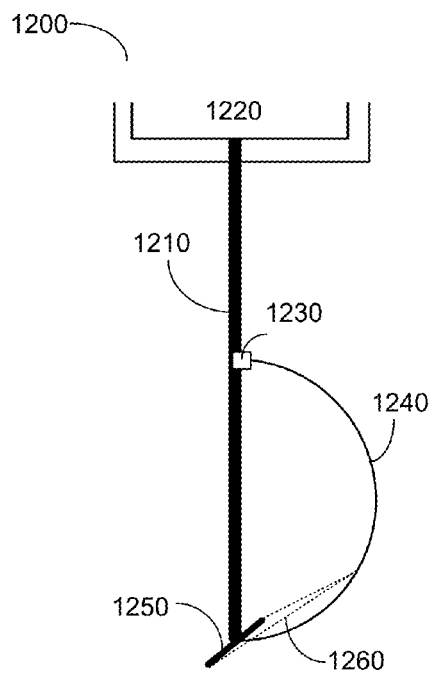
FIG. 12A illustrates aspects of a drag compensation component.
Figure 12B:
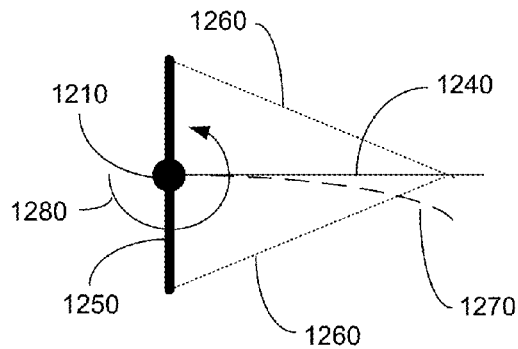
FIG. 12B illustrates aspects of a drag compensation component.

In some embodiments, a tissue cutting device includes a drag compensation component. For example, the tissue cutting device can include components to compensate for drag associated with the elongated flexible cutting component rotating through a tissue mass. In an aspect, a tissue cutting device includes a drag compensation component configured to prevent drag. For example, the tissue cutting device can include one or more stays (e.g., wires or strings) attached to the elongated flexible cutting component that prevent a portion of the elongated flexible cutting component from dragging or lagging behind during the cutting process. FIGS. 12A and 12B illustrate non-limiting aspects of a drag compensation component. FIG. 12A shows tissue cutting device 1200 including central rotatable shaft 1210, motor 1220, moveable component 1230, and elongated flexible cutting component 1240. Tissue cutting device 1200 further includes spar 1250 and stays 1260. In the example shown in FIG. 12A, spar 1250 is positioned at the end of central rotatable shaft 1210. However, spar 1250 could be positioned at other locations along the central rotatable shaft 1210. Stays 1260 are secured to spar 1250 and to elongated flexible cutting component 1240. Spar 1250 and stays 1260 are configured to rotate with the central rotatable shaft 1210 and the elongated flexible cutting component 1240. Stays 1260 are configured to prevent elongated flexible cutting component 1240 from lagging or dragging during rotation. FIG. 12B shows an end-on view of tissue cutting device 1200. Shown is the end of central rotatable shaft 1210 with spar 1250 associated with central rotatable shaft 1210. Stays 1260 are attached to spar 1250 at one end and to elongated flexible cutting component 1240. Stays 1260 prevent elongated flexible cutting component 1240 from lagging (as illustrated with dashed line 1270) during rotation (as illustrated by arrow 1280).

In an aspect, the drag compensation component includes circuity configured to measure drag from the elongated flexible cutting component during rotation. For example, the drag compensation component can include stays that attach to either side of the elongated flexible cutting component and detect drag, e.g., a lagging edge, of the elongated flexible cutting component during a cutting process. For example, one or more tensions sensors can be associated with the stays to measure changes in the tension associated with the stays as the elongated flexible cutting component rotates. For example, the drag compensation component can include a transceiver associated with the central rotatable shaft and at least one reflector associated with the elongated flexible cutting component to measure relative changes in distance between the central rotatable shaft and the elongated flexible cutting component.

Figure 13A:
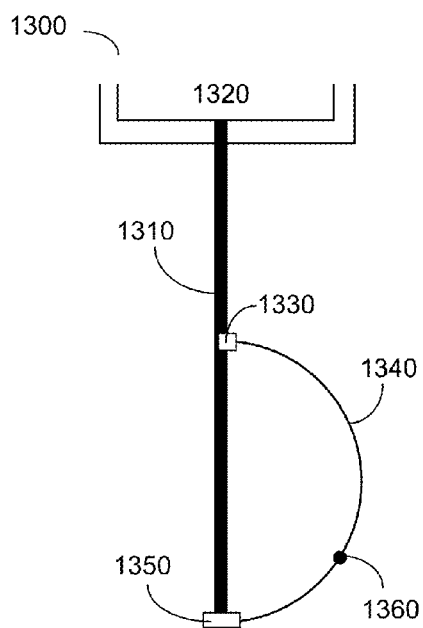
FIG. 13A illustrates aspects of a drag compensation component.
Figure 13B:
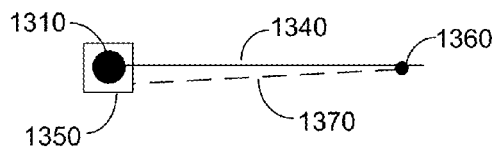
FIG. 13B illustrates aspects of a drag compensation component.
Figure 13C:
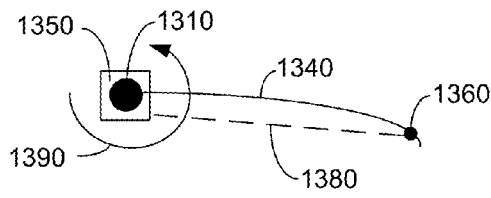
FIG. 13C illustrates aspects of a drag compensation component.

FIGS. 13A-C illustrate non-limiting aspects of a drag compensation component including a transceiver and at least one reflector. FIG. 13A shows a portion of tissue cutting device 1300 including central rotatable shaft 1310, motor 1320, moveable component 1330, and elongated flexible cutting component 1340. Tissue cutting device 1300 further includes transceiver 1350, shown here associated with the second end of the central rotatable shaft 1310. Tissue cutting device 1300 further includes at least one reflector 1360 associated with elongated flexible cutting component. In an aspect, the transceiver can be configured to transmit and receive optical signals, acoustic signals, radiofrequency signals, microwave signals, or electromagnetic signals. In an aspect, the at least one reflector reflects optical signals, acoustic signals, radiofrequency signals, microwave signals, or electromagnetic signals. In an aspect, transmission and receipt of a signal is used to determine a distance between the transceiver and the at least one reflector. FIG. 13B shows an end-on view of tissue cutting device 1300. Shown is a transceiver 1350 associated with central rotatable shaft 1310. Also shown is reflector 1360 associated with elongated flexible cutting component 1340 in a first position. A signal transmitted by transceiver 1350 and received back from reflector 1360 is used to measure length 1370. FIG. 13C shows an end-on view of tissue cutting device 1300 in which the elongated flexible cutting component is experiencing lag or drag during rotation (as illustrated by arrow 1390). Shown is a transceiver 1350 associated with central rotatable shaft 1310. Also shown is reflector 1360 associated with elongated flexible cutting component 1340 in a second position (e.g., lagging behind during rotation). A signal transmitted by transceiver 1350 and received back from reflector 1360 is used to measure length 1380. In an aspect, transceiver 1350 of the drag compensation component is operably coupled to a computing component, the computing component including circuitry configured to control at least one of the moveable component and the motor in response to the measured drag. Compensation may come in the form of moving the moveable component to a new position to maintain the cutting radius defined by the elongated flexible cutting component despite the drag on the elongated flexible cutting component.

Cautery Component

In some embodiments, the tissue cutting device includes a cautery component configured to cauterize a tissue during a cutting process. For example, as tissue is being cut and/or resected with the elongated flexible cutting component, a cautery component can be used to stop bleeding and/or destroy tissue at the site of resection. Cauterization can be carried out through the use of thermal energy (e.g., heat or cold), electrical current, corrosive chemicals, or focused light (e.g., laser). In an aspect, cauterization can be carried out using radiofrequency energy. In an aspect, the cautery component is operably coupled to the elongated flexible cutting component. For example, the elongated flexible cutting component can carry an electrical current, thermal energy (hot or cold), optical energy, or exude a chemical agent.

In an aspect, the cautery component includes an electrical cautery component. In some embodiments, an electric current is used to heat a metal probe for use in cauterization, i.e., burning or destroying tissue. In an aspect, an electric current is passed through a current-conducting elongated flexible cutting component. For example, at least a portion of the elongated flexible cutting component can include a wire capable of being electrically heated, e.g., platinum, iron, chromium, and aluminum alloy. In other embodiments, an electric current is used to directly heat the tissue. For example, the cautery component can include application of a high-frequency electrical current directly to the tissue. See, e.g., Massarweh et al. (2006) *J. Am. Coll. Surg.* 202:520-530, which is incorporated herein by reference.

In an aspect, the cautery component includes an optical cautery component. In an aspect, the optical cautery component includes an optical fiber including an optical energy sufficient to cauterize tissue. In an aspect, the optical cautery component includes a laser light source. In an aspect, the laser light is delivered in combination with an irrigation fluid to generate a fluid light stream. See, e.g., U.S. Pat. No. 8,814,921 to Aljuri & Perkins titled "Tissue Ablation and Cautery with Optical Energy Carried in Fluid Stream," which is incorporated herein by reference.

In an aspect, the cautery component includes a thermal cautery component. In an aspect, the thermal cautery component includes a heat cautery component. For example, the elongated flexible cutting component can be formed from a material, e.g., platinum, iron, chromium, or aluminum alloys, capable of being heated with an electrical current. In an aspect, the thermal cautery component includes a cold or cryo cautery component. For example, the tissue cutting component can include a source of a cryogenic agent, e.g., liquid nitrogen, dimethyl ether propane, or dry ice pellets, for application to the tissue cutting site.

In an aspect, the cautery component includes a chemical cautery component. For example, the cautery component can include one or more chemicals that stop bleeding and/or destroy tissue. Non-limiting examples includes silver nitrate, trichloroacetic acid, and cantharidin. In an aspect, the chemical cautery component can include a tissue adhesive, e.g., a form of cyanoacrylate. In an aspect, the chemical cautery component includes one or more cauterizing chemicals released from an irrigation fluid reservoir. For example, an irrigation fluid reservoir can release silver nitrate to wet the elongated flexible cutting component during a cutting procedure.

Power Source

In an aspect, the tissue cutting device includes a power source. In an aspect, at least one of the motor and the moveable component is powered by a power source. In an aspect, the tissue cutting device includes a power source operably coupled to and powering one or more components of the tissue cutting device. For example, the tissue cutting device can include at least one power source for powering the moveable component, the motor, a computing component, a vacuum source, an irrigation fluid reservoir, at least one analyte sensor, a torque compensation component, a drag compensation component, and/or a cautery component. In an aspect, the power source is incorporated into the tissue cutting device. In an aspect, the power source includes one or more batteries. In an aspect, the one or more batteries include one or more disposable batteries, e.g., cells, buttons, thin-film batteries, or microbatteries. For example, at least one of the moveable component and the motor of the tissue cutting device can be powered by a conventional battery, e.g., a disposable 9 volt battery. For example, at least one of the moveable component and the motor and one or more other components of the tissue cutting device can be powered by a conventional battery. Non-limiting examples of disposable batteries include zinc-carbon, alkaline, lithium, zinc-chloride, zinc-air, or silver-oxide batteries. In an aspect, the one or more batteries include one or more rechargeable batteries. For example, at least one of the moveable component and the motor can be powered by one or more rechargeable lithium-ion batteries. For example, at least one of the moveable component and the motor and one or more other components of the tissue cutting device can be powered by one or more rechargeable lithium-ion batteries. Non-limiting examples of rechargeable batteries include nickel-cadmium, nickel-zinc, nickel metal hydride, silver-zinc, or lithium ion. In an aspect, the power source includes kinetic energy, which may include stored kinetic energy.

In an aspect, the power source for the tissue cutting device includes an electrical cord accessing power through a common electrical output/socket. In an aspect, the power source for the tissue cutting device includes an electrical cord assessing power indirectly through a common electrical output/socket through connection to another powered device (e.g., a desk-top or lap-top computing device) through a USB port or similar type connection.

Handle Casing

In an aspect, the tissue cutting device further includes a handle casing, the handle casing covering at least a portion the motor, the handle casing including a user interface. In an aspect, the handle casing is sized for use with a single hand. In an aspect, the handle casing further covers one or more other components of the tissue cutting device including at least one of a computing component, an aspiration component, an irrigation component, an image-capture device, at least one analyte sensor, a torque compensation component, a drag compensation component, a cautery component, or a power source. In an aspect, the handle casing includes a user interface. In an aspect, the user interface includes at least one of an on/off switch, buttons, display screen, touchscreen, microphone, speakers, and the like for entering and receiving information.

Tissue Cutting System

Described herein are embodiments of a tissue cutting system including a tissue cutting device and a computing component, the tissue cutting device including a central rotatable shaft having a first end and a second end; a motor operably coupled to the first end of the central rotatable shaft, the motor including circuitry configured to rotate the central rotatable shaft; a moveable component configured to move along at least a portion of the length of the central rotatable shaft; and an elongated flexible cutting component having a first end and a second end, the first end of the elongated flexible cutting component secured to the moveable component and the second end of the elongated flexible cutting component secured to the central rotatable shaft in proximity to the second end of the central rotatable shaft; wherein movement of the moveable component along the at least a portion of the length of the central rotatable shaft changes a shape formed by the elongated flexible cutting component; and the computing component operably connected to the tissue cutting device, the computing component including a processor and circuitry.

Figure 14:
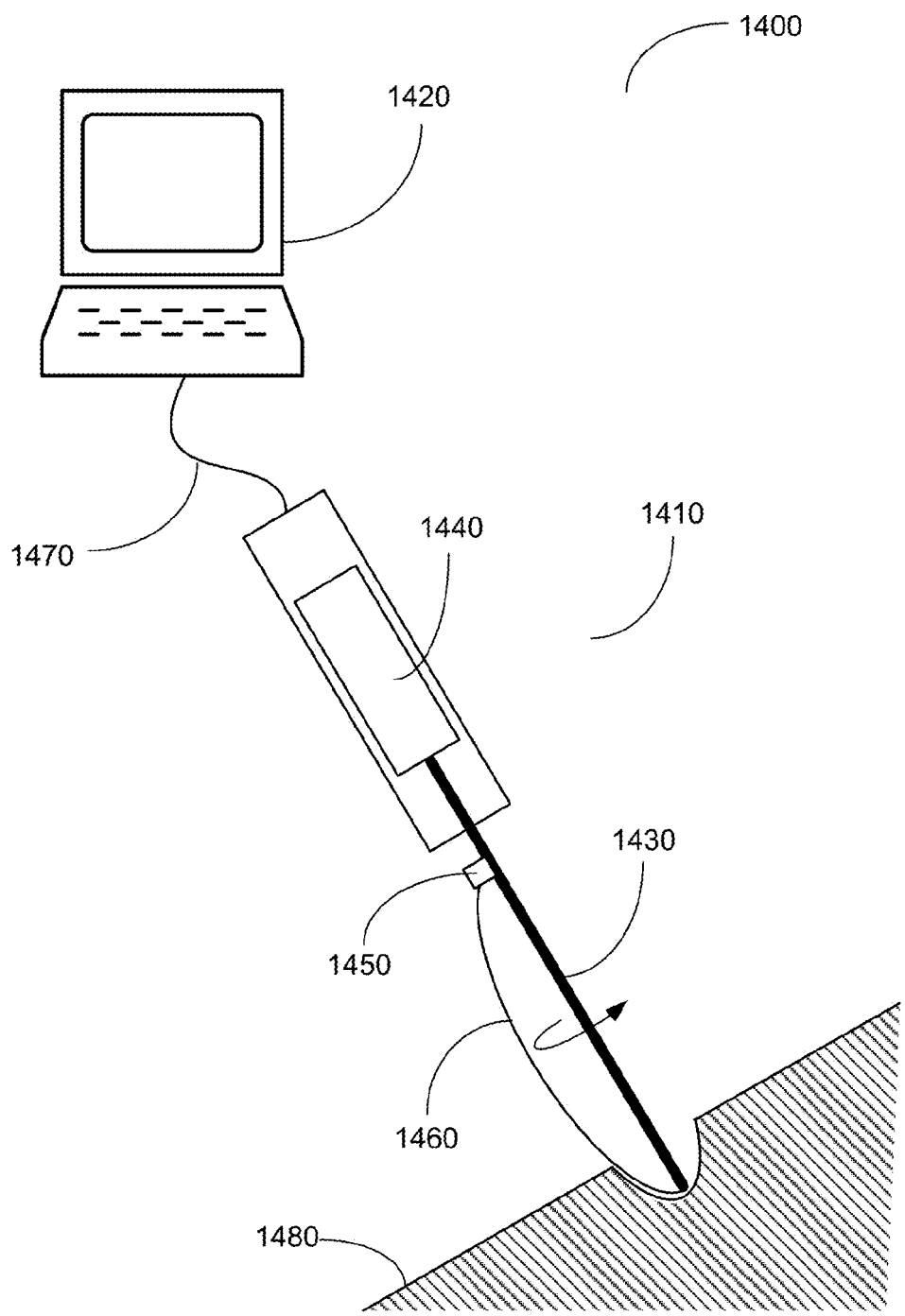
FIG. 14 is a schematic of a tissue cutting system.

FIG. 14 illustrates aspects of a tissue cutting system. System 1400 includes tissue cutting device 1410 and computing component 1420. Tissue cutting device 1410 includes central rotatable shaft 1430 operably coupled at one end to motor 1440. Tissue cutting device 1410 further includes elongated flexible cutting component 1460 secured at a first end to moveable component 1450 and at a second end to central rotatable shaft 1410.

In an aspect, the elongated flexible cutting component of the tissue cutting device is formed from metal. In an aspect, the elongated flexible cutting component of the tissue cutting device is formed from at least one polymer. In an aspect, the elongated flexible cutting component of the tissue cutting device is formed from at least one natural fiber. In an aspect, the elongated flexible cutting component of the tissue cutting device is formed from at least one man-made fiber. In an aspect, the elongated flexible cutting component of the tissue cutting device is at least one of a flexible wire, strand, string, fiber, thread, or ribbon. In an aspect, the elongated flexible cutting component of the tissue cutting device includes a circular cross-section. In an aspect, the elongated flexible cutting component of the tissue cutting device includes a non-circular cross-section. In an aspect, the elongated flexible cutting component of the tissue cutting device includes at least one cutting edge. In an aspect, the elongated flexible cutting component of the tissue cutting device includes at least one serrate edge. In an aspect, the elongated flexible cutting component of the tissue cutting device is replaceable. In some embodiments, the tissue cutting device includes two or more elongated flexible cutting components. In an aspect the first ends of the two or more elongated flexible cutting components are secured to the moveable component and the second ends of the two or more elongated flexible cutting components are secured to the central rotatable shaft. Additional non-limiting aspects of elongated flexible cutting components have been described above herein.

Tissue cutting device 1410 and computing component 1420 are operably connected through a communication link 1470. Communication link 1470 can include at least one of a wireless communication link (e.g., radio, microwave, optical, sonic, electromagnetic induction communication, or the like) or a wired communication link (e.g., electrical or fiber optic wire). Tissue cutting device 1410 of system 1400 is shown in the process of cutting tissue 1480, the shape of the resected tissue dictated by the shape formed by the rotating elongated flexible cutting component. In an aspect, computing component 1420 includes circuitry configured to control motor 1440. In an aspect computing component 1420 includes circuitry configured to control rotational frequency of motor 1440. In an aspect, computing component 1420 includes circuitry configured to control moveable component 1450. In an aspect, computing component 1420 includes circuitry configured to control at least one of speed of the moveable component, directionality of the moveable component, and/or distance traveled by the moveable component. In an aspect, computing component 1420 includes circuitry configured to control movement of the moveable component 1450 in coordination with rotational speed of elongated flexible cutting component 1460 to generate an asymmetric cutting pattern.

In an aspect, computing component 1420 can take various forms or be part of an object, and can include, but is not limited to, a computer, a laptop computer, a personal electronic device, a dedicated computing device, a limited resource computing device, a wireless communication device, a mobile wireless communication device, a handheld electronic writing device, a tablet, a digital camera, a scanner, a cell phone, a PDA, an electronic tablet device, a printer, or any other like device that takes information as an input and gives it back to the end-users. Computing component 1420 can include a digital single processor, ASIC, microprocessor, or other type of processor operating on a system such as a personal computer, server, a router, of other device capable of processing data including network interconnection device. Other aspects of a computing component have been described above herein.

Figure 15:
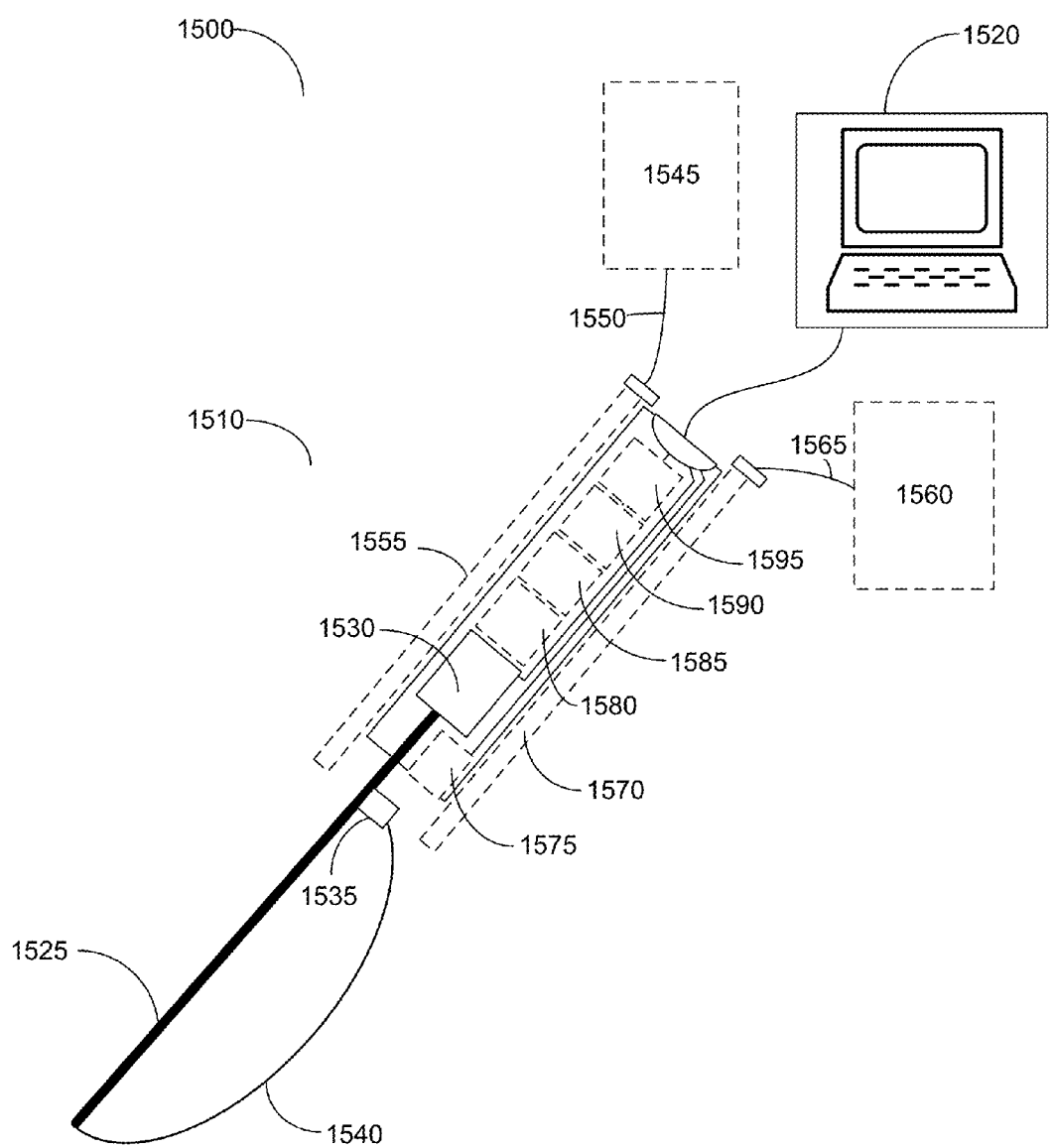
FIG. 15 illustrates further aspects of a tissue cutting system.

FIG. 15 illustrates further aspects of a tissue cutting system. System 1500 includes tissue cutting device 1510 and computing component 1520. Tissue cutting device 1510 includes central rotatable shaft 1525 operably coupled to motor 1530, motor 1530 including circuitry configured to rotate central rotatable shaft 1525. Tissue cutting device 1510 further includes moveable component 1535 configured to move along at least a portion of the length of central rotatable shaft 1525. Elongated flexible cutting component 1540 is secured to the moveable component 1535 at a first end and to the central rotatable shaft 1525 at a second end.

In some embodiments, tissue cutting system 1500 includes an aspiration component configured to aspirate tissue debris in proximity to the central rotatable shaft 1525 of the tissue cutting device 1510. The aspiration component includes a vacuum source and an aspirator connected to the vacuum source. In the non-limiting embodiment shown in FIG. 15, tissue cutting system 1500 includes an external vacuum source 1545 (e.g., a vacuum pump or a water aspirator) in fluid communication through a flow conduit 1550 (e.g., surgical tubing) with an aspirator 1555 attached to tissue cutting device 1510. In an aspect, at least a portion of the aspiration component is incorporated into the tissue cutting device. In an aspect, the aspirator of the aspiration component includes a suction lumen disposed in and defined by the central rotatable shaft 1525 of the tissue cutting device 1510, the suction lumen connected to the vacuum source 1545 and in fluid communication with one or more openings defined by the central rotatable shaft 1525 of the tissue cutting device 1510. In an aspect, the one or more openings defined by the central rotatable shaft are positioned along the length of the central rotatable shaft. In some embodiments, the entirety of the aspiration component, i.e., the vacuum source and the aspirator, may be incorporated into the tissue cutting device of the tissue cutting system. In an aspect, the aspiration component is operably coupled to computing device 1520. In an aspect computing component 1520 includes circuitry configured to control one or more functions (e.g., on/off and/or vacuum pressure) of the aspiration component.

In some embodiments, tissue cutting system 1500 includes an irrigation component configured to irrigate tissue in proximity to the central rotatable shaft 1525, the irrigation component including a flow conduit attached to an irrigation fluid reservoir. In an aspect, at least a portion of the irrigation component is incorporated into the tissue cutting device 1510. In the non-limiting embodiment shown in FIG. 15, tissue cutting system 1500 includes an external irrigation fluid reservoir 1560 in fluid communication through a flow conduit 1565 (e.g., surgical tubing) with an irrigation tube 1570 positioned proximal to the central rotatable shaft 1525 of the tissue cutting device 1510. In some embodiments, the flow conduit of the irrigation component includes an irrigation lumen disposed in and defined by the central rotatable shaft 1525 of the tissue cutting device 1510, the irrigation lumen connected to the irrigation fluid reservoir 1560 and in fluid communication with one or more openings defined by the central rotatable shaft 1525 of the tissue cutting device 1510. In some embodiments, the entirety of the irrigation component may be incorporated into the tissue cutting device of the tissue cutting system. In some embodiments, the entirety of the irrigation component may be a separate entity from the tissue cutting device. For example, the irrigation tube attached to the irrigation fluid reservoir may be physically separated from the tissue cutting device and held by a second hand of a user, e.g., a physician, or a second practitioner, e.g., a nurse. In an aspect, the irrigation component is operably coupled to computing component 1520. In an aspect, computing component 1520 includes circuitry configured to control one or more functions of the irrigation component.

In an aspect, the irrigation fluid reservoir 1560 is configured to hold and controllably release at least one irrigation fluid. In an aspect, irrigation fluid reservoir 1560 includes at least one controllable valve to hold and controllably release at least one irrigation fluid. In an aspect, the at least one controllable valve is operably coupled to computing component 1520. For example, the controllable valve can include a controllable gate, door, port, diaphragm, erodible barrier, or any other type of controllable valve configured to hold and controllably release at least one irrigation fluid from the irrigation fluid reservoir. In an aspect, the at least one irrigation fluid includes at least one of saline, a buffer, a therapeutic agent, an antimicrobial agent, an anesthetic, or a coagulant agent. Non-limiting aspects of irrigation fluids have been described above herein.

In some embodiments, tissue cutting system 1500 includes an image-capture device, the image-capture device operably coupled to the computing component 1520, the computing component 1520 including circuitry configured to receive image data from the image-capture device. In an aspect, the received image data includes one or more images of a tissue in proximity to the central rotatable shaft of the tissue cutting device. For example, the image-capture device can be configured to collect images of a target tissue before, during, and/or after a cutting procedure to monitor progress and success of the procedure. In an aspect, the image-capture device includes an optical image-capture device. In an aspect, the image-capture device includes an ultrasound image-capture device. In an aspect, at least a portion of the image-capture device is incorporated into tissue cutting device 1510. In the non-limiting embodiment shown in FIG. 15, tissue cutting system 1500 includes image-capture device 1575 incorporated into tissue cutting device 1510. In other embodiments, the image-capture device may include an external image-capture system, e.g., a digital camera, ultrasound, laparoscopy, or other tissue imaging modality (e.g., magnetic resonance, computed tomography, or fluoroscopy). In an aspect, computing component 1520 includes circuitry configured to control at least one of the motor 1530 and the moveable component 1535 of the tissue cutting device 1510 in response to the received image data. Non-limiting aspects of image-capture devices have been described above herein.

In an aspect, the image-capture device includes an energy-emitting component, e.g., a light source or a laser, and circuitry to scan the tissue with directed energy, e.g., light of a specified wavelength, to detect one or more signals emitted from the tissue and to transform the one or more detected signals into a digital output.

In an aspect, the one or more signals emitted from the tissue are indicative of properties of one or more tissue components, e.g., cells and/or biomolecules.

In an aspect, image-capture device 1575 includes at least one scanning device. Non-limiting examples of scanners include optical scanners, fluorescence scanners, acoustic scanners, electrical scanners, electromagnetic scanners, or magnetic scanners. In an aspect, the image-capture device includes a colorimetric scanner. In an aspect, the image-capture device includes fluorescence scanning device. In an aspect, the fluorescence scanning device can include fixed excitation/emission wavelengths based on the use of standard commercially available fluorescent dyes in the green, red, and near infrared wavelengths. For example, the fluorescence scanning device can include a two color scanner for scanning at two distinct wavelengths or wavelength bands. In an aspect, the fluorescence scanning device can include adjustable excitation/emission wavelengths, e.g., with one or more excitation sources and filters to adjust the excitation/emission wavelengths. In an aspect, image-capture device can be configured to detect a fluorescent response at a single wavelength of electromagnetic energy, at two wavelengths of electromagnetic energy, at multiple wavelengths of electromagnetic energy, or over extended-spectrum electromagnetic energy. In an aspect, the image-capture device can be configured to detect excitation energy. In an aspect, the image-capture device can be configured to detect a cumulative (optionally fluorescent) response over a time interval. In an aspect, the image-capture device can be configured to detect a (optionally fluorescent) response at a specific time interval and/or at a specific time. In an aspect, the image-capture device can be configured to detect a time-dependent (optionally fluorescent) response. In illustrative examples, the cumulative response is determined over milliseconds, seconds, and/or minutes following excitation. In an aspect, the response is detected over millisecond, second, and/or minute time intervals following excitation. In an aspect, the response is detected approximately femtoseconds, picoseconds, nanoseconds, milliseconds, seconds, and/or minutes after excitation.

In an aspect, the image-capture device includes components for micro-scanning in which a single CCD sensor with a Bayer filter is moved over the focus plane of the lens to "stitch" together a higher resolution image than the CCD would allow otherwise. In an aspect, the micro-scanning device includes a micro laser scanning device. See, e.g., Seidl et al. (2006) *International Society for Photogrammetry and Remote Sensing*. Volume XXXVI Part 5. September 25-27, 2006, Dresden Germany.

In an aspect, the image-capture device includes a three-dimensional scanning device. Non-limiting examples of three-dimensional scanning devices include NextEngine 3D Scanner (NextEngine, Inc., Santa Monica, Calif.), Handyscan 3D (Creaform USA Inc., Newark, Del.), or Konica Minolta 3D scanners (Konica Minolta, Ramsey, N.J.).

In an aspect, the image-capture device includes a confocal laser scanner. In an aspect, the confocal laser scanner can include a handheld confocal laser scanning microscope (e.g., VIVASCOPE 3000, MAVIG GmbH, Munich, Germany). In an aspect, the confocal laser scanner includes a MEMS confocal laser scanner. See, e.g., Murakami et al. (2003) *The 12th International Conference on Solid State Sensors, Actuators and Microsystems*, Boston, Jun. 8-12, 2003, pp. 587-590, which is incorporated herein by reference.

In an aspect, the image-capture device includes a light source and a detector for measuring reflected and/or absorbed light. In an aspect, the image-capture device measures changes in refractive index on the surface of the tissue. Resonance occurs at a specific angle of incident light. See, e.g., Barlen, et al. (2007) *Sensors*, 7:1427-1446; and Kashyap & Nemova (2009) *J. Sensors:* Article ID 645162, which are incorporated herein by reference.

In an aspect, the image-capture device includes a spectrometer or spectrophotometer. In an aspect, the spectrophotometer includes a fiber optic spectrophotometer (from, e.g., Ocean Optics, Dunedin Fla.). In an aspect, the image-capture device includes a means of vibrational spectroscopy. Examples of vibrational spectroscopy include, but are not limited to, Fourier transform infrared (FTIR) spectroscopy and micro-Raman spectroscopy. Raman spectroscopy can further include UV-resonance Raman spectroscopy, surface enhanced Raman scattering, or tip-enhanced Raman scattering. See, e.g., Harz et al. (2009) *Cytometry A* 75:104-113, which is incorporated herein by reference.

In an aspect, the image-capture device includes a light source, a digital projector, a CCD camera and a computing device for image-processing for spatial frequency domain imaging, a wide field optical technique. In an aspect, the image-capture device includes a lens-free imaging system. See, e.g., Kim et al. (2012) *J. Lab. Automation* 17:43-49, which is incorporated herein by reference.

In some embodiments, tissue cutting system 1500 includes at least one analyte sensor. In an aspect, the at least one analyte sensor includes at least one of an optical sensor, a magnetic sensor, an electrical sensor, an acoustic sensor, or a chemical sensor. In an aspect, at least a portion of the at least one analyte sensor is incorporated into the tissue cutting device 1510. In the non-limiting embodiment shown in FIG. 15, tissue cutting system 1500 includes at least one analyte sensor 1580 incorporated into tissue cutting device 1510. In an aspect, the at least one analyte sensor may be external to the tissue cutting device. For example, the at least one analyte sensor may be positioned in or accessible from the flow conduit 1550 leading to the external vacuum source 1545 of tissue cutting system 1500.

In an aspect, the at least one analyte sensor is configured to sense a property of one or more analytes in an aspirate. For example, the at least one analyte sensor can be used to determine whether the aspirate, e.g., tissue debris, contains disease-associated aspirates, e.g., disease-associated molecules or cells. For example, the at least one analyte sensor can be used to determine whether the aspirate contains tumor markers or neoplastic cells. In an aspect, the at least one analyte sensor is configured to sense an optical property, fluorescence property, magnetic property, electrical property, electromagnetic property, acoustic property, or chemical property of the one or more analytes in the aspirate. In an aspect, the at least one analyte sensor is configured to sense a radioactive property of one or more analytes in the aspirate. In an aspect, the at least one analyte sensor is operably coupled to the computing component 1520, the computing component 1520 including circuitry configured to receive sensor input from the at least one analyte sensor and to control at least one of the motor 1530 and the moveable component 1535 in response to the received sensor input. Non-limiting examples of analyte sensors have been described above herein.

In some embodiments, tissue cutting system 1500 includes a torque compensation component 1585. In an aspect, the torque compensation component is configured to prevent oscillation. In an aspect, the torque compensation component is configured to prevent oscillation while generating asymmetric cutting patterns. For example, the torque compensation component can be configured to prevent oscillation of the tissue cutting device when the cutting radius of the elongated flexible cutting component changes during the course of a single rotation to generate an asymmetric cutting pattern. In an aspect, the torque compensation component includes at least one counterweight. For example, the torque compensation component can include at least one counterweight associated with the central rotatable shaft 1525 of tissue cutting device 1510. In an aspect, the at least one counterweight moves, e.g., pivots, in response to changes in the shape formed by the elongated flexible cutting component 1540. For example, the at least one counterweight can pivot back and forth around a pivot point to counterbalance the changing shape formed by the elongated flexible cutting component 1540 as the moveable component 1535 moves up and down at least a portion of the length of the central rotatable shaft 1525 of the tissue cutting device 1510. A non-limiting example of a pivoting counterweight is illustrated in FIGS. 10A-C.

In an aspect, torque compensation component 1585 includes at least one counterweight that is extendible. In an aspect, the at least one counterweight extends and retracts in response to changes in the shape formed by the elongated flexible cutting component. For example, the at least one counterweight can extend and retract along a slide groove and around a pivot point to counterbalance the changing shape formed by the elongated flexible cutting component 1540 as the moveable component 1535 moves up and down at least a portion of the length of the central rotatable shaft 1525 of the tissue cutting device 1510. A non-limiting example of an extendable counterweight is illustrated in FIGS. 11A-C.

In an aspect, torque compensation component 1585 includes circuitry and motors configured to control the position of the at least one counterweight. In an aspect, torque compensation component 1585 is operably coupled to computing component 1520, the computing component including circuitry configured to control the torque compensation component. For example, computing component 1520 can include circuitry configured to control a position of at least one counterweight.

In some embodiments, tissue cutting system 1500 includes a drag compensation component 1590. For example, the drag compensation component can include a spar and one or more stays to stabilize the elongated flexible cutting component during rotation, a non-limiting example of which is shown in FIGS. 12A and 12B. In an aspect, drag compensation component 1590 is configured to measure drag from the elongated flexible cutting component 1540 of tissue cutting device 1510 during rotation. For example, the drag compensation component can includes a transceiver and at least one reflector to measure displacement of the elongated flexible cutting component during rotation, a non-limiting example of which is shown in FIGS. 13A-C and described above herein. In an aspect, drag compensation component 1590 is operably coupled to computing component 1520. In an aspect, computing component 1590 includes circuitry configured to control at least one of the moveable component and the motor in response to the measured drag. For example, the computing component can include circuitry configured to change the position of the moveable component and consequently the shape formed by the elongated flexible cutting component to compensate for the measured drag.

In some embodiments, tissue cutting system 1500 includes a cautery component 1595 configured to cauterize tissue during a cutting process. In an aspect, the cautery component 1595 is operably coupled to the elongated flexible cutting component 1540. For example, the elongated flexible cutting component can be configured with at least a portion of the cautery component to cauterize tissue during a cutting procedure. In an aspect, the cautery component includes an electrical cautery component. In an aspect, the cautery component includes an optical cautery component. In an aspect, the cautery component includes a thermal cautery component. In an aspect, the cautery component includes a chemical cautery component. Non-limiting aspects of cautery components have been described above herein. In an aspect, at least a portion of the cautery component is incorporated into the tissue cutting device.

Tissue Cutting Device Including a Tethering Component and at Least One Tether

Described herein is a tissue cutting device including a tethering component; an elongated flexible cutting component having a first end and a second end, the first end and the second end of the elongated flexible cutting component secured to the tethering component; at least one tether having a first end and a second end, the first end of the at least one tether attached to the elongated flexible cutting component at a position between the first end and the second end of the elongated flexible cutting component, the second end of the at least one tether operably coupled to the tethering component, the tethering component including circuitry configured to extend and retract the at least one tether; and a motor operably coupled to the tethering component, the motor including circuitry configured to rotate the tethering component and the secured elongated flexible cutting component; wherein extension and refraction of the at least one tether by the tethering component changes a shape formed by the elongated flexible cutting component.

Figure 16:
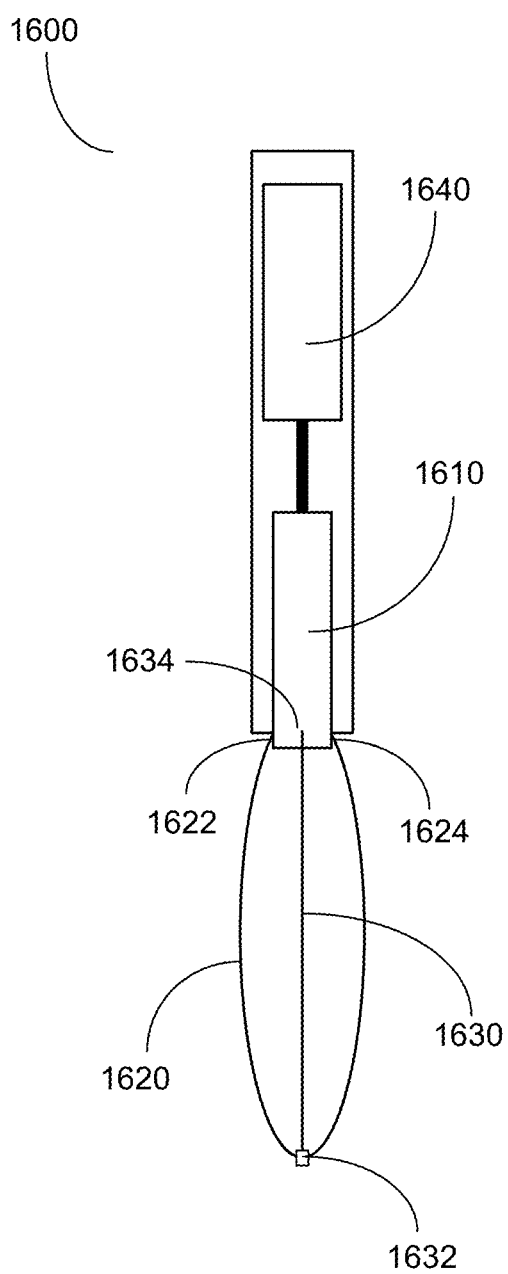
FIG. 16 is a schematic of a tissue cutting device including at least one tether.

FIG. 16 illustrates aspects of a tissue cutting device including a tethering component. Tissue cutting device 1600 includes tethering component 1610. Tissue cutting device 1600 further includes elongated flexible cutting component 1620. A first end 1622 of elongated flexible cutting component 1620 and a second end 1624 of elongated flexible cutting component 1620 are secured to tethering component 1610. Tissue cutting device 1600 further includes at least one tether 1630 including a first end 1632 and a second end 1634. The first end 1632 of the at least one tether 1630 is attached to elongated flexible cutting component 1620 at a position between the first end 1622 and the second end 1624 of elongated flexible cutting component 1620. The second end 1634 of the at least one tether 1630 is operably coupled to tethering component 1610. Tissue cutting device 1600 further includes motor 1640 operably coupled to tethering component 1610, motor 1640 including circuitry configured to rotate tethering component 1610. Elongation and retraction of the at least one tether 1630 by the tethering component changes a shape formed by the elongated flexible cutting component 1620. For example, retracting the at least one tether causes the elongated flexible cutting component to take a wider and shorter shape. For example, extending the at least one tether causes the elongated flexible cutting component to take a narrower and longer shape.

In an aspect, the elongated flexible cutting component 1620 forms a loop when attached at the first and the second end to the tethering component. In an aspect, extension or retraction of the at least one tether by the tethering component changes the shape of the loop formed by the elongated flexible cutting component. For example, the loop can be shortened and widened as the at least one tether is retracted by the tethering component. For example, the loop can be lengthened and narrowed as the at least one tether is extended by the tethering component. Rotation of the tethering component and the attached elongated flexible cutting component by the motor causes the elongated flexible cutting component to form a cutting pattern.

In an aspect, the shape formed by the elongated flexible cutting component is fixed. For example, the at least one tether can be positioned and locked into place prior to a cutting procedure, the shape formed by the elongated flexible cutting component remaining constant and creating a symmetrical cutting pattern as it rotates with the rotating tethering component.

In an aspect, the shape formed by the elongated flexible cutting component varies through the course of a cutting procedure. For example, the shape of the rotating elongated flexible cutting component can vary as the tissue cutting device is moved into the tissue, with a small cutting radius at the point of entering the tissue and a larger cutting radius once the target tissue for resection has been reached.

FIGS. 17A and 17B illustrate changes in the shape formed by the elongated flexible cutting component as well as the tissue cutting pattern in response to retraction of the tether by the tethering component. FIG. 17A shows tissue cutting device 1600 at a first time point relative to tissue 1700. Tissue cutting device 1600 includes tethering component 1610, elongated flexible cutting component 1620, tether 1630, and motor 1640. Tissue cutting device 1600 is shown cutting into tissue 1700 and target tissue mass 1710. Tether 1630 and elongated flexible cutting component 1620 are in a first position that creates resected space 1720 as tethering component 1610 and attached elongated flexible cutting component 1630 are rotated by motor 1640. As the elongated flexible cutting component 1620 rotates, it cuts away at tissue 1700 in a pattern dependent upon the shape formed by the elongated flexible cutting component 1620. FIG. 17B shows tissue cutting device 1600 at a second time point relative to tissue 1700. At this point, elongated flexible cutting component 1620 and tether 1630 are shown further into tissue 1700. Tether 1630 and elongated flexible cutting component 1620 are in a second position that creates resected space 1730 as tethering component 1610 and attached elongated flexible cutting component 1620 are rotated by motor 1640. In this example, tissue mass 1710 has been removed, leaving resected space 1730.

In an aspect, tissue cutting device 1600 such as described herein is used for minimally invasive surgery to cut and resect tissue. In an aspect, the tissue cutting device is inserted into a tissue of a patient. In some embodiments, the distal portion of the tissue cutting device (e.g., the first end of a rigid tether attached to the elongated flexible cutting component) is adapted to pierce tissue. In other embodiments, the tissue cutting device is inserted into a previously established surgical incision (e.g., a 0.5 cm to 2 cm incision). In an aspect, the tissue cutting device is inserted into a body lumen (e.g., a blood vessel, gastrointestinal tract, vagina, rectum, airway, ureter, or urethra).

A tissue cutting device such as described herein can enter tissue by any of a number of routes including, but not limited to, transabdominal, transperineal, transcutaneous, transvascular, transurethral, transureteral, transoral, transvaginal, and transrectal routes of insertion. A wide range of tissue can be cut and resected including but not limited to prostatic tissue, kidney tissue, liver tissue, uterine tissue, bladder tissue, and brain tissue. In an aspect, the tissue to be cut and resected is benign tissue (e.g., fibrotic tissue in uterus or prostate). In an aspect, the tissue to be cut and resected is malignant tissue (e.g., a solid tumor).

In an aspect, the tissue cutting device is sized for placement into cannula or trocar. For example, the elongated flexible cutting component and the at least one tether of the tissue cutting device may be extended from or refracted into a cannula or trocar configured for performing minimally invasive surgery.

Tissue cutting device 1600 includes elongated flexible cutting component 1620. In an aspect, the elongated flexible cutting component is formed from metal. For example, the elongated flexible cutting component includes a wire formed from stainless steel. In an aspect, the elongated flexible cutting component is formed from at least one polymer. For example, the elongated flexible cutting component can be a ribbon formed from nylon or polyethylene. In an aspect, the elongated flexible cutting component is formed from at least one natural fiber. For example, the elongated flexible cutting component can be formed from silk. In an aspect, the elongated flexible cutting component is formed from at least one man-made fiber. For example, the elongated flexible cutting component can be formed from carbon fiber. In an aspect, the elongated flexible cutting component includes at least one of a flexible wire, strand, string, fiber, thread, or ribbon. In an aspect, the elongated flexible cutting component includes a circular cross-section. In an aspect, the elongated flexible cutting component includes a non-circular cross-section (e.g., a polygon with three or more sides). In an aspect, the elongated flexible cutting component includes at least one cutting edge. In an aspect, the elongated flexible cutting component includes at least one serrated edge. In an aspect, the elongated flexible cutting component is replaceable. Other non-limiting aspects of an elongated flexible cutting component have been described above herein.

In an aspect, tissue cutting device 1600 further includes two or more elongated flexible cutting components. In an aspect, a first end and a second end of each of the two or more elongated flexible cutting components is attached to the tethering component. In an aspect, each of the two or more elongated flexible cutting components is attached to at least one tether. In an aspect, each of the at least one tether attached to each of the two or more elongated flexible cutting components extends and retracts independently. In an aspect, each of the at least one tether attached to each of the two or more elongated flexible cutting components extends and retracts simultaneously.

Tethering Component

Tissue cutting device 1600 includes a tethering component 1610 configured to extend and retract the at least one tether. In an aspect, the tethering component includes a manual tethering component. For example, the tethering component can include a fastening device for holding the at least one tether at a specific length. For example, the fastening device can include a clamping device, a holding device, a clinching device, a cinching device, an anchoring device, a hitching device, or a securing device. For example, the fastening device can include a clamp, a snap, a screw, or a pin. For example, the tethering component can include a "pull-through" function in which the at least one tether (e.g., a wire, string, chain, or ribbon) is pulled through a closable fastening device until the appropriate length is reached and the closable fastening device is closed.

In an aspect, the tethering component includes a locking component configured to hold the at least one tether at a specific length. For example, the tethering component can include a lockable clamp. For example, the tethering component can include at least one lockable gear with a gripping surface (e.g., teeth, abrasive, or adhesive) designed to interact with the at least one tether and prevent slippage. For example, the tethering component can include a hinged or pivoted device, e.g., a pawl, adapted to fit into a notch of a ratchet wheel to impart extension and/or retraction or to prevent extension and/or refraction.

In some embodiments, the tethering component includes circuitry configured to extend and retract the at least one tether. For example, the tethering component can include a ratchet or gears configured to controllably extend and/or retract the at least one tether. For example, the tethering component can include a motorized ratchet or gears configured to controllably extend and/or retract the at least one tether. In an aspect, the tethering component includes circuitry configured to either extend or retract the tethering component. For example, the tethering component can include a locking component and a retraction component, the at least one tether extended by centrifugal force of rotation, locked after sufficient extension, and refracted by the retraction component. In an aspect, the tethering component includes at least one rotatable component, the second end of the at least one tether secured to the at least one rotatable component, the at least one rotatable component configured to extend and retract the secured at least one tether. For example, the tethering component can include a rotatable gear to which at least one tether is secured and a second motor including circuitry configured to rotate the rotatable gear to extend and retract the attached tether. For example, the tethering component can include one or more rotatable gears configured to generate reciprocating motion to extend and/or retract a rigid tether (e.g., a rod).

Tethering component 1610 is operably coupled to motor 1640. Motor 1640 includes circuitry configured to rotate tethering component 1610 and the secured elongated flexible cutting component 1620. In an aspect, the tethering component is attached to a rotating shaft of the motor. In an aspect, the motor is a rotary shaft motor, such as a conventional DC, pulse, or AC motor. In an aspect, the motor can include a brush DC motor. In an aspect, the motor can include a DC servo. In an aspect, the motor can include a rotary piezoelectric motor. Other non-limiting examples of motors for use in rotating the central rotatable shaft include a stepper control motor, a brushless DC commutated control motor, or a universal motor. In general, motors for use in small electronics or hand-held devices are known in the art and available from commercial sources.

Tether

Tissue cutting device 1600 includes at least one tether 1630 having a first end and a second end, the first end of the at least one tether attached to the elongated flexible cutting component 1620 at a positon between the first end and the second end of the elongated flexible cutting component 1620, the second end of the at least one tether operably coupled to the tethering component 1610, the tethering component 1610 configured to extend and retract the at least one tether 1630. In an aspect, the at least one tether includes at least one flexible tether. For example, the at least one tether can include a wire that is attached at one end to the elongated flexible cutting component and at the other end to the tethering component. In an aspect, the at least one tether includes at least one rigid tether. For example, the at least one tether can include a rigid rod that is attached at one end to the elongated flexible cutting component and at the other end to the tethering component. In an aspect, the at least one tether is formed from metal. For example, the at least one tether can be formed from platinum, silver, iron, copper, aluminum, or gold. For example, the at least one tether can be formed from a metal alloy, e.g., stainless steel, brass, or bonze. In an aspect, the at least one tether is formed from at least one polymer. For example, the at least one tether can be formed from a plastic polymer. In an aspect, the at least one tether is formed from at least one of natural fiber and man-made fiber. In an aspect, the at least one tether is formed from natural fiber. For example, the at least one tether can be formed from vegetable fiber, e.g., cotton, hemp, jute, flax, ramie, sisal, or bagasse. For example, the at least one tether can be formed from wood fiber. For example, the at least one tether can be formed from animal fibers, e.g., silkworm silk, spider silk, sinew, catgut, wool, sea silk, or hair. For example, the at least one tether can be formed from mineral fibers, e.g., asbestos. In an aspect, the at least one tether is formed from man-made fiber. For example, the at least one tether can be formed from regenerated fibers, e.g., cellulose from wood pulp. For example, the at least one tether can be formed from semi-synthetic fibers, e.g., nylon (polyamide), Dacron (polyester), and rayon. For example, the at least one tether can be formed from synthetic fibers, e.g., metallic fibers, carbon fiber, silicon carbide fiber, fiberglass, mineral fibers, polymer fibers, and microfibers. In an aspect, the at least one tether is formed from polymer fibers, non-limiting examples of which include polyamide nylon, PET or PBT polyester, phenol-formaldehyde, polyvinyl chloride fiber, polyolefin fibers, acrylic polyesters, aromatic polyamids, polyethylene, elastomers, polyurethane fiber, elastolefin. In an aspect, the at least one tether is at least one of a wire, strand, string, fiber, ribbon, or rod. In an aspect, the at least one tether is replaceable.

In an aspect, the at least one tether is attached equidistance from the first and second ends of the elongated flexible cutting component. In an aspect, the at least one tether is attached closer to either the first or the second end of the elongated flexible cutting component. In an aspect, the at least one tether is attached to the elongated flexible cutting component so as to form a symmetrical cutting pattern, e.g., an oval cutting pattern. In an aspect, the at least one tether is attached to the elongated flexible cutting component so as to form an asymmetrical cutting pattern. In an aspect, extension and retraction of the at least one tether during the course of a single rotation of the elongated flexible cutting component creates an asymmetrical cutting pattern.

In an aspect, the at least one tether includes two or more first ends and one second end. For example, the at least one tether can include a Y-shape. In an aspect, each of the two or more first ends of the at least one tether are attached to the elongated flexible cutting component at a position between the first end and the second end of the elongated flexible cutting component. In an aspect, the second end of the at least one tether is operably coupled to the tethering component.

In an aspect, the at least one tether includes at least one first end attached to the elongated flexible cutting component and at least one second end operably coupled to the tethering component. For example, the at least one tether can include an X-shape, wherein two of the ends are attached to the elongated flexible cutting component and the remaining two ends are operably coupled to the tethering component. In an aspect, each of the ends of the at least one tether operably coupled to the tethering component are configured to be independently extended and retracted by the tethering component. In an aspect, each of the ends of the at least one tether operably coupled to the tethering component are configured to be simultaneously extended and retracted by the tethering component.

In some embodiments, a tissue cutting device includes two or more tethers attached at one end to an elongated flexible cutting component and at a second end to a tethering component. FIGS. 18A-C illustrate aspects of a tissue cutting device including two tethers. FIG. 18A shows tissue cutting device 1800 including tethering component 1810, elongated flexible cutting component 1820, and motor 1850. Elongated flexible cutting component 1820 is attached at a first end 1822 and at a second end 1824 to tethering component 1810. Tissue cutting device 1800 further includes a first tether 1830 and a second tether 1840. First tether 1830 is attached at a first end 1832 to elongated flexible cutting component 1820. A second end 1834 of first tether 1830 is operably coupled to tethering component 1810. Second tether 1840 is attached at a first end 1842 to elongated flexible cutting component 1820. A second end 1844 of second tether 1840 is operably coupled to tethering component 1810. Elongated flexible cutting component 1820 is shown in a slack position in the absence of rotation.

In some embodiments, a first tether and a second tether attached to an elongated flexible cutting component are retracted simultaneously by a tethering component, as illustrated in FIG. 18B. Tissue cutting device 1840 is shown with motor 1850 rotating tethering component 1810 and attached elongated flexible cutting component 1820, first tether 1830, and second tether 1840. As elongated flexible cutting component 1820 rotates, the slack portion swings out in response to outward centrifugal forces (arrows 1860). First tether 1830 and second tether 1840 are shown at the same retracted state, causing the elongated flexible cutting component 1820 to form a symmetrical shape.

In some embodiments, a first tether and a second tether attached to an elongated flexible cutting component are retracted asymmetrically by a tethering component, as illustrated in FIG. 18C. Tissue cutting device 1800 is shown with motor 1850 rotating tethering component 1810 and attached elongated flexible cutting component 1820, first tether 1830, and second tether 1840. In this non-limiting example, tethering component 1810 has asymmetrically retracted first tether 1830 along a path illustrated by arrow 1870 relative to second tether 1840, causing elongated flexible cutting component 1820 to form an asymmetrical shape.

In an aspect, the shape formed by the elongated flexible cutting component and the at least one tether is set and locked prior to initiating the cutting procedure. In an aspect, the shape formed by the elongated flexible cutting component and the at least one tether is changed during the course of the cutting procedure. For example, the tethering component can extend and/or retract the at least one tether during the course of the resection procedure to alter the cutting pattern formed by the elongated flexible cutting component. In an aspect, the shape formed by the elongated flexible cutting component and the at least one tether is changed during the course of a single rotation of the tethering component. For example, the tethering component can extend and/or retract the at least one tether during a single rotation of the tethering component and the attached elongated flexible cutting component to alter the cutting pattern formed by the elongated flexible cutting component.

Figure 19:
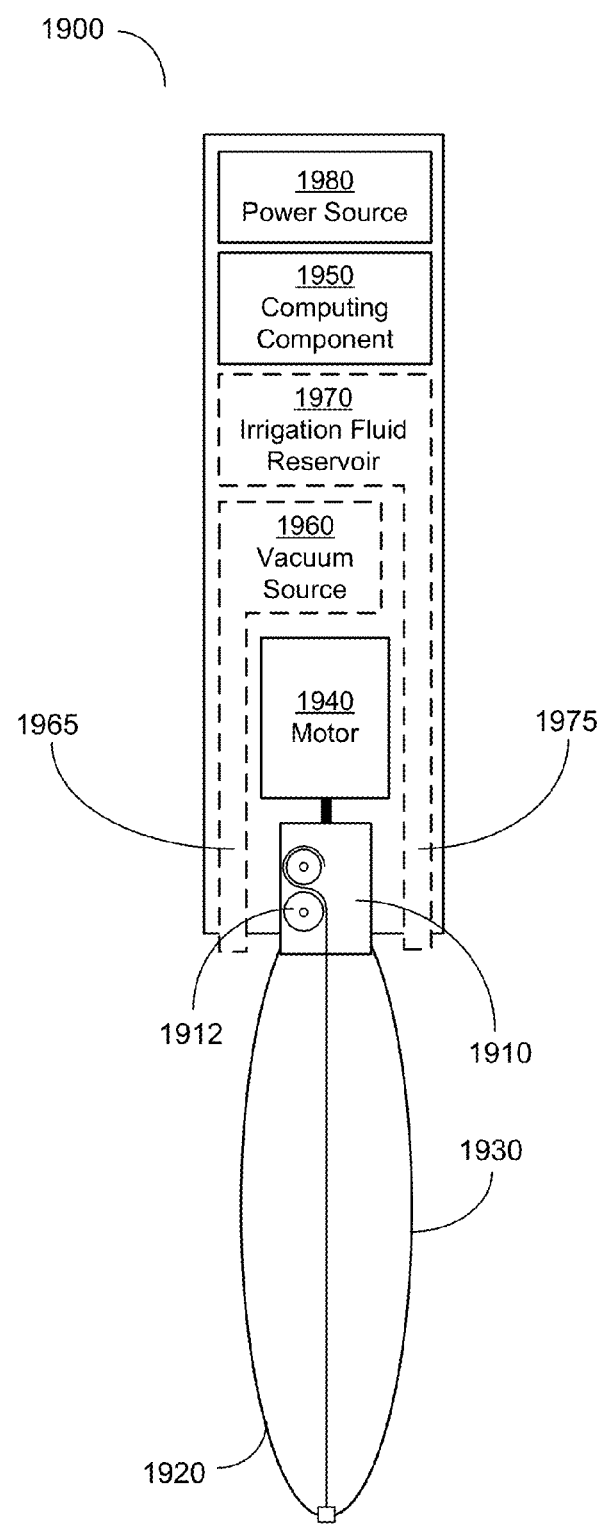
FIG. 19 illustrates further aspects of a tissue cutting device including at least one tether.

FIG. 19 illustrates further aspects of a tissue cutting device such as shown in FIG. 16. In an aspect, tissue cutting device 1900 includes tethering component 1910, elongated flexible cutting component 1920, tether 1930, and motor 1940. In this non-limiting examples, tethering component 1910 includes at least one rotatable component 1912, the second end of tether 1930 secured to the at least one rotatable component 1912, the at least one rotatable component 1912 configured to at least one of extend and retract the at least one tether 1930. For example, the at least one rotatable component 1912 can be configured to extend and/or retract the at least one tether 1930.

Tissue cutting device 1900 further includes computing component 1950. In an aspect, computing component 1950 includes a processor and circuitry. In an aspect, computing component 1950 is operably coupled to at least one of tethering component 1910 and motor 1940. In an aspect, computing component 1950 includes circuitry configured to control tethering component 1910. In an aspect, computing component 1950 includes circuitry configured to control at least one of extension and retraction of the at least one tether 1930 by tethering component 1910. In an aspect, computing component 1950 includes circuitry configured to control at least one of speed and length of extension of the at least one tether 1930 by the tethering component 1910. In an aspect, computing component 1950 includes circuitry configured to control at least one of speed and length of retraction of the at least one tether 1930 by tethering component 1910. For example, the computing component can include circuitry configured to control at least one of speed, distance traveled, and directionality of the tethering component. In an aspect, computing component 1950 includes circuitry configured to control motor 1940. In an aspect, computing component 1950 includes circuitry configured to control rotational frequency of the motor 1940. For example, the computing component can include circuitry configured to control rotational frequency of the tethering component operably coupled to the motor. Non-limiting aspects of a computing component have been described above herein.

In an aspect, tissue cutting device 1900 includes an aspiration component configured to aspirate tissue debris in proximity to the elongated flexible cutting component. The aspiration component further includes a vacuum source and an aspirator connected to the vacuum source. FIG. 19 illustrates a non-limiting example of a tissue cutting device including an aspiration component. Tissue cutting device 1900 includes vacuum source 1960 and an aspirator 1965 connected to the vacuum source. In an aspect, the aspirator includes a suction tube positioned proximal to the elongated flexible cutting component, the suction tube connected to the vacuum source. In an aspect, the aspirator includes a suction tube positioned outside a cutting radius of the elongated flexible cutting component, the suction tube connected to the vacuum tube. In an aspect, the aspirator includes a suction tube positioned inside a cutting radius of the elongated flexible cutting component. For example, the suction tube can be positioned parallel to the length of the at least one tether. For example, the aspirator can include a suction lumen disposed in and defined by a rigid tether, e.g., a suction lumen defined by a rod.

In an aspect, tissue cutting device 1900 includes an irrigation component configured to irrigate tissue in proximity to the elongated flexible cutting component. The irrigation component further includes a flow conduit attached to an irrigation reservoir. FIG. 19 illustrates a non-limiting example of a tissue cutting device including an irrigation component. Tissue cutting device 1900 includes irrigation fluid reservoir 1970 and fluid conduit 1975. In an aspect, the flow conduit includes an irrigation tube positioned proximal to the elongated flexible cutting component, the irrigation tube connected to the irrigation fluid reservoir. In an aspect, the flow conduit includes an irrigation tube positioned outside of a cutting radius of the elongated flexible cutting component, the irrigation tube connected to the irrigation fluid reservoir. In an aspect, the flow conduit includes an irrigation tube positioned inside of a cutting radius of the elongated flexible cutting component, the irrigation tube connected to the irrigation fluid reservoir. For example, the irrigation tube can be positioned parallel to the length of the at least one tether. For example, the flow conduit can include an irrigation lumen disposed in and defined by a rigid tether, e.g., an irrigation lumen defined by a rod.

In an aspect, irrigation fluid reservoir 1970 is configured to hold and controllably release at least one irrigation fluid. In an aspect, irrigation fluid reservoir 1970 includes at least one controllable valve, the at least one controllable valve operably coupled to a computing component, e.g., computing component 1950. For example, the controllable valve can include a controllable gate, door, port, diaphragm, erodible barrier, or any other type of controllable valve configured to hold and controllably release at least one irrigation fluid from the irrigation fluid reservoir. In an aspect, the at least one irrigation fluid includes at least one of saline, a buffer, a therapeutic agent, an antimicrobial agent, an anesthetic, or a coagulant agent. Non-limiting examples of irrigation fluid components have been described above herein.

In an aspect, tissue cutting device 1900 further includes power source 1980. In an aspect, power source 1980 includes an electrical connection, e.g., a wired connection, to a conventional electrical outlet. In an aspect, power source 1980 includes one or more batteries.

Figure 20:
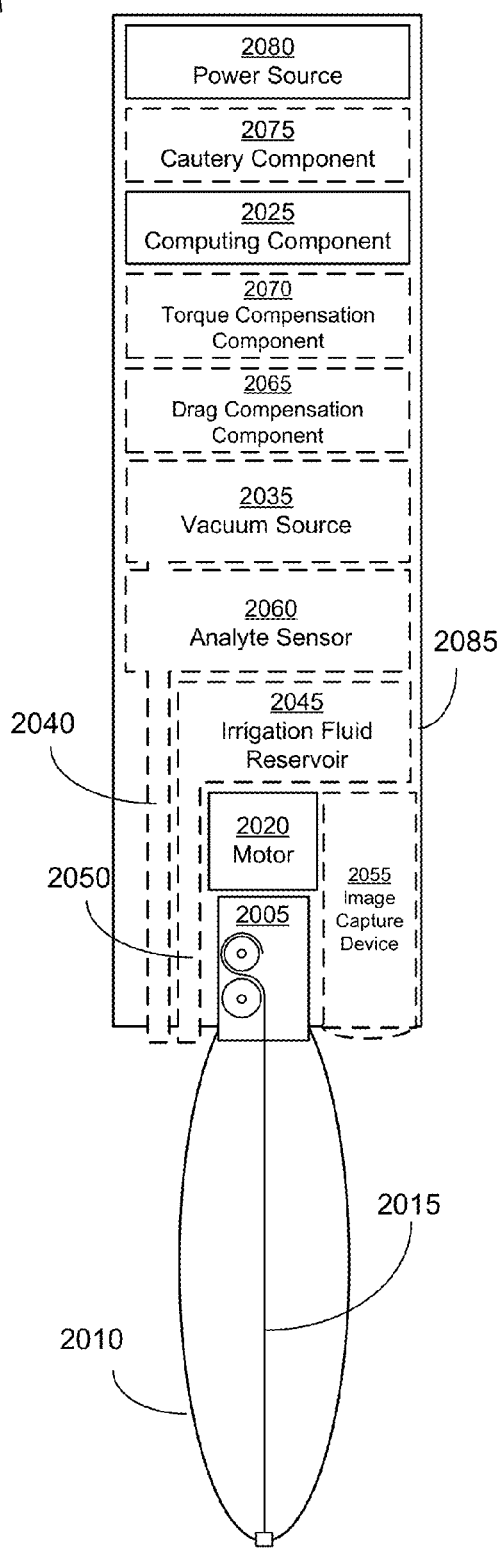
FIG. 20 illustrates further aspects of a tissue cutting device including at least one tether.

FIG. 20 illustrates further aspects of a tissue cutting device such as shown in FIG. 20. Tissue cutting device 2000 includes tethering component 2005, elongated flexible cutting component 2010, at least one tether 2015, and motor 2020. Tissue cutting device 2000 further includes computing component 2025 including a processor and circuitry. Tissue cutting device 2000 further includes power source 2080. For example, tissue cutting device 2000 can include an electrical cord for use with an electrical outlet. For example, tissue cutting device 2000 can include one or more batteries. In some embodiments, tissue cutting device 2000 includes an aspiration component including vacuum source 2035 and aspirator 2040. In some embodiments, tissue cutting device 2000 includes an irrigation component including an irrigation fluid reservoir 2045 and a flow conduit 2050. In some embodiments, tissue cutting device 2000 includes both an aspiration component and an irrigation component.

In some embodiments, tissue cutting device 2000 includes image-capture device 2055. The image-capture device 2055 is operably coupled to a computing component 2025, the computing component 2025 including circuitry configured to receive image data from image-capture device 2055. In an aspect, image-capture device 2055 includes an optical image-capture device. For example, image-capture device 2055 can include a digital camera, a fluoroscope, or a laparoscope. In an aspect, image-capture device 2055 includes an ultrasound image-capture device.

In some embodiments, tissue cutting device 2000 includes at least one analyte sensor 2060. The at least one analyte sensor is configured to sense a property of one or more analytes in an aspirate. In an aspect, the at least one analyte sensor includes at least one of an optical sensor, a magnetic sensor, an electrical sensor, an acoustic sensor, or a chemical sensor. In an aspect, the at least one analyte sensor is configured to sense an optical property, fluorescence property, magnetic property, electrical property, electromagnetic property, acoustic property, or chemical property of the one or more analytes in the aspirate. In an aspect, the at least one analyte sensor is configured to sense in situ a property of the target tissue before, during, and/or after the resection procedure. For example, the at least one analyte sensor can be configured to sense in situ an optical property, a fluorescence property, a magnetic property, an electrical property, electromagnetic property, acoustic property, or chemical property of the target tissue before, during, and/or after the resection procedure. Non-limiting aspects of analyte sensors have been described above herein.

In some embodiments, tissue cutting device 2000 includes drag compensation component 2065. For example, the drag compensation component can include at least one spar and one or more stays such as described in FIGS. 12A and 12B. In an aspect, the drag compensation component includes circuitry configured to measure drag from the elongated flexible cutting component during rotation. For example, the drag compensation component can include a transceiver and at least one reflector, such as described in FIGS. 13A-C. In an aspect, the drag compensation component 2065 is operably coupled to a computing component 2025, the computing component 2025 including circuitry configured to control at least one of the tethering component and the motor in response to the measured drag.

In an aspect, embodiments, tissue cutting device 2000 includes torque compensation component 2070. In an aspect, the torque compensation component includes circuitry configured to prevent oscillation. For example, the torque compensation component can include circuitry configured to prevent oscillation during an asymmetric cutting procedure. In an aspect, the torque compensation component includes at least one counterweight. For example, the torque compensation component can include at least one pivoting counterweight associated with the tissue cutting device. In an aspect, the torque compensation component includes at least one counterweight that is extendable. In an aspect, torque compensation component 2070 is operably coupled to computing component 2025, computing component 2025 including circuitry configured to control the torque compensation component 2070. For example, computing component 2025 can includes circuitry to control movement of the at least one counterweight.

In some embodiments, tissue cutting device 2000 includes cautery component 2075. In an aspect, the cautery component is configured to cauterize tissue during a cutting process. In an aspect, the cautery component is operably coupled to the elongated flexible cutting component. For example, the elongated flexible cutting component can be electrified and/or heated to cauterize while cutting. In an aspect, the cautery component includes at least one of an electrical cautery component, an optical cautery component, a thermal cautery component, or a chemical cautery component.

In an aspect, tissue cutting device 2000 further includes a handle casing 2085, the handle casing covering at least a portion of the tethering component and the motor, the handle casing including a user interface. In an aspect, the handle casing is sized for use with a single hand. In an aspect, the handle casing further covers one or more other components of the tissue cutting device (e.g., the tethering component, a computing component, an aspiration component, an irrigation component, an image-capture device, at least one analyte sensor, a torque compensation component, a drag compensation component, a cautery component, or a power source). In an aspect, the handle casing includes a user interface. In an aspect, the user interface includes at least one of an on/off switch, buttons, display screen, touchscreen, microphone, speakers, and the like for entering and receiving information.

Tissue Cutting System Including a Tissue Cutting Device and a Computing Component Described herein is a tissue cutting system including a tissue cutting device including a tethering component; an elongated flexible cutting component having a first end and a second end, the first end and the second end of the elongated flexible cutting component secured to the tethering component; at least one tether having a first end and a second end, the first end of the at least one tether attached to the elongated flexible cutting component at a position between the first end and the second end of the elongated flexible cutting component, the second end of the at least one tether operably coupled to the tethering component, the tethering component configured to at least one of extend and retract the at least one tether; and a motor operably coupled to the tethering component, the motor including circuitry configured to rotate the tethering component and the secured elongated flexible cutting component; and a computing component operably coupled to the tissue cutting device, the computing component including a processor and circuitry.

Figure 21:
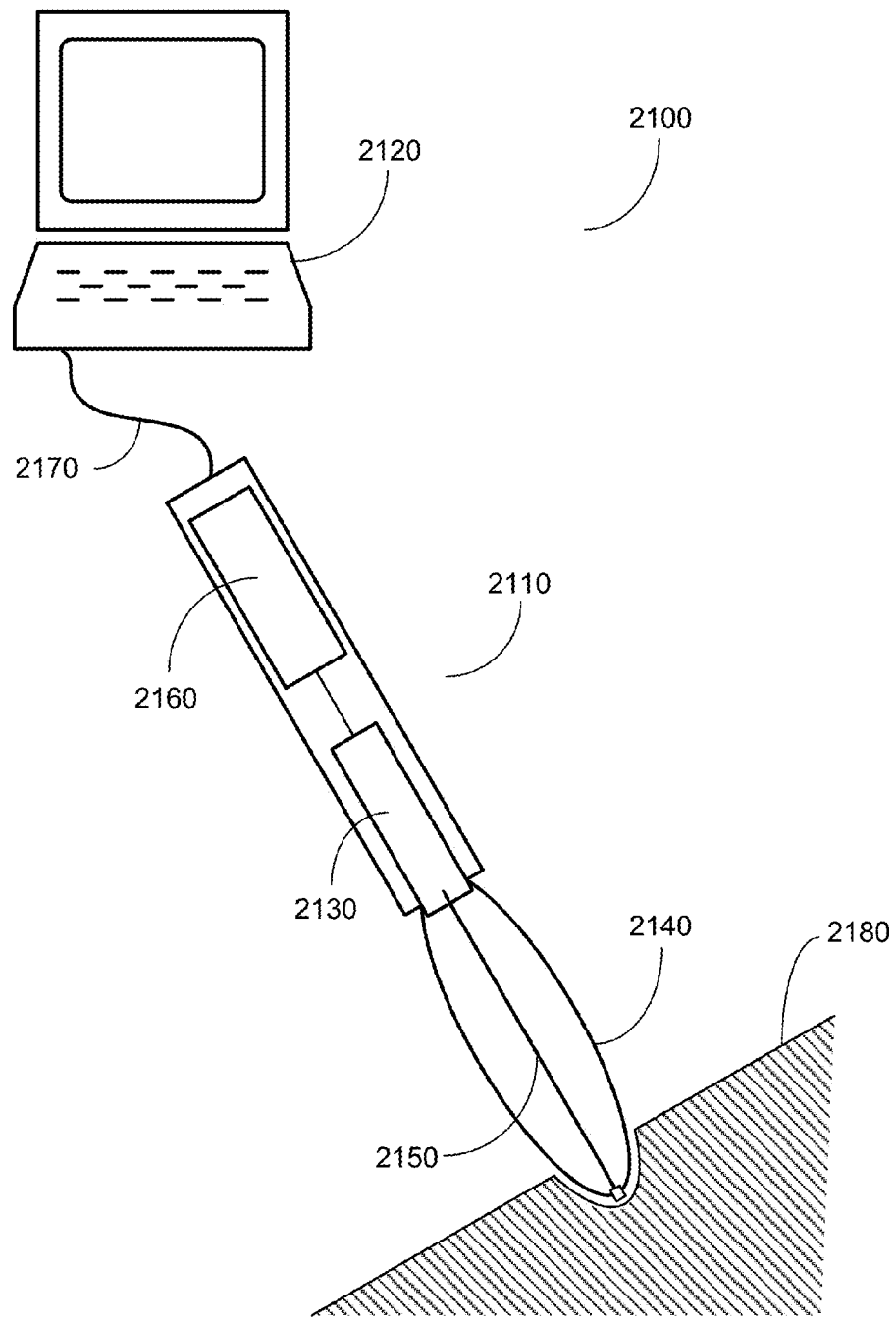
FIG. 21 is a schematic of a tissue cutting system.

FIG. 21 illustrates aspects of a tissue cutting system. System 2100 includes tissue cutting device 2110 and computing component 2120. Tissue cutting device 2110 includes a tethering component 2130; an elongated flexible cutting component 2140 having a first end and a second end, the first end and the second end of the elongated flexible cutting component 2140 secured to tethering component 2130; at least one tether 2150 having a first end and a second end, the first end of the tether 2150 attached to the elongated flexible cutting component 2140 at a position between the first end and the second end of the elongated flexible cutting component 2140, the second end of the tether 2150 operably coupled to the tethering component 2130, the tethering component 2130 including circuitry configured to extend and retract that at least one tether 2150; and a motor 2160 operably coupled to the tethering component 2130, motor 2160 including circuitry configured to rotate the tethering component 2130. System 2100 includes computing component 2120 operably coupled to tissue cutting device 2110, computing component 2120 including a processor and circuitry.

Tissue cutting device 2110 of tissue cutting system 2100 includes tethering component 2130. In an aspect, the tethering component includes circuitry configured to at least one of extend and retract the at least one tether. In an aspect, the tethering component of the tissue cutting device includes at least one rotatable component, e.g., a gear or pulley, the second end of the at least one tether of the tissue cutting device secured to the at least one rotatable component, the at least one rotatable component configured to extend and retract the at least one tether. In an aspect, the tethering component includes at least one clamp, the second end of the at least one tether passing through the at least one clamp. In an aspect, extension and retraction of the at least one tether by the tethering component changes a shape formed by the elongated flexible cutting component.

Tissue cutting device 2110 of tissue cutting system 2100 includes elongated flexible cutting component 2140. In an aspect, the elongated flexible cutting component of the tissue cutting device is formed from metal. In an aspect, the elongated flexible cutting component of the tissue cutting device is formed from at least one polymer. In an aspect, the elongated flexible cutting component of the tissue cutting device is formed from at least one natural fiber. In an aspect, the elongated flexible cutting component of the tissue cutting device is formed from at least one man-made fiber. In an aspect, the elongated flexible cutting component of the tissue cutting device is at least one of a flexible wire, strand, string, fiber, thread, or ribbon. In an aspect, the elongated flexible cutting component of the tissue cutting device includes a circular cross-section. In an aspect, the elongated flexible cutting component of the tissue cutting device includes a non-circular cross-section. In an aspect, the elongated flexible cutting component of the tissue cutting device includes at least one cutting edge. In an aspect, the elongated flexible cutting component of the tissue cutting device includes at least one serrated edge. In an aspect, the elongated flexible cutting component is replaceable.

In some embodiments, the tissue cutting device 2110 includes two or more elongated flexible cutting components. In an aspect, a first end and a second end of each of the two or more elongated flexible cutting components is attached to the tethering component 2130. In an aspect, each of the two or more elongated flexible cutting components is attached to at least one tether.

Tissue cutting device 2110 of tissue cutting system 2100 includes at least one tether 2150. In an aspect, the at least one tether of the tissue cutting device includes at least one flexible tether. For example, the at least one tether can include a wire or ribbon that is capable of being wound up and down by the tethering component. In an aspect, the at least one tether of the tissue cutting device includes at least one rigid tether. For example, that at least one tether can include a rod formed from metal or plastic that is capable of being pushed up and down by the tethering component. In an aspect, the at least one tether of the tissue cutting device is formed from metal, e.g., stainless steel or titanium. In an aspect, the at least one tether of the tissue cutting device is formed from at least one polymer, e.g., nylon or polyethylene. In an aspect, the at least one tether of the tissue cutting device is at least one of a wire, strand, string, fiber, thread, ribbon, or rod. In an aspect, the at least one tether of the tissue cutting device is replaceable.

In an aspect, the at least one tether of the tissue cutting device includes two or more first ends and one second end, each of the two or more first ends of the at least one tether attached to the elongated flexible cutting component at a position between the first and the second end of the elongated flexible cutting component, the second end of the at least one tether operably coupled to the tethering component. For example, the at least one tether can include a Y-shape. In an aspect, the at least one tether of the tissue cutting device includes at least one first end attached to the elongated flexible cutting component and at least one second end operably coupled to the tethering component. For example, the at least one tether can include an X-shape.

Tissue cutting device 2110 and computing component 2120 of tissue cutting system 2100 are operably connected through a communication link 2170. Communication link 2170 can include at least one of a wireless communication link, e.g., a radio transmission link, or a wired communication link, e.g., an electrical link. Tissue cutting device 2110 of system 2100 is shown in the process of cutting tissue 2180, the shape of the resected tissue dictated by the shape formed by the rotating elongated flexible cutting component.

In an aspect, computing component 2120 includes circuitry configured to control the tethering component 2130. For example, computing component 2120 can include circuitry configured to control at least one of extension and/or retraction of the at least one tether by the tethering component. In an aspect, the computing component includes circuitry configured to control at least one of speed and length of extension of the at least one tether by the tethering component. In an aspect, the computing component includes circuitry configured to control at least one of speed and length of retraction of the at least one tether by the tethering component. For example, computing component 2120 can include circuitry configured to control speed, distance traveled, and directionality of the tethering component.

In an aspect, computing component 2120 includes circuitry configured to control the motor 2160. For example, computing component 2120 can include circuitry configured to control rotational frequency of the motor. In an aspect, computing component 2120 includes circuitry configured to control at least one of extension and retraction of the at least one tether by the tethering component and the rotational frequency of the motor operably coupled to the tethering component to generate a cutting pattern. In an aspect, the cutting pattern is symmetric. For example, the cutting pattern can be a sphere or an oval. In an aspect, the cutting pattern is asymmetric. For example, securing the at least one tether closer to one end of the elongated flexible cutting component than to the other end results in an asymmetric cutting pattern upon retraction of the at least one tether.

In an aspect, computing component 2120 can take various forms or be part of an object, and can include, but is not limited to, a computer, a laptop computer, a personal electronic device, a dedicated computing device, a limited resource computing device, a wireless communication device, a mobile wireless communication device, a handheld electronic writing device, a tablet, a digital camera, a scanner, a cell phone, a PDA, an electronic tablet device, a printer, or any other like device that takes information as an input and gives it back to the end-users. Computing component 2120 can include a digital single processor, ASIC, microprocessor, or other type of processor operating on a system such as a personal computer, server, a router, or other device capable of processing data including network interconnection device. Other aspects of a computing component have been described above herein.

Figure 22:
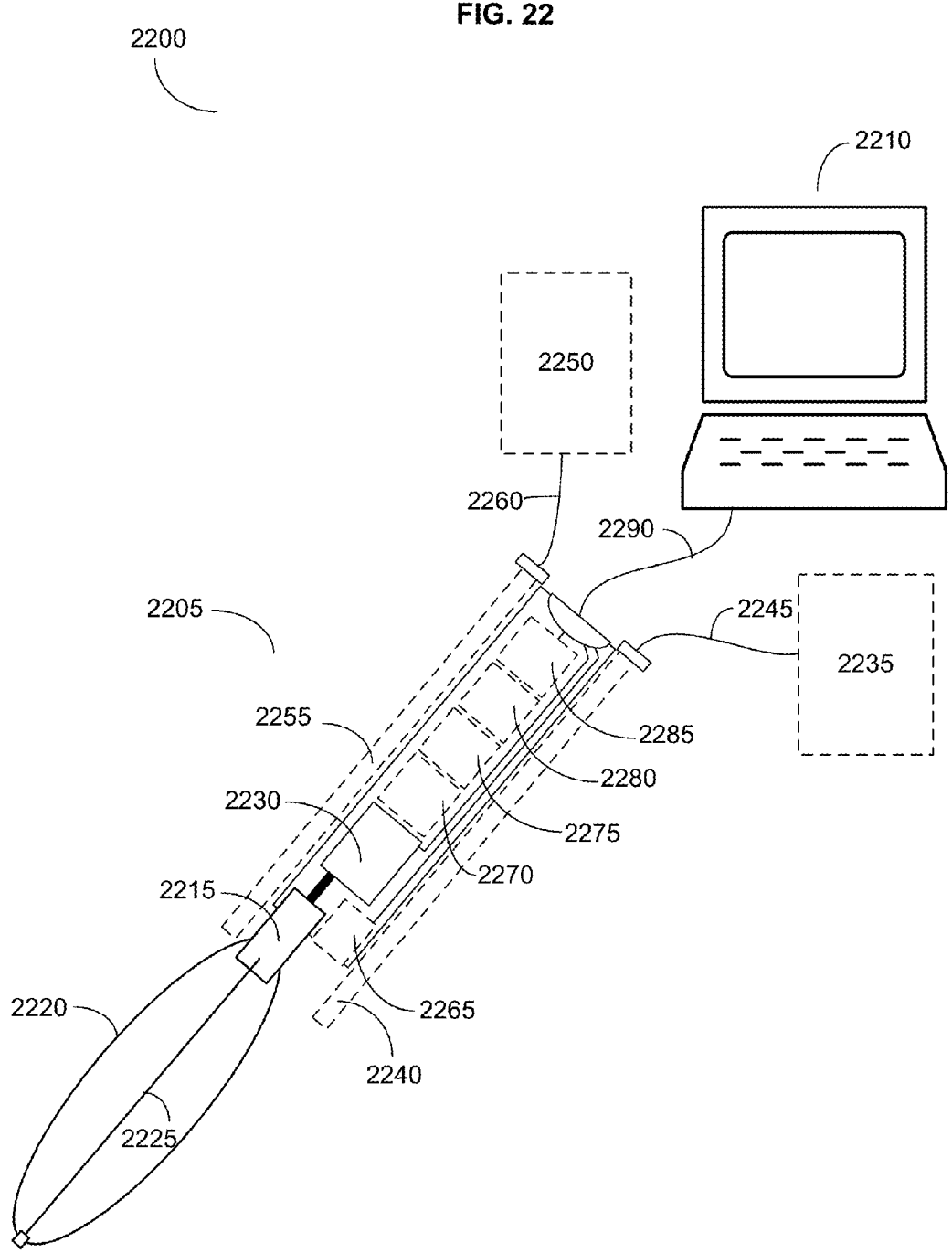
FIG. 22 illustrates further aspects of a tissue cutting system.

FIG. 22 illustrates further aspects of a tissue cutting system including a tissue cutting device and a computing component. Tissue cutting system 2200 includes tissue cutting device 2205 and computing component 2210. Tissue cutting device 2205 includes tethering component 2215, elongated flexible cutting component 2220, and at least one tether 2225. Tethering component 2215 is operably coupled to motor 2230, motor 2230 including circuitry configured to rotate tethering component 2215. Computing device 2210 is operably coupled to tissue cutting device 2205 through communication link 2290. Communication link 2290 can include a wireless or a wired communication link, non-limiting examples of which have been described above herein.

In some embodiments, system 2200 includes an aspiration component configured to aspirate tissue debris in proximity to the elongated flexible cutting component, the aspiration component including a vacuum source and an aspirator connected to the vacuum source. In an aspect, at least a portion of the aspiration component is incorporated into the tissue cutting device. In some embodiments, a non-limiting example of which is shown in FIG. 22, the aspiration component includes an external vacuum source 2235 attached to an aspirator 2240 through a flow conduit 2245. In an aspect, the aspirator of the aspiration component includes a suction tube positioned proximal to the elongated flexible cutting component of the tissue cutting device, the suction tube connected to the vacuum source. For example, the aspirator of the aspiration component can include a suction tube disposed in and defined by the at least one tether, e.g., a hollow rod. In some embodiments, the aspiration component is not physically attached to the tissue cutting device, but includes a separate aspirator held in a second hand or by a second individual.

In some embodiments, tissue cutting system 2200 includes an irrigation component configured to irrigate tissue in proximity to the elongated flexible cutting component, the irrigation component including a flow conduit attached to an irrigation fluid reservoir. In an aspect, the flow conduit includes an irrigation tube positioned proximal to the elongated flexible cutting component, the irrigation tube connected to the irrigation fluid reservoir. In an aspect, the flow conduit includes an irrigation tube positioned outside a cutting radius of the elongated flexible cutting component. In an aspect, the flow conduit includes an irrigation tube positioned inside a cutting radius of the elongated flexible cutting component. For example, the irrigation tube can be disposed in and defined by the at least one tether, e.g., a hollow rod. In an aspect, at least a portion of the irrigation component is incorporated into tissue cutting device 2205. In some embodiments, a non-limiting example of which is shown in FIG. 22, the irrigation component includes an external irrigation fluid reservoir 2250 attached to an irrigation tube 2255 through a flow conduit 2260. Irrigation fluid reservoir 2250 is configured to hold and controllably release at least one irrigation fluid. In an aspect, the at least one irrigation fluid includes at least one of saline, a buffer, a therapeutic agent, an antimicrobial agent, an anesthetic, or a coagulant agent. Non-limiting examples of irrigation fluids have been described above herein. In an aspect, the irrigation component is configured to wet at least a portion of the elongated flexible cutting component. In some embodiments, system 2200 includes an aspiration component and an irrigation component.

In some embodiments, tissue cutting system 2200 includes an image-capture device 2265. In an aspect, image-capture device 2265 is operably coupled to computing component 2210. Computing component 2225 includes circuitry configured to receive image data from the image-capture device 2265. In an aspect, the received image data include one or more images of a tissue in proximity to the elongated flexible cutting component 2220 of the tissue cutting device 2205. In an aspect, computing component 2210 includes circuitry configured to control at least one of the tethering component 2215 and/or the motor 2230 of tissue cutting device 2205 in response to the received image data. In an aspect, image-capture device 2265 includes an optical image-capture device. In an aspect, image-capture device 2265 includes an ultrasound image-capture device. In some embodiments, at least a portion of the image-capture device is incorporated into the tissue cutting device. In some embodiments, the image-capture device, for example a digital camera, is external to the tissue cutting device, but capable of transmitting image data to the computing component of the system. Non-limiting examples of image-capture device have been described above herein.

In some embodiments, tissue cutting system 2200 includes at least one analyte sensor 2270. The at least one analyte sensor is configured to sense a property of one or more analytes in an aspirate. In an aspect, at least a portion of the at least one analyte sensor is incorporated into the tissue cutting device, such as shown in the non-limiting example of FIG. 22. In an aspect, the at least one analyte sensor includes at least one of an optical sensor, a magnetic sensor, an electrical sensor, an acoustic sensor, or a chemical sensor. In an aspect, the at least one analyte sensor is configured to sense an optical property, a fluorescence property, a magnetic property, an electrical property, an electromagnetic property, an acoustic property, or a chemical property of the one or more analytes in the aspirate. In an aspect, the at least one analyte sensor 2270 is operably coupled to the computing component 2210, the computing component 2210 including circuitry configured to receive sensor input from the at least one analyte sensor 2270 and to control at least one of the tethering component 2215 and the motor 2230 of tissue cutting device 2205 in response to the received sensor input. Non-limiting examples of analyte sensors have been described above herein.

In some embodiments, tissue cutting system 2200 includes a drag compensation component 2275. In an aspect, drag compensation component 2275 includes circuitry configured to measure drag from the elongated flexible cutting component 2220 during rotation, the drag compensation component 2275 operably coupled to computing component 2210, the computing component 2210 including circuitry configured to control at least one of the tethering component and the motor of the tissue cutting device in response to the measured drag.

In some embodiments, tissue cutting system 2200 includes a torque compensation component 2280. The torque compensation component 2280 includes circuitry configured to prevent oscillation. In an aspect, the torque compensation component includes at least one counterweight. In an aspect, the at least one counterweight is extendable.

In some embodiments, tissue cutting system 2200 includes a cautery component 2285 to cauterize tissue. For example, the cautery component can be configured to cauterize tissue during and/or after a cutting procedure. In an aspect, cautery component 2285 is operably coupled to the elongated flexible cutting component 2220. For example, the elongated flexible cutting component can cauterize the tissue during the cutting procedure. In an aspect, cautery component 2285 includes an electrical cautery component. In an aspect, cautery component 2285 includes an optical cautery component. In an aspect, cautery component 2285 includes a thermal cautery component. In an aspect, cautery component 2285 includes a chemical cautery component. Non-limiting examples of a cautery component have been described above herein.

Tissue Cutting Device

In some embodiments, a tissue cutting device includes a central rotatable shaft having a first end and a second end; a motor operably coupled to the first end of the central rotatable shaft, the motor including circuitry configured to rotate the central rotatable shaft; a tethering component; and an elongated flexible cutting component having a first end and a second end, the first end of the elongated flexible cutting component secured to the central rotatable shaft at a position between the first end and the second end of the central rotatable shaft, the second end of the elongated flexible cutting component operably coupled to the tethering component, the tethering component including configured to at least one of extend and retract the elongated flexible cutting component; wherein the extension and retraction of the elongated flexible cutting component by the tethering component changes a shape formed by the elongated flexible cutting component.

In some embodiments, at least a portion of the elongated flexible cutting component between the first end and the second end of the elongated flexible cutting component is disposed in a lumen defined by the central rotatable shaft. For example, the second end of the elongated flexible cutting component can be fed through a lumen defined by the central rotatable shaft to attach to the tethering component. FIG. 23 illustrates aspects of a tissue cutting device including an elongated flexible cutting component disposed in a lumen defined by the central rotatable shaft. Tissue cutting device 2300 includes central rotatable shaft 2310 having a first end 2320 and a second end 2330. Tissue cutting device 2300 further includes motor 2340 operably coupled to the first end 2320 of the central rotatable shaft 2310. Motor 2340 includes circuitry configured to rotate central rotatable shaft 2310. Tissue cutting device 2300 includes tethering component 2350 and elongated flexible cutting component 2360.

Elongated flexible cutting component 2360 has a first end 2370 and a second end 2380. The first end 2370 of the elongated flexible cutting component 2360 is secured to the central rotatable shaft 2310 at a position between the first end 2320 and the second end 2330 of the central rotatable shaft 2310. At least a portion of the elongated flexible cutting component 2360 between the first end 2370 and the second end 2380 of the elongated flexible cutting component 2360 is disposed in a lumen 2390 defined by the central rotatable shaft. The second end 2380 of the elongated flexible cutting component 2360 is operably coupled to the tethering component 2350. The tethering component 2350 is configured to at least one of extend and retract the elongated flexible cutting component 2360 to change a shape formed by the elongated flexible cutting component 2360.

In some embodiments, at least a portion of the elongated flexible cutting component between the first end and the second end of the elongated flexible cutting component extends past a rotatable element associated with the central rotatable shaft. In an aspect, the rotatable element includes a pulley. In an aspect, the rotatable element includes a fly wheel. In an aspect, the rotatable element is attached to the exterior of the central rotatable shaft. FIG. 24 illustrates an aspect of a tissue cutting device including a rotatable element. Tissue cutting device 2400 includes central rotatable shaft 2410 having a first end 2420 and a second end 2430. Tissue cutting device 2400 further includes motor 2440 operably coupled to the first end 2420 of the central rotatable shaft 2410. Motor 2440 includes circuitry configured to rotate central rotatable shaft 2410. Tissue cutting device 2400 includes tethering component 2450 and elongated flexible cutting component 2460. Elongated flexible cutting component 2460 has a first end 2470 and a second end 2480. The first end of the elongated flexible cutting component is secured to the central rotatable shaft at a position between the first end and the second end of the central rotatable shaft. In the non-limiting example shown in FIG. 24, first end 2470 of the elongated flexible cutting component 2460 is secured to the central rotatable shaft 2410 at a position in proximity to the second end 2430 of the central rotatable shaft 2410. At least a portion of the elongated flexible cutting component 2460 between the first end 2470 and the second end 2480 of the elongated flexible cutting component 2460 extends past a rotatable element 2490 on the central rotatable shaft 2460. The second end 2480 of the elongated flexible cutting component 2460 is operably coupled to the tethering component 2450. The tethering component 2450 is configured to at least one of extend and retract the elongated flexible cutting component 2460 to change a shape formed by the elongated flexible cutting component 2460.

In an aspect, the elongated flexible cutting component forms a D-shape. In an aspect, the elongated flexible cutting component attached at a first end to the central rotatable shaft and at the second end to the tethering component and is at least partially disposed in a lumen defined by the central rotatable shaft forms a D-shape. In an aspect, an elongated flexible cutting component attached at a first end to the central rotatable shaft and at a second end to the tethering component and a portion of which extends past a rotatable element on the central rotatable shaft forms a D-shape. In an aspect, the tethering component, by either extending or retracting the elongated flexible cutting component, controls the D-shape formed by the elongated flexible cutting component. For example, the D-shape can be lengthened and narrowed as the tethering component extends the elongated flexible cutting component. For example, the D-shape can be shortened and widened as the tethering component retracts the elongated flexible cutting component.

In an aspect, the shape formed by the elongated flexible cutting component is fixed. For example, the tethering component can extend or retract the elongated flexible cutting component to a set position that is locked into place prior to a cutting procedure to create a defined length of elongated flexible cutting component, the radius of the shape formed by the elongated flexible cutting component remaining constant and creating a symmetrical cutting pattern.

In an aspect, the shape formed by the elongated flexible cutting component varies through the course of the resection. For example, the radius of the rotating elongated flexible cutting component can vary as the tissue cutting device is moved into the tissue, with a small cutting radius at the point of entering the tissue and a larger cutting radius once the target tissue for resection has been reached.

FIGS. 25A and 25B illustrate changes in the shape formed by the elongated flexible cutting component as well as the tissue cutting pattern in response to extending and retracting the elongated flexible cutting component. FIG. 25A shows tissue cutting device 2300 at a first time point relative to tissue 2500. Tissue cutting device 2300 includes central rotatable shaft 2310, motor 2340, tethering component 2350, and elongated flexible cutting component 2360. At least a portion of the elongated flexible cutting component 2360 between the first end and the second end of the elongated flexible cutting component 2360 is disposed in a lumen 2390 defined by the central rotatable shaft 2310. Tissue cutting device 2300 is shown cutting into tissue 2500 and target tissue mass 2510. Tethering component 2350, shown in this example as a rotatable reel 2520, has retracted elongated flexible cutting component 2360 to a first position that creates resected space 2530 as central rotatable shaft 2310 and attached elongated flexible cutting component 2360 are rotated by motor 2340. As the elongated flexible cutting component 2360 rotates, it cuts away at tissue 2500 in a pattern dependent upon the shape formed by the elongated flexible cutting component 2360. FIG. 25B shows tissue cutting device 2300 at a second time point relative to tissue 2500. At this point, central rotatable shaft 2310 is shown further into tissue 2500. Tethering component 2350 has extended elongated flexible cutting component 2360 to a second position that creates resected space 2540 as central rotatable shaft 2310 and attached elongated flexible cutting component 2360 are rotated by motor 2340. In this example, tissue mass 2510 has been removed, leaving resected space 2540.

In an aspect, a tissue cutting device such as described herein is used for minimally invasive surgery to cut and resect tissue. In an aspect, the tissue cutting device is inserted into a tissue of a patient. In some embodiments, the distal portion of the tissue cutting device (e.g., the second end of the central rotatable shaft) is adapted to pierce tissue. In other embodiments, the tissue cutting device is inserted into a previously established surgical incision (e.g., a 0.5 cm to 2 cm incision). In an aspect, the tissue cutting device is inserted into a body lumen (e.g., a blood vessel, gastrointestinal tract, vagina, rectum, airway, ureter, or urethra).

A tissue cutting device such as described herein can enter tissue by any of a number of routes including, but not limited to, transabdominal, transperineal, transcutaneous, transvascular, transurethral, transureteral, transoral, transvaginal, and transrectal routes of insertion. A wide range of tissue can be cut and resected including but not limited to prostatic tissue, kidney tissue, liver tissue, uterine tissue, bladder tissue, and brain tissue. In an aspect, the tissue to be cut and resected is benign tissue (e.g., fibrotic tissue in uterus or prostate). In an aspect, the tissue to be cut and resected is malignant tissue (e.g., a solid tumor).

In an aspect, the tissue cutting device is sized for placement into cannula or trocar. For example, the central rotatable shaft and elongated flexible cutting component of the tissue cutting device may be extended from or retracted into a cannula or trocar configured for performing minimally invasive surgery.

A tissue cutting device such as described in FIGS. 23 and 24 includes a tethering component configured to at least one of extend and retract the elongated flexible cutting component. In an aspect, the tethering component includes a manual tethering component. For example, the tethering component can include a fastening device for holding the elongated flexible cutting component to a specific length. For example, the fastening device can include a clamping device, a holding device, a clinching device, a cinching device, an anchoring device, a hitching device, or a securing device. For example, the fastening device can include a clamp, a snap, a screw, or a pin. For example, the tethering component can include a "pull-through" function in which the elongated flexible cutting component (e.g., a wire, string, strand, fiber, thread, or ribbon) is pulled through a closable fastening device until the appropriate length is reached and the closable fastening device is closed.

In an aspect, the tethering component includes a securing device, the securing device configured to secure the elongated flexible cutting component at a specified length. For example, the tethering component can include a lockable clamp. For example, the tethering component can include at least one lockable gear with a gripping surface (e.g., teeth, abrasive, or adhesive) designed to interact with the elongated flexible cutting component and prevent slippage. For example, the tethering component can include a hinged or pivoted device, e.g., a pawl, adapted to fit into a notch of a ratchet wheel to impart extension and/or retraction or to prevent extension and/or retraction.

In some embodiments, the tethering component includes circuitry configured to extend and retract the elongated flexible cutting component. For example, the tethering component can include a ratchet or gears configured to controllably extend and/or retract the elongated flexible cutting component. For example, the tethering component can include a motorized ratchet or gears configured to controllably extend and/or retract the elongated flexible cutting component. In an aspect, the tethering component includes circuitry configured to either extend or retract the elongated flexible cutting component. For example, the tethering component can include a locking component and a retraction component, the elongated flexible cutting component extended by centrifugal force of rotation, locked after sufficient extension, and retracted by the retraction component. In an aspect, the tethering component includes at least one rotatable component, the second end of the elongated flexible cutting component secured to the at least one rotatable component, the at least one rotatable component configured to at least one of extend and retract the elongated flexible cutting component. For example, the tethering component can include a rotatable gear to which the second end of the elongated flexible cutting component is secured and a second motor including circuitry configured to rotate the rotatable gear to at least one of extend and retract the attached elongated flexible cutting component. For example, the at least one rotatable component can be configured to extend and/or retract the attached elongated flexible cutting component In an aspect, the tethering component is attached to the central rotatable shaft. For example, the tethering component can include a rotatable reel associated with the central rotatable shaft. In an aspect, the tethering component is disposed in a lumen defined by the central rotatable shaft. In an aspect, the tethering component is configured to rotate with the central rotatable shaft.

A tissue cutting device such as described in FIGS. 23 and 24 includes an elongated flexible cutting component. In an aspect, the elongated flexible cutting component is formed from metal. In an aspect, the elongated flexible cutting component is formed from at least one polymer. In an aspect, the elongated flexible cutting component is formed from at least one natural fiber. In an aspect, the elongated flexible cutting component is formed from at least one man-made fiber. In an aspect, the elongated flexible cutting component is at least one of a flexible wire, strand, string, fiber, thread, or ribbon. In an aspect, the elongated flexible cutting component includes a non-circular cross-section. In an aspect, the elongated flexible cutting component includes at least one cutting edge. In an aspect, the elongated flexible cutting component includes at least one serrated edge. In an aspect, the elongated flexible cutting component is replaceable.

In some embodiments, a tissue cutting device includes two or more elongated flexible cutting components. In an aspect, a first end of each of the two or more elongated flexible cutting components is secured to the central rotatable shaft and the second end of each of the two or more elongated flexible cutting components is operably coupled to the tethering component.

In some embodiments, a tissue cutting device such as described in FIGS. 23 and 24 includes an aspiration component configured to aspirate tissue debris in proximity to the central rotatable shaft. In an aspect, the aspiration component includes a vacuum source and an aspirator connected to the vacuum source. FIGS. 26-28 illustrate aspects of a tissue cutting device including an aspiration component. In an aspect, the aspirator of the aspiration component includes a suction tube positioned proximal to the central rotatable shaft of the tissue cutting component, the suction tube connected to the vacuum source. FIG. 26 illustrates a non-limiting embodiment of a tissue cutting device including a suction tube. FIG. 26 shows tissue cutting device 2600 including central rotatable shaft 2410 operably coupled to motor 2440. Elongated flexible cutting component 2460 is shown attached at a first end to central rotatable shaft 2410 and at a second end to tethering component 2450. At least a portion of elongated flexible cutting component 2460 extends past rotatable element 2490. Tissue cutting device 2600 further includes vacuum source 2610. Vacuum source 2610 is in fluid communication with suction tube 2620. Suction tube 2620 extends from handle casing 2630 into a region in proximity to central rotatable shaft 2410 and is configured to aspirate tissue debris resected by the rotating elongated flexible cutting component 2460.

In an aspect, the aspirator includes a suction lumen disposed in and defined by the central rotatable shaft, the suction lumen connected to the vacuum source and in fluid communication with one or more openings defined by the central rotatable shaft. In an aspect, the one or more openings defined by the central rotatable shaft include a single opening. For example, the one opening can be position at or near the end of the central rotatable shaft. FIG. 27 illustrates a non-limiting embodiment of a tissue cutting device including a suction lumen and one opening defined by the central rotatable shaft. FIG. 27 shows tissue cutting device 2700 including central rotatable shaft 2710 operably coupled to motor 2440. Elongated flexible cutting component 2460 is shown attached at a first end to central rotatable shaft 2710 and at a second end to tethering component 2450. At least a portion of elongated flexible cutting component 2460 extends past rotatable element 2490. Tissue cutting device 2700 further includes vacuum source 2720. Central rotatable shaft 2710 further includes a suction lumen 2730 disposed in and defined by central rotatable shaft 2710. Suction lumen 2730 is connected to vacuum source 2720 and is in fluid communication with an opening 2740 defined by central rotatable shaft 2710. In this non-limiting embodiment, tissue cutting device 2700 is configured to aspirate tissue debris generated by the rotation of elongated flexible cutting component 2460 into opening 2740, aspirate the debris through suction lumen 2730, and into vacuum source 2720.

In an aspect, the one or more openings defined by the central rotatable shaft are positioned along the length of the central rotatable shaft. For example, the tissue cutting device can include a single opening somewhere along the length of the central rotatable shaft. For example, the tissue cutting device can include a plurality of openings positioned along the length of the central rotatable shaft. FIG. 28 illustrates a non-limiting embodiment of a tissue cutting device include a suction lumen and a plurality of openings defined by the central rotatable shaft. FIG. 28 shows tissue cutting device 2800 including central rotatable shaft 2810 operably coupled to motor 2440. Elongated flexible cutting component 2460 is shown attached at a first end to central rotatable shaft 2810 and at a second end to tethering component 2450. At least a portion of elongated flexible cutting component 2460 extends past rotatable element 2490. Tissue cutting device 2800 further includes vacuum source 2820. Central rotatable shaft 2810 further includes a suction lumen 2830 disposed in and defined by central rotatable shaft 2810. Suction lumen 2830 is connected to vacuum source 2820 and is in fluid communication with openings 2840 defined by and positioned along the length of central rotatable shaft 2810. In this non-limiting embodiment, tissue cutting device 2800 is configured to aspirate tissue debris generated by the rotation of elongated flexible cutting component 2460 into openings 2840, aspirate the debris through suction lumen 2830, and into vacuum source 2820.

In an aspect, the vacuum source is at least partially contained within a hand-held housing of the tissue cutting device. For example, vacuum source can include any of a number of small, commercially available mini vacuum pumps sized for use in small appliances (from, e.g., Vaccon Co, Inc., Medway, Mass.; Hargraves Technology Corp, Mooresville, N.C.). In an aspect, the vacuum source is external to the tissue cutting device, e.g., a large vacuum pump, but connected, e.g., by a fitting, luer, or connection, to the aspirator through a vacuum conduit, e.g., a hose or tubing. In an aspect, the external vacuum source includes an aspirator pump, e.g., a water aspirator.

Figure 29:
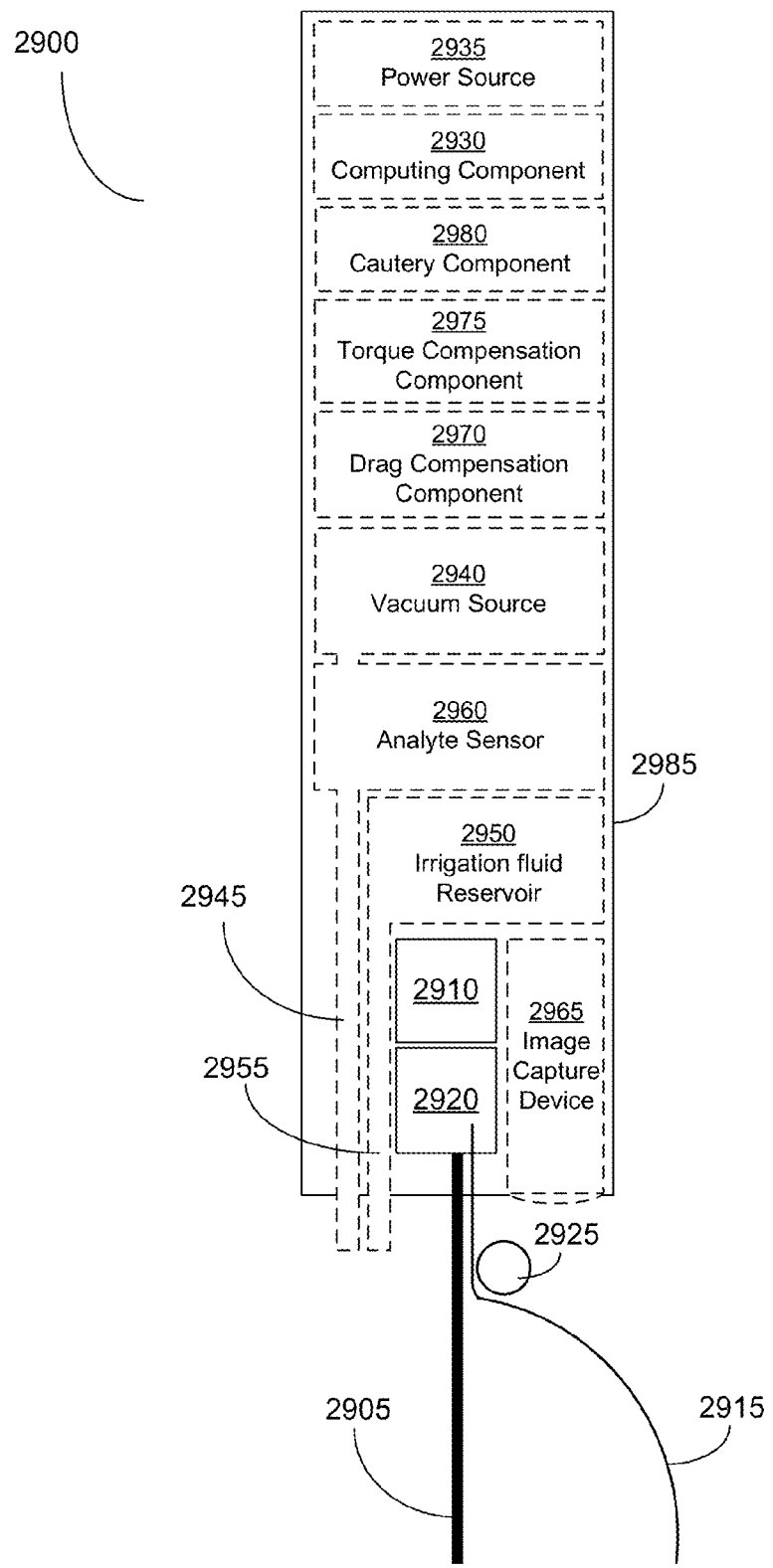
FIG. 29 illustrates further aspects of a tissue cutting device.

FIG. 29 illustrates further aspects of a tissue cutting device such as shown in FIGS. 23 and 24. Tissue cutting device 2900 includes central rotatable shaft 2905 operably coupled to motor 2910 and elongated flexible cutting component 2915 secured at one end to the central rotatable shaft 2905 (not shown in this view) and at the second end to tethering component 2920. At least a portion of elongated flexible cutting component 2915 extends past rotatable element 2925.

Tissue cutting device 2900 further includes computing component 2930 including a processor and circuitry. Non-limiting aspects of a computing component have been described above herein. In an aspect, the computing component 2930 is operably coupled to at least one of the motor 2910 and the tethering component 2920. In an aspect, computing component 2930 includes circuitry configured to control the motor. For example, the computing component can include circuitry configured to control to rotational rate or frequency of the motor. In an aspect, the computing component 2930 includes circuitry configured to control the tethering component. In an aspect, the computing component 2930 includes circuitry configured to control at least one of extension and retraction of the elongated flexible cutting component by the tethering component. For example, the computing component can include circuitry configured to control extension and/or retraction of the elongated flexible cutting component by the tethering component. For example, the computing component can include circuitry configured to control at least one of speed and length of extension of the elongated flexible cutting component by the tethering component. For example, the computing component can include circuitry configured to control at least one of speed and length of retraction of the elongated flexible cutting component. For example, the computing component can include circuitry configured to control speed, distance traveled, and directionality of the tethering component. In an aspect, computing component 2930 is operably coupled to one or more other components of tissue cutting device 2900.

Tissue cutting device 2900 further includes power source 2935. For example, tissue cutting device 2900 can include an electrical cord for use with an electrical outlet. For example, tissue cutting device 2900 can include one or more batteries. Non-limiting examples of power sources have been described above herein.

In some embodiments, tissue cutting device 2900 includes an aspiration component configured to aspirate tissue debris in proximity to central rotatable shaft 2910. The aspiration component includes a vacuum source and an aspirator connected to the vacuum source. In some embodiments, as shown in FIG. 29, the aspiration component includes vacuum source 2940 and aspirator 2945 connected to vacuum source 2940, aspirator 2945 including a suction lumen positioned proximal to central rotatable shaft 2910. In some embodiments, such as shown in FIGS. 27 and 28, the aspirator includes a suction lumen disposed in and defined by the central rotatable shaft, the suction lumen connected to the vacuum source and in fluid communication with one or more openings defined by the central rotatable shaft.

In some embodiments, tissue cutting device 2900 includes an irrigation component configured to irrigate tissue in proximity to the central rotatable shaft. The irrigation component includes an irrigation fluid reservoir and a flow conduit. In some embodiments, such as shown in FIG. 29, the flow conduit includes an irrigation tube 2955 positioned proximal to the central rotatable shaft 2910, the irrigation tube connected to the irrigation fluid reservoir 2950. In some embodiments, the flow conduit includes an irrigation lumen disposed in and defined by the central rotatable shaft, the irrigation lumen connected to the irrigation fluid reservoir and in fluid communication with one or more openings defined by the central rotatable shaft. In an aspect, the one or more openings defined by the central rotatable shaft are positioned along the length of the central rotatable shaft. In an aspect, irrigation fluid reservoir 2950 is configured to hold and controllably release at least one irrigation fluid. In an aspect, the at least one irrigation fluid includes at least one of saline, a buffer, a therapeutic agent, an antimicrobial agent, an anesthetic, or a coagulant agent. In an aspect, the irrigation component is configured to wet the elongated flexible cutting component. For example, the irrigation component can be configured to wet the elongated flexible cutting component with an irrigation fluid before, during, and/or after a cutting procedure. In some embodiments, tissue cutting device 2900 includes an aspiration component and an irrigation component.

In some embodiments, tissue cutting device 2900 includes at least one analyte sensor 2960. In an aspect, the at least one analyte sensor includes at least one of an optical sensor, a magnetic sensor, an electrical sensor, an acoustic sensor, or a chemical sensor. Non-limiting examples of analyte sensors have been described above herein. In an aspect, the at least one analyte sensor is configured to sense a property of one or more analytes in an aspirate. In an aspect, the at least one analyte sensor is configured to sense an optical property, a fluorescence property, a magnetic property, an electrical property, an electromagnetic property, an acoustic property, or a chemical property of the one or more analytes in the aspirate. In some embodiments, such as shown in FIG. 29, the at least one analyte sensor 2960 is in fluid communication with the aspirator 2945 and/or the vacuum source 2940. For example, the at least one analyte sensor can be position to sense a property of an aspirate as it flows through the aspirator and into the vacuum source. In an aspect, the at least one analyte sensor is configured to sense in situ a property of the target tissue before, during, and/or after the resection procedure. For example, the at least one analyte sensor can be configured to sense in situ an optical property, a fluorescence property, a magnetic property, an electrical property, electromagnetic property, acoustic property, or chemical property of the target tissue before, during, and/or after the resection procedure.

In some embodiments, tissue cutting device 2900 includes an image-capture device 2965. The image-capture device 2965 is operably coupled to a computing component 2930, the computing component 2930 including circuitry configured to receive image data from image-capture device 2965. In an aspect, the image data includes one or more images of tissue in proximity to the central rotatable shaft and/or the elongated flexible cutting component before, during, and/or after a resection procedure. In an aspect, image-capture device 2965 includes an optical image-capture device. For example, image-capture device 2965 can include a digital camera, a fluoroscope, or a laparoscope. In an aspect, image-capture device 2965 includes an ultrasound image-capture device.

In some embodiments, tissue cutting device 2900 includes a drag compensation component 2970. For example, the drag compensation component can include at least one spar and one or more stays to compensate for drag associated with the rotating elongated flexible cutting component, a non-limiting example of which is illustrated in FIGS. 12A and 12B. In an aspect, the drag compensation component 2970 includes circuitry configured to measure drag from the elongated flexible cutting component during rotation. For example, the drag compensation component can include a transceiver and one or more reflectors for use in measuring drag associated with the rotating elongated flexible cutting component, a non-limiting example of which is shown in FIGS. 13A-C. In an aspect, a drag compensation component 2970 is operably coupled to a computing component 2930, the computing component 2930 including circuitry configured to control at least one of the motor 2910 and the tethering component 2920 in response to the measured drag. For example, the computing component can include circuitry configured to control the motor and/or the tethering component in response to the measured drag of the elongated flexible cutting component.

In some embodiments, tissue cutting device 2900 includes a torque compensation component 2975. In an aspect, the torque compensation component includes circuitry configured to prevent oscillation. For example, the torque compensation component can include circuitry configured to prevent oscillation when executing asymmetric cutting patterns. In an aspect, the torque compensation component includes at least one counterweight. For example, the torque compensation component can include at least one counterweight associated with the central rotatable shaft and configured to pivot in response to changes in the shape formed by the elongated flexible cutting component. In an aspect, the at least one counterweight is extendable. Non-limiting examples of torque compensation components including counterweights are illustrated in FIGS. 10A-C and FIGS. 11A-C.

In some embodiments, tissue cutting device 2900 includes a cautery component 2980. In an aspect, the cautery component is configured to cauterize tissue. For example, the cautery component can be configured to cauterize tissue during and/or after a cutting procedure. In an aspect, the cautery component is operably coupled to the elongated flexible cutting component. For example, the elongated flexible cutting component can be electrified and/or heated to cauterize while cutting. The cautery component includes at least one of an electrical cautery component, an optical cautery component, a thermal cautery component, or a chemical cautery component.

In an aspect, tissue cutting device 2900 further includes a handle casing 2985, the handle casing covering at least a portion of the motor, the handle casing including a user interface. In an aspect, the handle casing is sized for use with a single hand. In an aspect, the handle casing further covers one or more other components of the tissue cutting device (e.g., the tethering component, a computing component, an aspiration component, an irrigation component, an image-capture device, at least one analyte sensor, a torque compensation component, a drag compensation component, a cautery component, or a power source). In an aspect, the handle casing includes a user interface. In an aspect, the user interface includes at least one of an on/off switch, buttons, display screen, touchscreen, microphone, speakers, and the like for entering and receiving information.

Tissue Cutting System

Described herein are embodiments of a tissue cutting system including a tissue cutting device and a computing component, the tissue cutting device including a central rotatable shaft having a first end and a second end; a motor operably coupled to the first end of the central rotatable shaft, the motor including circuitry configured to rotate the central rotatable shaft; a tethering component; and an elongated flexible cutting component having a first end and a second end, the first end of the elongated flexible cutting component secured to the central rotatable shaft at a position between the first and the second end of the central rotatable shaft, the second end of the elongated flexible cutting component operably coupled to the tethering component, the tethering component configured to at least one of extend and retract the elongated flexible cutting component; and the computing component operably coupled to the tissue cutting device, the computing component including a processor and circuitry.

Figure 30:
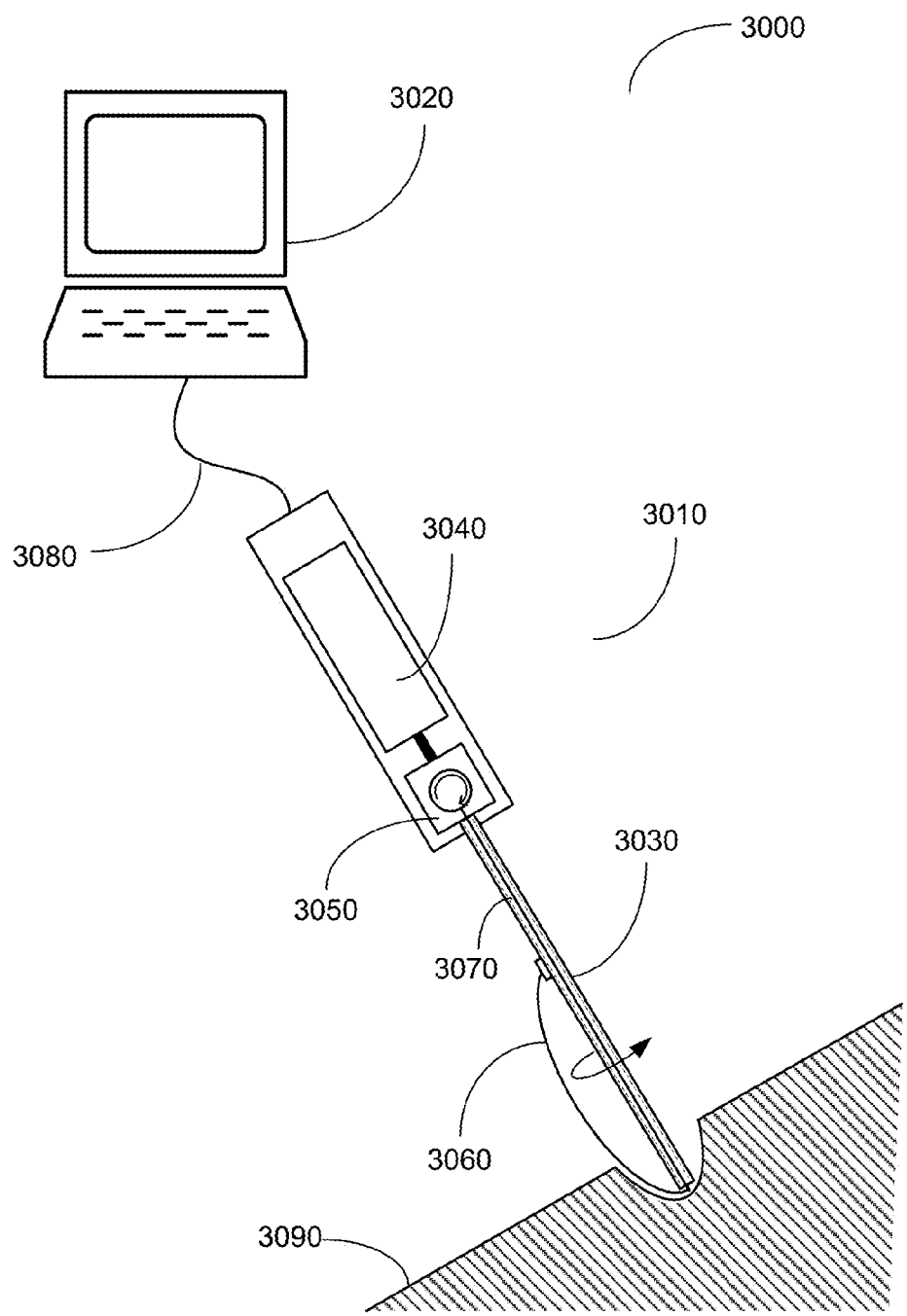
FIG. 30 is a schematic of a tissue cutting system.

FIG. 30 illustrates aspects of a tissue cutting system. System 3000 includes tissue cutting device 3010 and computing component 3020. Tissue cutting device 3010 includes central rotatable shaft 3030 operably connected at one end to motor 3040. Tissue cutting device 3010 further includes elongated flexible cutting component 3060 secured at a first end to central rotatable shaft 3030 and at a second end to tethering component 3050. In some embodiments, at least a portion of elongated flexible cutting component 3060 of the tissue cutting device 3010 between the first end and the second end of the elongated flexible cutting component 3060 is disposed in a lumen 3070 defined by the central rotatable shaft 3030 of the tissue cutting device. In some embodiments, at least a portion of the elongated flexible cutting component of the tissue cutting device between the first and the second end of the elongated flexible cutting component extends past a rotatable element on the central rotatable shaft of the tissue cutting device. In an aspect, the rotatable element includes a pulley or a flywheel. In an aspect, the rotatable element is attached to the exterior of the central rotatable shaft.

Tissue cutting device 3010 of tissue cutting system 3000 includes tethering component 3050. In an aspect, the tethering component of the tissue cutting device includes circuitry configured to at least one of extend and retract the elongated flexible cutting component. In an aspect, extension and retraction of the elongated flexible cutting component by the tethering component of the tissue cutting device changes a shape formed by the elongated flexible cutting component. For example, extension of the elongated flexible cutting component lengthens and narrows a D-shape formed by the elongated flexible cutting component. For example, retraction of the elongated flexible cutting component shortens and widens a D-shape formed by the elongated flexible cutting component. In an aspect, the tethering component of the tissue cutting device includes at least one rotatable component, the second end of the elongated flexible cutting component of the tissue cutting device secured to the at least rotatable component, the at least one rotatable component configured to at least one of extend and retract the elongated flexible cutting component. In an aspect, the tethering component of the tissue cutting device includes a securing device, the securing device to secure the elongated flexible cutting component to a length. In an aspect, the tethering component is attached to the central rotatable shaft. In an aspect, the tethering component of the tissue cutting device is disposed in a lumen defined by the central rotatable shaft. In an aspect, the tethering component of the tissue cutting device is configured to rotate with the central rotatable shaft.

Tissue cutting device 3010 of tissue cutting system 3000 includes elongated flexible cutting component 3060. In an aspect, the elongated flexible cutting component of the tissue cutting device is formed from metal. In an aspect, the elongated flexible cutting component of the tissue cutting device is formed from at least one polymer. In an aspect, the elongated flexible cutting component of the tissue cutting device is formed from at least one natural fiber. In an aspect, the elongated flexible cutting component of the tissue cutting device is formed from at least one man-made fiber. In an aspect, the elongated flexible cutting component of the tissue cutting device is at least one of a flexible wire, strand, string, fiber, thread, or ribbon. In an aspect, the elongated flexible cutting component of the tissue cutting device includes a non-circular cross-section. In an aspect, the elongated flexible cutting component of the tissue cutting device includes at least one cutting edge. In an aspect, the elongated flexible cutting component of the tissue cutting device includes at least one serrated edge. In an aspect, the elongated flexible cutting component of the tissue cutting device is replaceable. In an aspect, the tissue cutting device includes two or more elongated flexible cutting components.

Tissue cutting device 3010 and computing component 3020 are operably connected through a communication link 3080. Communication link 3080 can include at least one of a wireless communication link, e.g., Bluetooth or other radio transmission link, or a wired communication link, e.g., an electrical link. Tissue cutting device 3010 of system 3000 is shown in the process of cutting tissue 3090, the shape of the resected tissue dictated by the shape formed by the rotating elongated flexible cutting component. In an aspect, the computing component 3020 includes circuitry configured to control the motor 3040. For example, computing component 3020 can include circuitry configured to control the rotational frequency of motor 3040, e.g., the speed at which the central rotatable shaft is rotated. In an aspect, the computing component 3020 includes circuitry configured to control the tethering component 3050. In an aspect, computing component 3020 includes circuitry configured to control at least one of extension and retraction of the elongated flexible cutting component 3060 by tethering component 3050. For example, the computing component can include circuitry configured to control at least one of speed and length of extension of the elongated flexible cutting component by the tethering component. For example, the computing component can include circuitry configured to control at least one of speed and length of retraction of the elongated flexible cutting component by the tethering component. In an aspect, the computing component 3020 includes circuitry configured to control at least one of extension and retraction of the elongated flexible cutting component 3060 by the tethering component 3050 and the rotational frequency of the motor 3040 operably coupled to the central rotatable shaft 3030 to generate a cutting pattern. In an aspect, the cutting pattern is symmetrical. For example, the rotational frequency of the motor and the length of the elongated flexible cutting component remain constant through a 360 degree rotational event. In an aspect, the cutting pattern is asymmetrical. For example, the rotational frequency of the motor and the length of the elongated flexible cutting component vary through a 360 degree rotational event.

In an aspect, computing component 3020 can take various forms or be part of an object, and can include, but is not limited to, a computer, a laptop computer, a personal electronic device, a dedicated computing device, a limited resource computing device, a wireless communication device, a mobile wireless communication device, a handheld electronic writing device, a tablet, a digital camera, a scanner, a cell phone, a PDA, an electronic tablet device, a printer, or any other like device that takes information as an input and gives it back to the end-users. Computing component 3020 can include a digital single processor, ASIC, microprocessor, or other type of processor operating on a system such as a personal computer, server, a router, of other device capable of processing data including network interconnection device. Other aspects of a computing component have been described above herein.

Figure 31:
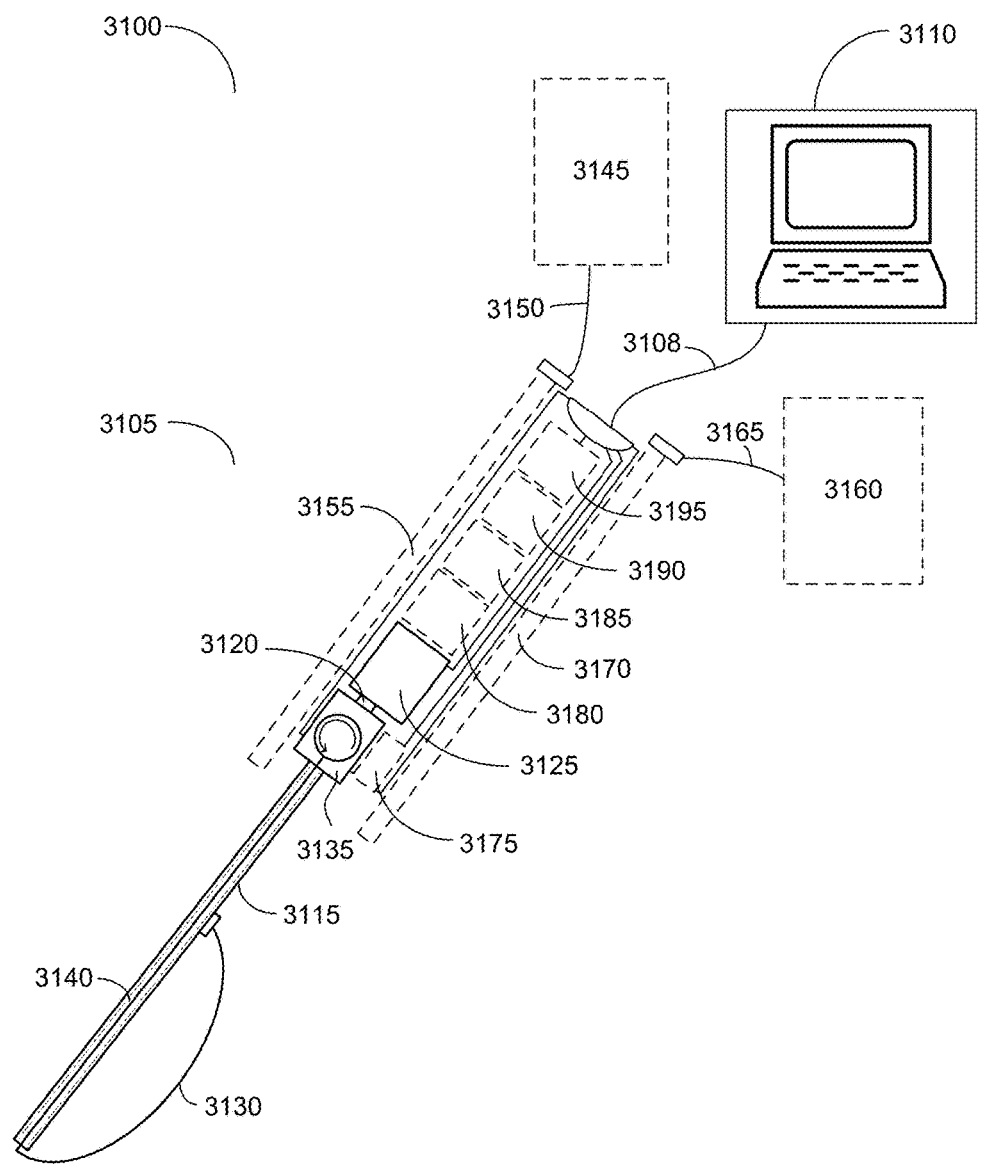
FIG. 31 illustrates further aspects of a tissue cutting system.

FIG. 31 illustrates further aspects of a tissue cutting system. In an aspect, system 3100 includes tissue cutting device 3105 and computing component 3110. Computing component 3110 is operably coupled to tissue cutting device 3105 through a communication link 3108, e.g., a wireless or wired communication link. Tissue cutting device 3105 includes central rotatable shaft 3115 operably coupled at a first end 3120 to motor 3125. Tissue cutting device 3105 further includes elongated flexible cutting component 3130 secured at a first end to the central rotatable shaft 3115 and at a second end to tethering component 3135. In this non-limiting embodiment, at least a portion of elongated flexible cutting component 3130 of tissue cutting device 3105 between the first and the second end of the elongated flexible cutting component 3130 is disposed in a lumen 3140 defined by the central rotatable shaft 3115.

In some embodiments, tissue cutting system 3100 includes an aspiration component configured to aspirate tissue debris in proximity to the central rotatable shaft 3115 of the tissue cutting device 3105. The aspiration component includes a vacuum source and an aspirator connected to the vacuum source. In the non-limiting embodiment shown in FIG. 31, tissue cutting system 3100 includes an external vacuum source 3145 (e.g., a vacuum pump or a water aspirator) in fluid communication through a flow conduit 3150 (e.g., surgical tubing) with an aspirator 3155 attached to tissue cutting device 3105. In an aspect, at least a portion of the aspiration component is incorporated into the tissue cutting device. In some embodiments, the aspirator of the aspiration component includes a suction lumen disposed in and defined by the central rotatable shaft of the tissue cutting device, the suction lumen connected to vacuum source and in fluid communication with one or more openings defined by the central rotatable shaft of the tissue cutting device. In an aspect, the one or more openings defined by the central rotatable shaft of the tissue cutting device are positioned along the length of the central rotatable shaft of the tissue cutting device. In some embodiments, the entirety of the aspiration component, i.e., the vacuum source and the aspirator, may be incorporated into the tissue cutting device of the tissue cutting system.

In some embodiments, tissue cutting system 3100 includes an irrigation component configured to irrigate tissue in proximity to the central rotatable shaft 3115, the irrigation component including a flow conduit attached to an irrigation fluid reservoir. In an aspect, at least a portion of the irrigation component is incorporated into the tissue cutting device 3105. In the non-limiting embodiment shown in FIG. 31, tissue cutting system 3100 includes an external irrigation fluid reservoir 3160 in fluid communication through a flow conduit 3165 (e.g., surgical tubing) with an irrigation tube 3170 positioned proximal to the central rotatable shaft 3115 of the tissue cutting device 3105. In some embodiments, the flow conduit of the irrigation component includes an irrigation lumen disposed in and defined by the central rotatable shaft of the tissue cutting device, the irrigation lumen connected to the irrigation fluid reservoir and in fluid communication with one or more openings defined by the central rotatable shaft of the tissue cutting device. In some embodiments, the entirety of the irrigation component may be incorporated into the tissue cutting device of the tissue cutting system. In some embodiments, the entirety of the irrigation component may be a separate entity from the tissue cutting device. For example, the irrigation tube attached to the irrigation fluid reservoir may be physically separated from the tissue cutting device and held by a second hand of a user, e.g., a physician, or a second practitioner, e.g., a nurse. The irrigation fluid reservoir 3160 is configured to hold and controllably release at least one irrigation fluid. In an aspect, the at least one irrigation fluid includes at least one of saline, a buffer, a therapeutic agent, an antimicrobial agent, an anesthetic, or a coagulant agent. In an aspect, a tissue cutting system includes an aspiration component and an irrigation component.

In some embodiments, tissue cutting system 3100 includes an image-capture device 3175, the image-capture device operably coupled to the computing component 3110, computing component 3110 including circuitry configured to receive image data from the image-capture device. In an aspect, the received image data includes one or more images of a tissue in proximity to the central rotatable shaft of the tissue cutting device. For example, the image-capture device can be configured to collect images of a target tissue before, during, and/or after a cutting or resection procedure to monitor progress and success of the procedure. In an aspect, the image-capture device includes an optical image-capture device. In an aspect, the image-capture device includes an ultrasound image-capture device. In an aspect, at least a portion of the image-capture device is incorporated into tissue cutting device 3105. In the non-limiting embodiment shown in FIG. 31, tissue cutting system 3100 includes image-capture device 3175 incorporated into tissue cutting device 3105. In other embodiments, the image-capture device may include an external image-capture device, e.g., a digital camera or laparoscope. In an aspect, computing component 3110 includes circuitry configured to control at least one of the motor 3125 and the tethering component 3135 of tissue cutting device 3105 in response to the received image data.

In some embodiments, tissue cutting system 3100 includes at least one analyte sensor. In an aspect, at least a portion of the analyte sensor is incorporated into the tissue cutting device 3105. In the non-limiting embodiment shown in FIG. 31, tissue cutting system 3100 includes at least a portion of at least one analyte sensor 3180 is incorporated into the tissue cutting device 3105. In an aspect, the at least one analyte sensor may be external to the tissue cutting device. For example, the at least one analyte sensor may be positioned in or accessible from the flow conduit 3150 leading to the vacuum source 3145 of tissue cutting system 3100. In an aspect, the at least one analyte sensor includes at least one of an optical sensor, a magnetic sensor, an electrical sensor, an acoustic sensor, or a chemical sensor. In an aspect, the at least one analyte sensor is configured to sense a property of one or more analytes in an aspirate. In an aspect, the at least one analyte sensor is configured to sense an optical property, a fluorescence property, a magnetic property, an electrical property, an electromagnetic property, an acoustic property, or a chemical property of the one or more analytes in the aspirate. In an aspect, the at least one analyte sensor is operably coupled to the computing component 3110, the computing component 3110 including circuitry configured to receive sensor input from the at least one analyte sensor and to control at least one of the motor 3125 and the tethering component 3135 in response to the received sensor input.

In some embodiments, tissue cutting system 3100 includes a torque compensation component 3185. In an aspect, the torque compensation component 3185 includes circuitry configured to prevent oscillation. For example, the torque compensation component is configured to prevent oscillation of the tissue cutting device when performing asymmetric cutting patterns. In an aspect, the torque compensation component of tissue cutting system 3100 includes at least one counterweight. In an aspect, the at least one counterweight is extendable.

In some embodiments, tissue cutting system 3100 includes drag compensation component 3190. In an aspect, the drag compensation component 3190 includes circuitry configured to measure drag from the elongated flexible cutting component 3130 of tissue cutting device 3105 during rotation. The drag compensation component 3190 is operably coupled to the computing component 3110. The computing component 3110 including circuitry configured to control at least one of the motor 3125 and the tethering component 3135 in response to the measured drag.

In some embodiments, tissue cutting system 3100 includes a cautery component 3195 to cauterize tissue. For example, tissue cutting system 3100 can include a cautery component configured to cauterize tissue before, during, and/or after a cutting procedure. In an aspect, the cautery component is operably coupled to the elongated flexible cutting component 3130. For example, the elongated flexible cutting component can be configured to cauterize tissue before, during, and/or after a cutting procedure. In an aspect, the cautery component includes an electrical cautery component. For example, the elongated flexible cutting component may be configured to heat up upon carrying an electrical current. In an aspect, the cautery component includes an optical cautery component. In an aspect, the cautery component includes a thermal cautery component. For example, the elongated flexible cutting component may be configured to hold heat. In an aspect, the cautery component includes a chemical cautery component. For example, the irrigation fluid reservoir may be configured to hold and controllably release a chemical cauterizing agent. In an aspect, at least a portion of the cautery component is incorporated into the tissue cutting device.

The state of the art has progressed to the point where there is little distinction left between hardware, software, and/or firmware implementations of aspects of systems; the use of hardware, software, and/or firmware is generally (but not always, in that in certain contexts the choice between hardware and software can become significant) a design choice representing cost vs. efficiency tradeoffs. There are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer can opt for a mainly hardware and/or firmware vehicle; alternatively, if flexibility is paramount, the implementer can opt for a mainly software implementation; or, yet again alternatively, the implementer can opt for some combination of hardware, software, and/or firmware. Hence, there are several possible vehicles by which the processes and/or devices and/or other technologies described herein can be effected, none of which is inherently superior to the other in that any vehicle to be utilized is a choice dependent upon the context in which the vehicle will be deployed and the specific concerns (e.g., speed, flexibility, or predictability) of the implementer, any of which can vary. Optical aspects of implementations will typically employ optically-oriented hardware, software, and or firmware.

In some implementations described herein, logic and similar implementations can include software or other control structures. Electronic circuitry, for example, can have one or more paths of electrical current constructed and arranged to implement various functions as described herein. In some implementations, one or more media can be configured to bear a device-detectable implementation when such media hold or transmit a device detectable instructions operable to perform as described herein. In some variants, for example, implementations can include an update or modification of existing software or firmware, or of gate arrays or programmable hardware, such as by performing a reception of or a transmission of one or more instructions in relation to one or more operations described herein. Alternatively or additionally, in some variants, an implementation can include special-purpose hardware, software, firmware components, and/or general-purpose components executing or otherwise invoking special-purpose components. Specifications or other implementations can be transmitted by one or more instances of tangible transmission media as described herein, optionally by packet transmission or otherwise by passing through distributed media at various times.

Alternatively or additionally, implementations can include executing a special-purpose instruction sequence or invoking circuitry for enabling, triggering, coordinating, requesting, or otherwise causing one or more occurrences of virtually any functional operations described herein. In some variants, operational or other logical descriptions herein can be expressed as source code and compiled or otherwise invoked as an executable instruction sequence. In some contexts, for example, implementations can be provided, in whole or in part, by source code, such as C++, or other code sequences. In other implementations, source or other code implementation, using commercially available and/or techniques in the art, can be compiled//implemented/translated/ converted into a high-level descriptor language (e.g., initially implementing described technologies in C or C++ programming language and thereafter converting the programming language implementation into a logic-synthesizable language implementation, a hardware description language implementation, a hardware design simulation implementation, and/or other such similar mode(s) of expression). For example, some or all of a logical expression (e.g., computer programming language implementation) can be manifested as a Verilog-type hardware description (e.g., via Hardware Description Language (HDL) and/or Very High Speed Integrated Circuit Hardware Descriptor Language (VHDL)) or other circuitry model which can then be used to create a physical implementation having hardware (e.g., an Application Specific Integrated Circuit). Those skilled in the art will recognize how to obtain, configure, and optimize suitable transmission or computational elements, material supplies, actuators, or other structures in light of these teachings.

The foregoing detailed description has set forth various embodiments of the devices and/or processes via the use of block diagrams, flowcharts, and/or examples. Insofar as such block diagrams, flowcharts, and/or examples contain one or more functions and/or operations, each function and/or operation within such block diagrams, flowcharts, or examples can be implemented, individually and/or collectively, by a wide range of hardware, software, firmware, or virtually any combination thereof. In one embodiment, several portions of the subject matter described herein can be implemented via Application Specific Integrated Circuits (ASICs), Field Programmable Gate Arrays (FPGAs), digital signal processors (DSPs), or other integrated formats. However, some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link (e.g., transmitter, receiver, transmission logic, reception logic, etc.), etc.).

In a general sense, the various embodiments described herein can be implemented, individually and/or collectively, by various types of electro-mechanical systems having a wide range of electrical components such as hardware, software, firmware, and/or virtually any combination thereof; and a wide range of components that can impart mechanical force or motion such as rigid bodies, spring or torsional bodies, hydraulics, electro-magnetically actuated devices, and/or virtually any combination thereof. Consequently, as used herein "electro-mechanical system" includes, but is not limited to, electrical circuitry operably coupled with a transducer (e.g., an actuator, a motor, a piezoelectric crystal, a Micro Electro Mechanical System (MEMS), etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), electrical circuitry forming a communications device (e.g., a modem, communications switch, optical-electrical equipment, etc.), and/or any non-electrical analog thereto, such as optical or other analogs. Examples of electro-mechanical systems include but are not limited to a variety of consumer electronics systems, medical devices, as well as other systems such as motorized transport systems, factory automation systems, security systems, and/or communication/computing systems. Electro-mechanical as used herein is not necessarily limited to a system that has both electrical and mechanical actuation except as context can dictate otherwise.

In a general sense, the various aspects described herein can be implemented, individually and/or collectively, by a wide range of hardware, software, firmware, and/or any combination thereof and can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of memory (e.g., random access, flash, read only, etc.)), and/or electrical circuitry forming a communications device (e.g., a modem, communications switch, optical-electrical equipment, etc.). The subject matter described herein can be implemented in an analog or digital fashion or some combination thereof.

At least a portion of the devices and/or processes described herein can be integrated into an image processing system. A typical image processing system generally includes one or more of a system unit housing, a video display device, memory such as volatile or non-volatile memory, processors such as microprocessors or digital signal processors, computational entities such as operating systems, drivers, applications programs, one or more interaction devices (e.g., a touch pad, a touch screen, an antenna, etc.), control systems including feedback loops and control motors (e.g., feedback for sensing lens position and/or velocity; control motors for moving/distorting lenses to give desired focuses). An image processing system can be implemented utilizing suitable commercially available components, such as those typically found in digital still systems and/or digital motion systems.

At least a portion of the devices and/or processes described herein can be integrated into a data processing system. A data processing system generally includes one or more of a system unit housing, a video display device, memory such as volatile or non-volatile memory, processors such as microprocessors or digital signal processors, computational entities such as operating systems, drivers, graphical user interfaces, and applications programs, one or more interaction devices (e.g., a touch pad, a touch screen, an antenna, etc.), and/or control systems including feedback loops and control motors (e.g., feedback for sensing position and/or velocity; control motors for moving and/or adjusting components and/or quantities). A data processing system can be implemented utilizing suitable commercially available components, such as those typically found in data computing/communication and/or network computing/communication systems.

The herein described components (e.g., operations), devices, objects, and the discussion accompanying them are used as examples for the sake of conceptual clarity and that various configuration modifications are contemplated. Consequently, as used herein, the specific examples set forth and the accompanying discussion are intended to be representative of their more general classes. In general, use of any specific example is intended to be representative of its class, and the non-inclusion of specific components (e.g., operations), devices, and objects should not be taken limiting.

The herein described subject matter sometimes illustrates different components contained within, or connected with, different other components. It is to be understood that such depicted architectures are merely examples, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected," or "operably coupled," to each other to achieve the desired functionality, and any two components capable of being so associated can also be viewed as being "operably couplable," to each other to achieve the desired functionality. Specific examples of operably couplable include but are not limited to physically mateable and/or physically interacting components, and/or wirelessly interactable, and/or wirelessly interacting components, and/or logically interacting, and/or logically interactable components.

With respect to the use of substantially any plural and/or singular terms herein, the plural can be translated to the singular and/or from the singular to the plural as is appropriate to the context and/or application. The various singular/plural permutations are not expressly set forth herein for sake of clarity.

In some instances, one or more components can be referred to herein as "configured to," "configured by," "configurable to," "operable/operative to," "adapted/adaptable," "able to," "conformable/conformed to," etc. Those skilled in the art will recognize that such terms (e.g. "configured to") can generally encompass active-state components and/or inactive-state components and/or standby-state components, unless context requires otherwise.

While particular aspects of the present subject matter described herein have been shown and described, changes and modifications can be made without departing from the subject matter described herein and its broader aspects and, therefore, the appended claims are to encompass within their scope all such changes and modifications as are within the true spirit and scope of the subject matter described herein. Terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). If a specific number of an introduced claim recitation is intended, such an intent will be explicitly recited in the claim, and in the absence of such recitation no such intent is present. For example, as an aid to understanding, the following appended claims can contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g.,"a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). Typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

All of the above U.S. patents, U.S. patent application publications, U.S. patent applications, foreign patents, foreign patent applications and non-patent publications referred to in this specification and/or listed in any Application Data Sheet, are incorporated herein by reference, to the extent not inconsistent herewith.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:
1. A tissue cutting device comprising:
a central rotatable shaft having a first end and a second end;
a motor operably coupled to the first end of the central rotatable shaft, the motor including circuitry configured to rotate the central rotatable shaft;

an image-capture device configured to capture one or more images representative of one or more properties of a tissue or tissue constituents in proximity to the central rotatable shaft of the tissue cutting device;
a tethering component;
an elongated flexible cutting component having a first end and a second end, the first end of the elongated flexible cutting component secured to the central rotatable shaft at a position between the first end and the second end of the central rotatable shaft, the second end of the elongated flexible cutting component operably coupled to the tethering component, the tethering component configured to at least one of extend and retract the elongated flexible cutting component; and
a computing component operably coupled to the motor, the image-capture device, and the tethering component, the computing component including
circuitry configured to receive one or more images from the image-capture device during a resection process; and
circuitry configured to alter a function of at least one of the motor or the tethering component in response to the received one or more images from the image-capture device to change a shape formed by the elongated flexible cutting component during the resection process.

2. The device of claim 1, wherein the computing component includes circuitry configured to control rotational frequency of the motor.

3. The device of claim 1, wherein the computing component includes circuitry configured to control at least one of extension and retraction of the elongated flexible cutting component by the tethering component.

4. The device of claim 1, wherein the tethering component includes at least one rotatable component, the second end of the elongated flexible cutting component secured to the at least one rotatable component, the at least one rotatable component configured to at least one of extend and retract the elongated flexible cutting component.

5. The device of claim 1, wherein the tethering component includes a securing device, the securing device configured to secure the elongated flexible cutting component at a specified length.

6. The device of claim 1, wherein the tethering component is configured to rotate with the central rotatable shaft.

7. The device of claim 1, wherein the elongated flexible cutting component is at least one of a flexible wire, strand, string, fiber, thread, or ribbon.

8. The device of claim 1, wherein at least a portion of the elongated flexible cutting component between the first and the second end of the elongated flexible cutting component is disposed in a lumen defined by the central rotatable shaft.

9. The device of claim 1, wherein at least a portion of the elongated flexible cutting component between the first end and the second end of the elongated flexible cutting component extends past a rotatable element associated with the central rotatable shaft.

10. The device of claim 1, further comprising:
two or more elongated flexible cutting components, wherein a first end of each of the two or more elongated flexible cutting components is secured to the central rotatable shaft and a second end of each of the two or more elongated flexible cutting components is operably coupled to the tethering component.

11. The device of claim 1, further comprising:
an aspiration component configured to aspirate tissue debris in proximity to the central rotatable shaft, the aspiration component including
a vacuum source; and
an aspirator connected to the vacuum source.

12. The device of claim 11, wherein the aspirator includes a suction lumen disposed in and defined by the central rotatable shaft, the suction lumen connected to the vacuum source and in fluid communication with one or more openings defined by the central rotatable shaft.

13. The device of claim 1, further comprising:
an irrigation component configured to irrigate tissue in proximity to the central rotatable shaft, the irrigation component including a flow conduit attached to an irrigation fluid reservoir.

14. The device of claim 13, wherein the flow conduit includes an irrigation lumen disposed in and defined by the central rotatable shaft, the irrigation lumen connected to the irrigation fluid reservoir and in fluid communication with one or more openings defined by the central rotatable shaft.

15. The device of claim 1, further comprising:
at least one analyte sensor.

16. The device of claim 15, wherein the at least one analyte sensor is configured to sense a property of one or more analytes in an aspirate.

17. The device of claim 1, further comprising:
a drag compensation component.

18. The device of claim 1, further comprising:
a torque compensation component including circuitry configured to prevent oscillation when performing asymmetric cutting patterns.

19. The device of claim 18, wherein the torque compensation component includes at least one counterweight associated with the central rotating shaft.

20. The device of claim 1, further comprising:
a cautery component to cauterize tissue, wherein the cautery component is operably coupled to the elongated flexible cutting component.

21. A tissue cutting system comprising:
a tissue cutting device including
a central rotatable shaft having a first end and a second end;
a motor operably coupled to the first end of the central rotatable shaft, the motor including circuitry configured to rotate the central rotatable shaft;
a tethering component;
an elongated flexible cutting component having a first end and a second end, the first end of the elongated flexible cutting component secured to the central rotatable shaft at a position between the first and the second end of the central rotatable shaft, the second end of the elongated flexible cutting component operably coupled to the tethering component, the tethering component configured to at least one of extend and retract the elongated flexible cutting component, wherein extension and retraction of the elongated flexible cutting component changes a shape formed by the elongated flexible cutting component;
an aspiration component including a suction lumen disposed in and defined by the central rotatable shaft of the tissue cutting device, the suction lumen connected to a vacuum source and in fluid communication with one or more openings defined by the central rotatable shaft of the tissue cutting device; and at least one analyte sensor including circuitry configured to sense a property of one or more analytes in an aspirate; and a computing component operably connected to the tissue cutting device, the computing component including a processor and circuitry including circuitry configured to receive sensor output from the at least one analyte sensor, the sensor output including information regarding the sensed property of the one or more analytes in the aspirate; and circuitry configured to control at least one of the motor and the tethering component in response to the received sensor input including the information regarding the sensed property of the one or more analytes in the aspirate.

22. The system of claim 21, wherein the tethering component of the tissue cutting device is attached to the central rotatable shaft.

23. The system of claim 21, wherein the tethering component of the tissue cutting device is disposed in a lumen defined by the central rotatable shaft.

24. The system of claim 21, wherein the tethering component of the tissue cutting device is configured to rotate with the central rotatable shaft.

25. The system of claim 21, wherein at least a portion of the elongated flexible cutting component of the tissue cutting device between the first end and the second end of the elongated flexible cutting component is disposed in a lumen defined by the central rotatable shaft of the tissue cutting device.

26. The system of claim 21, wherein at least a portion of the elongated flexible cutting component of the tissue cutting device between the first end and the second end of the elongated flexible cutting component extends past a rotatable element on the central rotatable shaft of the tissue cutting device.

27. The system of claim 21, wherein the computing component includes circuitry configured to control rotational frequency of the motor.

28. The system of claim 21, wherein the computing component includes circuitry configured to control at least one of extension and retraction of the elongated flexible cutting component by the tethering component.

29. The system of claim 21, wherein the computing component includes circuitry configured to control at least one of extension and retraction of the elongated flexible cutting component by the tethering component and the rotational frequency of the motor operably coupled to the central rotatable shaft to generate an asymmetrical cutting pattern.

30. The system of claim 21, further comprising:
an irrigation component configured to irrigate tissue in proximity to the central rotatable shaft, the irrigation component including a flow conduit attached to an irrigation fluid reservoir.

31. The system of claim 21, further comprising:
an image-capture device, the image-capture device operably coupled to the computing component, the component including circuitry configured to receive image data from the image-capture device, wherein the received image data includes one or more images of a tissue in proximity to the central rotatable shaft of the tissue cutting device.

32. The system of claim 31, wherein the computing component includes circuitry configured to control at least one of the motor and the tethering component of the tissue cutting device in response to the received image data.

33. The system of claim 21, further comprising:
a drag compensation component.

34. The system of claim 33, wherein the drag compensation component includes circuitry configured to measure drag from the elongated flexible cutting component during rotation, the drag compensation component operably coupled to the computing component, the computing component including circuitry configured to control at least one of the motor and the tethering component in response to the measured drag.

35. The system of claim 21, further comprising:
a torque compensation component configured to prevent oscillation of the tissue cutting device when performing asymmetric cutting patterns.

36. The system of claim 35, wherein the torque compensation component includes at least one counterweight.

37. The system of claim 21, further comprising:
a cautery component to cauterize tissue.

38. A tissue cutting system comprising:
a tissue cutting device including
a central rotatable shaft having a first end and a second end;
a motor operably coupled to the first end of the central rotatable shaft, the motor including circuitry configured to rotate the central rotatable shaft;
a tethering component;
an elongated flexible cutting component having a first end and a second end, the first end of the elongated flexible cutting component secured to the central rotatable shaft at a position between the first and the second end of the central rotatable shaft, the second end of the elongated flexible cutting component operably coupled to the tethering component, the tethering component configured to at least one of extend and retract the elongated flexible cutting component, wherein extension and retraction of the elongated flexible cutting component changes a shape formed by the elongated flexible cutting component, wherein the elongated flexible cutting component is formed from a current-conducting material;
a cautery component configured to pass an electrical current through the current-conducting material of the elongated flexible cutting component during a resection process; and
a computing component operably connected to the tissue cutting device, the computing component including a processor and circuitry configured to control a function of the tethering component to at least one of extend and retract the elongated flexible cutting component to vary the shape formed by the elongated flexible cutting component during the resection process.

39. The system of claim 38, further comprising:
an aspiration component and an irrigation component.

40. The system of claim 38, further comprising:
an image-capture device including circuitry configured to capture one or more images representative of one or more properties of a tissue or tissue constituents in proximity to the central rotatable shaft of the tissue cutting device, the image-capture device operably coupled to the computing component, the computing component including circuitry configured to receive image data from the image-capture device and to alter a function of at least one of the motor or the tethering component in response to the received one or more images from the image-capture device to change a shape formed by the elongated flexible cutting component.

41. The system of claim 38, further comprising:
at least one analyte sensor including circuitry configured to sense a property of one or more analytes in an aspirate, the at least one analyte sensor operably coupled to the computing component, the computing component including circuitry configured to receive sensor output from the at least one analyte sensor, the sensor output including information regarding the sensed property of the one or more analytes in the aspirate and to control at least one of the motor and the tethering component in response to the received sensor input to change a shape formed by the elongated flexible cutting component.

\* \* \* \* \*